(12) United States Patent
Pineau et al.

(10) Patent No.: US 12,295,969 B2
(45) Date of Patent: May 13, 2025

(54) PHARMACEUTICAL COMPOSITION COMPRISING CYCLODEXTRIN COMPLEXES OF ANETHOLE TRITHIONE OR DERIVATIVES THEREOF

(71) Applicant: Frédéric Marin, Paris (FR)

(72) Inventors: Nicolas Pineau, Carbon-Blanc (FR); El Mustapha Belgsir, Poitiers (FR); Frédéric Turpin, Tours (FR); Anne-Gaëlle Fournial, La Madeleine (FR); Aswin Dereymaker, Halle (BE); Natascha Audoore, Merelbeke (BE); Ine De Cock, Ghent (BE)

(73) Assignee: Frédéric Marin, Paris (FR)

( * ) Notice: Subject to any disclaimer, the term of this patent is extended or adjusted under 35 U.S.C. 154(b) by 1002 days.

(21) Appl. No.: 17/273,928

(22) PCT Filed: Sep. 6, 2019

(86) PCT No.: PCT/EP2019/073873
§ 371 (c)(1),
(2) Date: Mar. 5, 2021

(87) PCT Pub. No.: WO2020/049166
PCT Pub. Date: Mar. 12, 2020

(65) Prior Publication Data
US 2021/0308173 A1      Oct. 7, 2021

Related U.S. Application Data

(60) Provisional application No. 62/727,691, filed on Sep. 6, 2018.

(30) Foreign Application Priority Data

Sep. 6, 2018 (EP) .................................. 18306172

(51) Int. Cl.
| | | |
|---|---|---|
| *A61K 31/737* | (2006.01) | |
| *A61K 9/19* | (2006.01) | |
| *A61K 31/385* | (2006.01) | |
| *A61K 31/423* | (2006.01) | |
| *A61K 31/427* | (2006.01) | |
| *A61K 31/428* | (2006.01) | |
| *A61K 47/02* | (2006.01) | |
| *A61K 47/12* | (2006.01) | |

(52) U.S. Cl.
CPC .............. *A61K 31/737* (2013.01); *A61K 9/19* (2013.01); *A61K 31/385* (2013.01); *A61K 31/423* (2013.01); *A61K 31/427* (2013.01); *A61K 31/428* (2013.01); *A61K 47/02* (2013.01); *A61K 47/12* (2013.01)

(58) Field of Classification Search
CPC .. A61K 31/737; A61K 31/385; A61K 31/423; A61K 31/427; A61K 31/428; A61K 47/6951; C08B 37/0015; A61P 43/00

USPC ........................................................ 514/58
See application file for complete search history.

(56) References Cited

U.S. PATENT DOCUMENTS

| | | | | | |
|---|---|---|---|---|---|
| 10,272,066 | B2 * | 4/2019 | Diolez | ................ | A61K 31/385 |
| 10,653,668 | B2 * | 5/2020 | Diolez | ................ | A61K 31/497 |
| 11,318,113 | B2 * | 5/2022 | Diolez | ................ | A61K 31/497 |
| 11,484,529 | B2 * | 11/2022 | Diolez | ................ | C07D 285/08 |

FOREIGN PATENT DOCUMENTS

| | | |
|---|---|---|
| WO | 98/27970 A2 | 7/1998 |
| WO | 2017/042267 A1 | 3/2017 |

OTHER PUBLICATIONS

Wang et al, J. Immunol., 2007, 179, 5958-5965.*
Dollo et al, J. Pharm. Sci., 1999, 88(9), 889-895.*
Pharmaceutical Technology, 2013, 37(5), 1-6.*
K.M. DeAgnelis, Phosphate Buffer, 2007, p. 1.*
Written Opinion of the International Searching Authority issued on Mar. 12, 2020, in connection with international Application No. PCT/EP2019/073873, 7 pp.
Gilles Dollo, et al., "Improvement in Solubility and Dissolution Rate of 1,2-Dithiole-3-thiones upon Complexation with [beta]-Cyclodextrin and Its Hydroxypropyl and Sulfobutyl Ether-7 Derivatives", Journal of Pharmaceutical Sciences, vol. 88, No. 9, Sep. 1999, pp. 889-895 (7 pp.).
Ying Zheng, et al., "Physicochemical and Structural Characterization of Quercetin-[beta]-Cyclodextrin Complexes", Journal of Pharmaceutical Sciences, vol. 94, No. 5, May 2005, pp. 1079-1089 (11 pp.).
Hong-Zhen Yu, et al., "An Examination of the Potential Effect of Lipids on the First-Pass Metabolism of the Lipophilic Drug Anethol Trithione", Journal of Pharmaceutical Sciences, vol. 100, No. 11, Nov. 2011, pp. 5048-5058 (11 pp.).
Mohd Imran Ansari, et al., "Dithiolethiones: a privileged pharmacophore for anticancer therapy and chemoprevention", Future Medicinal Chemistry, vol. 10, No. 10, May 2018, pp. 1241-1260 (20 pp.).
Daniela Giustarini, et al., "The new H2S-releasing compound ACS94 exerts protective effects through the modulation of thiol homoeostasis", Journal of Enzyme Inhibition and Medicinal Chemistry, vol. 33, No. 1, Jan. 4, 2018, pp. 1392-1404 (13 pp.).

\* cited by examiner

*Primary Examiner* — Ganapathy Krishnan
(74) *Attorney, Agent, or Firm* — Maier & Maier, PLLC

(57) ABSTRACT

A composition including anethole trithione or a derivative thereof of formula (I), sulfobutyl ether-beta-cyclodextrin and optionally a co-solvent, wherein the ratio of the sulfobutyl ether-beta-cyclodextrin to the compound of formula (I) ranges from 10 to 400, preferably from 57 to 200. Also, the use of the composition as a drug, namely for the treatment and/or the prevention of free oxygen radical-related diseases. Further, a kit-of-parts and/or a medical device including the composition. Lastly, a method for solubilizing a compound of formula (I) in an aqueous medium.

14 Claims, 3 Drawing Sheets

PHARMACEUTICAL COMPOSITION COMPRISING CYCLODEXTRIN COMPLEXES OF ANETHOLE TRITHIONE OR DERIVATIVES THEREOF

FIELD

The present invention relates to galenic formulations of anethole trithione and derivatives thereof. More in particular, the present invention is directed to a method as well as a formulation leading to the aqueous solubility enhancement of anethole trithione and derivatives thereof. It was found by the Applicant that the solubility enhancement method and formulation according to the present invention maintain the syringeability of the obtained compositions while they enhance the chemical stability of such compounds in aqueous media. Thus, the present invention leads the way to injectable formulations, preferably anethole trithione or derivatives thereof aqueous formulations or powder formulations to be reconstituted in aqueous media.

BACKGROUND

It is well established in the art that the inhibition of the production of reactive oxygen species (ROS) is a key-point for treating of a large spectrum of diseases.

Various antioxidants have been tested with regard to the physiological and pathological roles of ROS. Antioxidant research has provided numerous natural and designed molecules that modulate ROS with various selectivity against the different origins of ROS, being physiological (cellular signaling) or pathological. However, although ROS have been related to numerous diseases, and antioxidants have shown promises in many preclinical experiments, nearly all clinical trials of antioxidant-based therapeutics have shown limited efficacy (Orr et al., 2013. *Free Radic Biol Med.* 65:1047-59).

In addition, several studies have also demonstrated that excessive reduction of ROS in cells is deleterious and it appears that an adequate balance of ROS production is necessary for cell functioning (Goodman et al., 2004. *J Natl Cancer Inst.* 96(23):1743-50; Bjelakovic et al., 2007. *JAMA.* 297(8):842-57). As a consequence, there is a growing interest in the selective inhibition of ROS production by mitochondria that would not affect cellular signaling by cytosolic ROS production.

International patent applications WO2017/042267 and PCT/EP2018/055651 show the selective inhibition of the production of oxygen radicals (ROS) by anethole trithione (AOL, also referred to as ATT), AOL derivatives and especially bio-isosters thereof. Such compounds act predominantly at site $I_Q$ of complex I of the mitochondrial respiratory chain, the main mitochondrial site of ROS production and the main responsible site for mitochondrial dysfunctions.

Nevertheless, anethole trithione and derivatives thereof present limited intrinsic aqueous solubility that hinders the therapeutic potential of such site-selective ROS inhibitors.

Anethole trithione in particular presents an intrinsic aqueous solubility of less than 0.3 mg/L. Lipid-based formulations thereof have been proposed in order to enhance its limited solubility (Han et al., 2009. *Int J Pharm.* 379(1):18-24; Yu et al., 2011. *J Pharm Sci.* 100(11):5048-58). However, the solubilization of anethole trithione as described by Han et al. demands strenuous procedures (Han et al., 2009. *Int J Pharm.* 379(1):18-24). Furthermore, the Applicant has shown that anethole trithione is incompatible with lipid systems. In fact, such derivatives rapidly decompose within lipid-based formulations (see example 1 hereafter). Without willing to be bound by a theory, the reductive/oxidative properties of anethole derivatives render them incompatible with lipid formulation systems. Furthermore, the Chinese patent application CN1771938 discloses the solubilization of anethole trithione in lipidic microemulsions. Nevertheless, lipidic microemulsions are not suitable for intravenous injections, namely bolus intravenous injections (Sim et al., 2009. *BJCP* 67(3): 316-325).

Dollo et al. disclose the association of hydroxypropyl and sulfobutyl ether beta cyclodextrins with 1,2-dithiole-3-thiones, such as anethole trithione (Dollo et al., 1999. *J Pharm Sci.* 88(9): 889-895). The obtained compositions are suspensions and thus not suitable for being intravenously injected.

Consequently, the formulations wherein anethole trithione and derivatives thereof present an improved solubility and stability are still an unmet need. Indeed, Dollo et al. does not present any data concerning the chemical stability of the 1,2-dithiole-3-thiones within such formulations. The inventors after reproducing the formulation of anetholone trithione according to Dollo et al., they found that this active compound is significantly more stable within the formulation of the present invention.

The Applicant developed formulations of anethole trithione present an advantageous solubility and stability. Such formulations give way to optimal bioavailability of the anethole derivatives and to the possibility of preparing injectable medicaments of such poorly soluble and unstable compounds.

Advantageously, the formulations according to the invention respect the European Medicines Agency (EMA) guidelines of the maximal threshold of excipients such as cyclodextrins.

Even more advantageously, the invention's formulations present a viscosity that renders them suitable for being injected in a subject.

Another advantage of the invention's formulations is to enable both bolus and infusion administration of these lipophilic active ingredients.

SUMMARY

The present invention relates to a composition comprising a reactive oxygen species (ROS) inhibitor, preferably a selective inhibitor of the mitochondrial production of ROS. The composition according to the present invention comprises a solubilization vehicle and the inhibitor, thus allowing to enhance the aqueous solubility as well as the chemical stability of said inhibitor.

In one embodiment, the composition comprises sulfobutyl ether-beta-cyclodextrin and a compound of formula (I), as hereinafter described, wherein the molar ratio of the sulfobutyl ether-beta-cyclodextrin to the compound of formula (I) ranges from 10 to 400, preferably from 57 to 200.

In one embodiment, the compound of formula (I) is:

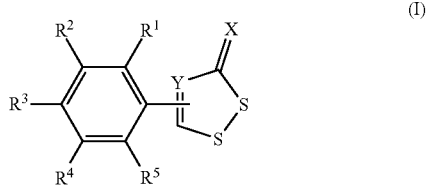

or a pharmaceutically acceptable tautomer, salt or solvate thereof wherein:

X represents S, O or NHOH; preferably X is S or O; more preferably, X is S;

Y represents CH, C or N; preferably Y is CH or N; more preferably Y is CH;

$R^1$, $R^2$, $R^4$ and $R^5$ each independently represent hydrogen, hydroxy, halo, amino, alkylsulfonyl, aminosulfonyl, cyano, nitro, carboxy, aryl, alkoxy, haloalkyl, alkylamino, aminoalkyl, nitrooxyalkyl or carboxyalkyl;

$R^3$ hydroxy or methoxy; or $R^3$ and $R^2$ together with the carbon atoms to which they are attached form a 5-membered heteroaryl moiety wherein —$R^3$—$R^2$— represents -A-$CR^6$=B— or —B=$CR^6$-A-; wherein:

A represents O, S or $NR^7$; wherein $R^7$ represents hydrogen, $C_1$-$C_8$ alkyl or alkyloxycarbonyl;

B represents CH or N; and $R^6$ represents hydrogen, hydroxy, halo, amino, alkylsulfonyl, aminosulfonyl, cyano, nitro, carboxy, aryl, alkoxy, haloalkyl, alkylamino, aminoalkyl, nitrooxyalkyl or carboxyalkyl.

In one embodiment, the compound of formula (I) is selected from: 5-(4-methoxyphenyl)-3H-1,2-dithiole-3-thione; 5-(4-hydroxyphenyl)-3H-1,2-dithiole-3-thione; 5-(4-hydroxyphenyl)-3H-1,2-dithiol-3-one; 5-(4-hydroxyphenyl)-3H-1,2-dithiol-3-one oxime; 5-(4-hydroxyphenyl)-3H-1,2,4-dithiazole-3-thione; 4-(4-hydroxyphenyl)-3H-1,2-dithiole-3-thione; 5-(2-hydroxybenzo[d]oxazol-5-yl)-3H-1,2-dithiole-3-thione; 5-(2-hydroxybenzo[d]thiazol-6-yl)-3H-1,2-dithiole-3-thione; 5-(benzofuran-5-yl)-3H-1,2-dithiole-3-thione; and methyl 5-(3-thioxo-3H-1,2-dithiol-5-yl)-1H-indole-1-carboxylate.

The concentration the of the compound of formula (I) in the composition according to the invention may range from 0.04 to 1.2 mg/mL, preferably from 0.1 to 1.0 mg/mL, even more preferably from 0.1 to 0.7 mg/mL.

In one embodiment, the amount of the sulfobutyl ether-beta-cyclodextrin ranges from 1 to 40% (w/w), preferably 2.5 to 30% (w/w), even more preferably from 5 to 20% (w/w), in weight relative to the total weight of the composition.

In one embodiment, the composition further comprises at least one buffer selected from citrate buffer, acetate buffer, tris(hydroxymethyl)aminomethane or phosphate buffer, preferably the buffer is a phosphate buffer.

In one embodiment, the composition has a pH ranging from 6 to 7.8, preferably from 6.5 to 7.5.

According to one embodiment, the composition is a solid composition.

In one embodiment, the composition further comprises at least one pharmaceutically acceptable liquid carrier, preferably the liquid carrier is an aqueous solution, more preferably, the liquid carrier is water.

In a second aspect, the invention relates to the composition, as previously described, for use as a drug.

In one embodiment, the invention relates to the composition, as previously described, for use as inhibitor of production of reactive oxygen species (ROS) in the treatment and/or prevention of free oxygen radical-related diseases.

In a third aspect, the invention relates a method for solubilizing in an aqueous medium a compound of formula (I), said method comprising the step of mixing the compound of formula (I) with sulfobutyl ether-beta-cyclodextrin, in a molar ratio of sulfobutyl ether-beta-cyclodextrin to compound of formula (I) ranging from 10 to 400, preferably 57 to 200.

In one embodiment, the mixing step is at a temperature ranging from 20° C. to 35° C., preferably 20 to 30° C.

In one embodiment, the method may further comprise adding a buffer selected from citrate buffer, acetate buffer, tris(hydroxymethyl)aminomethane or phosphate buffer, preferably a phosphate buffer.

In one embodiment, the method according comprising the steps of:

a) mixing the compound of formula (I) with sulfobutyl ether-beta-cyclodextrin, in a molar ratio of sulfobutyl ether-beta-cyclodextrin:compound of formula (I) ranging from 10 to 400, preferably 57 to 200; then b) lyophilizing the mix obtained in step (a) leading to the obtention of a powder; then c) reconstituting the powder of step (b) in an aqueous medium.

In a fourth aspect, the invention relates to kit-of-parts or a medical device comprising said kit-of-parts, wherein the kit-of-parts comprises the composition of the invention.

In the present invention, the following terms have the following meanings:

The term "about", preceding a figure, means plus or less 10% of the value of said figure.

The term "alkoxy" as used herein by itself or as part of another substituent refers to a group —O-alkyl wherein alkyl is as herein defined.

The term "alkyl" as used herein by itself or as part of another substituent refers to a hydrocarbyl radical of formula $C_nH_{2n+1}$ wherein n is a number greater than or equal to 1. Generally, alkyl groups of this invention comprise from 1 to 8 carbon atoms, preferably from 1 to 6 carbon atoms, more preferably from 1 to 4 carbon atoms, more preferably from 1 to 3 carbon atoms. Alkyl groups may be linear or branched. Suitable alkyl groups include methyl, ethyl, propyl, butyl, pentyl, hexyl, heptyl and octyl.

The term "alkylamino" as used herein by itself or as part of another substituent refers to a group —NH-alkyl wherein alkyl is as herein defined.

The term "alkyloxycarbonyl" as used herein by itself or as part of another substituent refers to a group —C(=O)—O— alkyl, wherein alkyl is as herein defined. A preferred alkyloxycarbonyl group is methyloxycarbonyl.

The term "alkylsulfonyl" as used herein by itself or as part of another substituent refers to a group —$SO_2$-alkyl wherein alkyl is as herein defined.

The term "amino" as used herein refers to a group —$NH_2$.

The term "aminoalkyl" as used herein by itself or as part of another substituent refers to a group -alkyl-$NH_2$ wherein alkyl is as herein defined.

The term "aminosulfonyl" as used herein by itself or as part of another substituent refers to a group —$SO_2$—$NH_2$.

The term "aryl" as used herein by itself or as part of another substituent refers to a polyunsaturated, aromatic hydrocarbyl group having a single ring (i.e., phenyl) or multiple aromatic rings fused together (e.g., naphtyl), typically containing 5 to 12 atoms; preferably 6 to 10. Non-limiting examples of aryl comprise phenyl, naphthalenyl.

The term "bio-isosteres" as used herein refers to compounds or groups that possess near-equal molecular shapes and volumes, approximately the same distribution of electrons, and which exhibit similar physical properties and similar biological activities.

The term "carboxy" as used herein refers to a group —COOH.

The term "carboxyalkyl" as used herein by itself or as part of another substituent refers to a group -alkyl-COOH wherein alkyl is as herein defined.

The term "degree of substitution" ("n" or DS) of a polymer, i.e., a substituted cyclodextrin, is the average number of substituent groups attached per base unit or per monomeric unit. In one embodiment, the "degree of substitution" is expressed as degree of molar substitution (MS). In one embodiment, the DS or MS of a mono- or multi-substituted cyclodextrin is indicated as a range of values. In one embodiment, the DS or MS of a mono- or multi-substituted cyclodextrin is indicated the median of the range of values measured in the population of cyclodextrins in the sample.

The term "halo" or "halogen" means fluoro, chloro, bromo, or iodo.

The term "haloalkyl" itself or as part of another substituent, refers to an alkyl radical as herein defined wherein one or more hydrogens are replaced with a halogen as herein defined. Non-limiting examples of haloalkyl include fluoromethyl, difluoromethyl and trifluoromethyl.

The term "heteroaryl" as used herein by itself or as part of another substituent refers to an aryl group as herein defined wherein at least one carbon atom is replaced with a heteroatom. In other words, it refers to 5 to 12 carbon-atom aromatic single rings or ring systems containing 2 rings which are fused together, typically containing 5 to 6 atoms; in which one or more carbon atoms is replaced by oxygen, nitrogen and/or sulfur atoms where the nitrogen and sulfur heteroatoms may optionally be oxidized and the nitrogen heteroatoms may optionally be quaternized. Non-limiting examples of such heteroaryl, include: oxazolyl, thiazolyl, imidazolyl, furanyl and pyrrolyl.

The terms "$IC_{50}$" or "half maximal inhibitory concentration" represent the concentration of an inhibitor that is required for 50% inhibition in vitro. It is comparable to an "$EC_{50}$" or "half maximal effective concentration" for agonist drugs. "$EC_{50}$" also represents the plasma concentration required for obtaining 50% of a maximum effect in vivo.

The expression "pharmaceutically acceptable excipient" refers to an excipient that does not produce an adverse, allergic or other untoward reaction when administered to an animal, preferably a human. It includes any and all solvents, dispersion media, coatings, antibacterial and antifungal agents, isotonic and absorption delaying agents and the like. For human administration, preparations should meet sterility, pyrogenicity, general safety and purity standards as required by regulatory offices, such as, e.g., FDA Office or EMA.

The term "ROS", as used herein, refers to reactive oxygen species. ROS are chemically reactive chemical species containing oxygen. Examples include, but are not limited to, peroxides ($[O-O]^{2-}$ and R—O—O—R, such as $H_2O_2$), superoxide ($O_2 \cdot ^-$), hydroxyl radical ($\cdot OH$) and singlet oxygen ($^1O_2$). In cells, ROS are produced as a byproduct of the metabolism of oxygen; however, environmental stress can lead to an increased ROS production by cells, termed "oxidative stress", leading to significant damage to cell structures. Several distinct sites of ROS production have been identified to date, among which mitochondria (and in particular, sites $I_Q$, $I_F$, $III_{QO}$, SDH and mGPDH of the mitochondrial respiratory chain), microsomes (e.g., cytochrome P450 and diamine oxidase), peroxisomes and some enzymes in the plasma membrane (e.g., NADPH oxidase and lipooxygenase). Depending on the location within the cell where ROS are released and stored, one may further distinguish between "cytosolic ROS" and "mitochondrial ROS". For example, complex I of the mitochondrial respiratory chain (sites $I_Q$ and $I_F$) and site SDH of the mitochondrial complex II produce and release ROS toward the mitochondrial lumen which are therefore considered as "mitochondrial ROS"; whereas complex III of the mitochondrial respiratory chain (site $III_{QO}$) and site mGPDH produce and release ROS toward the cell cytoplasm which are considered as "cytosolic ROS".

The term "nitrooxyalkyl" as used herein by itself or as part of another substituent refers to a group -alkyl-$ONO_2$ wherein alkyl is as herein defined.

The term "salt" of the compounds of the invention is used herein to describe the acid addition and base salts thereof. Suitable acid addition salts are formed from acids which form non-toxic salts. Non-limiting examples include the acetate, trifluoroacetate, adipate, aspartate, benzoate, besylate, bicarbonate/carbonate, bisulphate/sulphate, borate, tetrafluoroborate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Non-limiting examples include the aluminium, arginine, benzathine, calcium, choline, diethylamine, diolamine, glycine, lysine, magnesium, meglumine, olamine, potassium, sodium, tromethamine, 2-(diethylamino)ethanol, ethanolamine, morpholine, 4-(2-hydroxyethyl)morpholine and zinc salts. Hemisalts of acids and bases may also be formed, for example, hemisulphate and hemicalcium salts. Preferred, pharmaceutically acceptable salts include hydrochloride/chloride, hydrobromide/bromide, bisulphate/sulphate, nitrate, citrate, and acetate.

The term "site $I_Q$", as used herein, refers to the ubiquinone binding site of the NADH:ubiquinone oxidoreductase (also known as mitochondrial complex I). Site $I_Q$ produces ROS which are released inside the mitochondrial lumen.

The term "site $I_F$", as used herein, refers to the flavin binding site of mitochondrial complex I. Site $I_F$ produces ROS which are released inside the mitochondrial lumen.

The term "site $III_{QO}$", as used herein, refers to the ubiquinone binding site of the cytochrome bc1 complex (also known as mitochondrial complex III). Site $III_{QO}$ produces ROS which are released toward the cell cytoplasm.

The term "site SDH", as used herein, refers to succinate dehydrogenase (also known as mitochondrial complex II). Site SDH produces ROS which are released inside the mitochondrial lumen.

The term "site mGPDH", as used herein, refers to glycerol 3-phosphate dehydrogenase. Site mGPDH produces ROS which are released toward the cell cytoplasm.

The term "solvate" is used herein to describe a compound in this invention that contains stoichiometric or sub-stoichiometric amounts of one or more pharmaceutically acceptable solvent molecule such as ethanol or water. The term "hydrate" refers to when the said solvent is water.

The term "subject" refers to an animal, including a human. In the sense of the present invention, a subject may be a patient, i.e., a person receiving medical attention, undergoing or having underwent a medical treatment, or monitored for the development of a disease. In one embodiment, the subject is a male. In another embodiment, the subject is a female.

The term "tautomer" refers to organic compounds that are interconvertible by a chemical reaction called tautomerization. Said chemical reaction involves the migration of a hydrogen atom or proton, accompanied by a switch of a single bond and adjacent double bond.

The expression "therapeutically effective amount" means level or amount of agent that is aimed at, without causing significant negative or adverse side effects to the target, (1) delaying or preventing the onset of a disease, disorder, or condition related to free oxygen radicals; (2) slowing down or stopping the progression, aggravation, or deterioration of one or more symptoms of the disease, disorder, or condition related to free oxygen radicals; (3) bringing about ameliorations of the symptoms of the disease, disorder, or condition related to free oxygen radicals; (4) reducing the severity or incidence of the disease, disorder, or condition related to free oxygen radicals; or (5) curing the disease, disorder, or condition related to free oxygen radicals. A therapeutically effective amount may be administered prior to the onset of the disease, disorder, or condition related to free oxygen radicals, for a prophylactic or preventive action. Alternatively or additionally, the therapeutically effective amount may be administered after initiation of the disease, disorder, or condition related to free oxygen radicals, for a therapeutic action.

The terms "treating", "treatment" or "alleviation" refer to both therapeutic treatment and prophylactic or preventative measures; wherein the object is to prevent or slow down the targeted pathologic condition or disease. Those in need of treatment include those already with the disease as well as those prone to have the disease or those in whom the disease is to be prevented. A subject or mammal is successfully "treated" for a disease or affection or condition if, after receiving the treatment according to the present invention, the subject or mammal shows observable and/or measurable reduction in or absence of one or more of the following: reduction ROS production; and/or relief to some extent, for one or more of the symptoms associated with the specific disease or condition; reduced morbidity and mortality, and improvement in quality of life issues. The above parameters for assessing successful treatment and improvement in the disease are readily measurable by routine procedures familiar to a physician.

The term "selective inhibitor" as used herein can refer to a compound capable of inhibiting ROS production at site $I_Q$ of complex I, while having minimal effects on ROS production from the remaining sites and on mitochondrial membrane potential ($\Delta\Psi m$) and oxidative phosphorylation. For example, on isolated mitochondria, in the presence of rotenone (i.e., when ROS production at site $I_Q$ is inhibited) and antimycin A (i.e., when ROS are produced mainly by complex III), the $IC_{50}$ of the compound on the inhibition of ROS production is about 5, 6, 7, 8, 9, 10, 15, 20 times higher than in the absence of rotenone. For example, on isolated mitochondria, in the presence of rotenone (i.e., when ROS production at site $I_Q$ is inhibited), the $IC_{50}$ of the compound on the inhibition of ROS production is about 5, 6, 7, 8, 9, 10, 15, 20 times higher or more than in the presence of antimycin A (i.e., added after rotenone, therefore when ROS are produced mainly by complex III). In one embodiment, the term "selective inhibitor" as used herein can also refer, exclusively or inclusively with any one of the definitions given herein, to a compound capable of inhibiting mitochondrial ROS production at site $I_Q$ of complex I with an $IC_{50}$ ranging from about 0.1 µM to about 20 µM, preferably of about 10 µM. In one embodiment, the term "selective inhibitor" as used herein can also refer, exclusively or inclusively with any one of the definitions given herein, to a compound capable of inhibiting mitochondrial ROS production at site $I_Q$ of complex I with an $IC_{50}$ of about 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20 µM. In another embodiment, said compound does not significantly inhibit cytosolic ROS production in an in vitro assay of NAD(P)H oxidase ROS production.

DETAILED DESCRIPTION

Figure 1:
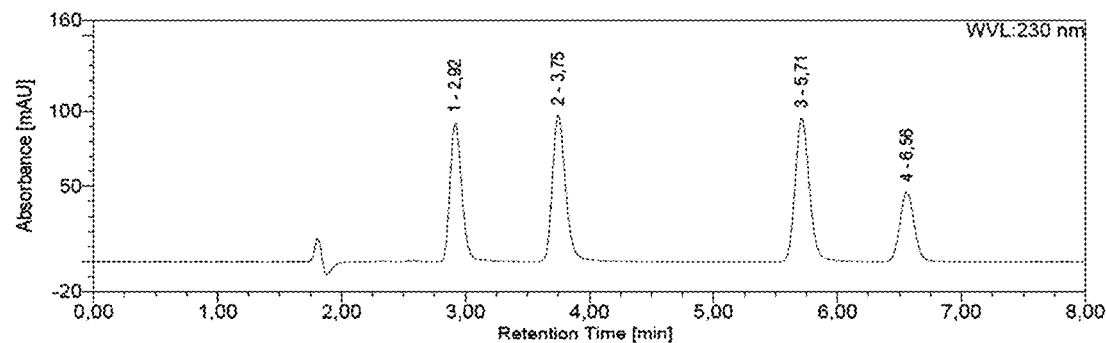
FIG. 1 is a HPLC chromatogram showing separation of AOL, trithioanole, thioamide and trans-anethole having a retention time of 2.92, 3.75, 5.71 and 6.56 minutes respectively. The detection was carried out at a wavelength of 230 nm.

This invention relates to a composition comprising an antioxidant, preferably an inhibitor of the mitochondrial production of reactive oxygen species (ROS), at least one solubilization vehicle and optionally at least one excipient.

Inhibitor of ROS Production

In one embodiment, the inhibitor of the mitochondrial production of reactive oxygen species (ROS) is selected from anethole trithione (AOL), a derivative thereof and a bio-isoster thereof.

Anethole trithione corresponds to 5-(4-methoxyphenyl)-3H-1,2-dithiole-3-thione.

In one embodiment, the inhibitor is a compound of formula (I)

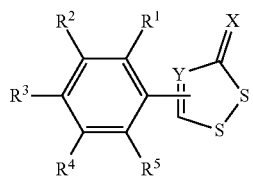

(I)

or a pharmaceutically acceptable tautomer, salt or solvate thereof wherein:
X represents S, O or NHOH; preferably X is S or O; more preferably, X is S;
Y represents CH, C or N; preferably Y is CH or N; more preferably Y is CH;
$R^1$, $R^2$, $R^4$ and $R^5$ each independently represent hydrogen, hydroxy, halo, amino, alkylsulfonyl, aminosulfonyl, cyano, nitro, carboxy, aryl, alkoxy, haloalkyl, alkylamino, aminoalkyl, nitrooxyalkyl or carboxyalkyl;
$R^3$ is hydroxy or methoxy; or $R^3$ and $R^2$ together with the carbon atoms to which they are attached form a 5-membered heteroaryl moiety wherein —$R^3$—$R^2$— represents -A-$CR^6$=B— or —B=$CR^6$-A-; wherein:
  A represents O, S or $NR^7$; wherein $R^7$ represents hydrogen, $C_1$-$C_8$ alkyl or alkyloxycarbonyl;
  B represents CH or N; and
  $R^6$ represents hydrogen, hydroxy, halo, amino, alkylsulfonyl, aminosulfonyl, cyano, nitro, carboxy, aryl, alkoxy, haloalkyl, alkylamino, aminoalkyl, nitrooxyalkyl or carboxyalkyl.

According to a preferred embodiment, in formula (I):
X represents S, O or NHOH; preferably X is S;
Y represents CH, C or N; preferably Y is CH;
$R^1$, $R^2$, $R^4$ and $R^5$ each independently represent hydrogen, hydroxy, halo, amino, alkylsulfonyl, aminosulfonyl, cyano, nitro, carboxy, aryl, alkoxy, haloalkyl, alkylamino, aminoalkyl, nitrooxyalkyl or carboxyalkyl; preferably $R^1$, $R^2$, $R^4$ and $R^5$ represent hydrogen;
$R^3$ is hydroxy or methoxy; or $R^3$ and $R^2$ together with the carbon atoms to which they are attached form a 5-membered heteroaryl moiety wherein —$R^3$—$R^2$— represents -A-$CR^6$=B—; wherein
  A represents O, S or $NR^7$; wherein $R^7$ represents hydrogen or $C_1$-$C_8$ alkyl group;
  B represents CH or N; and
  $R^6$ represents hydrogen, hydroxy, halo, amino, alkylsulfonyl, aminosulfonyl, cyano, nitro, carboxy, aryl, alkoxy, haloalkyl, alkylamino, aminoalkyl, nitrooxyalkyl or carboxyalkyl;

According to a preferred embodiment, X represents S. According to another preferred embodiment, X represents O. According to a preferred embodiment, Y represents CH. According to another preferred embodiment, Y represents N.

According to a preferred embodiment, $R^3$ represents methoxy. In another preferred embodiment, $R^3$ represents hydroxy, According to a preferred embodiment, $R^3$ and $R^2$ together with the carbon atoms to which they are attached form a 5-membered heteroaryl moiety, wherein —$R^3$—$R^2$— represents -A-$CR^6$=B—; wherein:
  A represents O, S or $NR^7$; wherein $R^7$ represents hydrogen, $C_1$-$C_8$ alkyl or alkyloxycarbonyl; preferably $R^7$ represents hydrogen or alkyloxycarbonyl;
  B represents CH or N; and
  $R^6$ represents hydrogen, hydroxy, halo, amino, alkylsulfonyl, aminosulfonyl, cyano, nitro, carboxy, aryl, alkoxy, haloalkyl, alkylamino, aminoalkyl, nitrooxyalkyl or carboxyalkyl; preferably $R^6$ represents hydrogen or hydroxyl.

More preferably, —$R^3$—$R^2$— represents —O—C(OH)=N— or —N(COOMe)-CH=CH—, more preferably —$R^3$—$R^2$— represents —O—C(OH)=N—.

According to another preferred embodiment, $R^3$ and $R^2$ together with the carbon atoms to which they are attached form a 5-membered heteroaryl moiety wherein —$R^3$—$R^2$— represents —B=$CR^6$-A-; wherein
  A represents O, S or $NR^7$; wherein $R^7$ represents hydrogen, $C_1$-$C_8$ alkyl or alkyloxycarbonyl; preferably $R^7$ represents hydrogen or alkyloxycarbonyl;
  B represents CH or N; and
  $R^6$ represents hydrogen, hydroxy, halo, amino, alkylsulfonyl, aminosulfonyl, cyano, nitro, carboxy, aryl, alkoxy, haloalkyl, alkylamino, aminoalkyl, nitrooxyalkyl or carboxyalkyl; preferably $R^6$ represents hydrogen or hydroxyl.

More preferably, —$R^3$—$R^2$— represents —N=C(OH)—S—.

According to a preferred embodiment, the inhibitors of the invention, are thus compounds of formula (I')

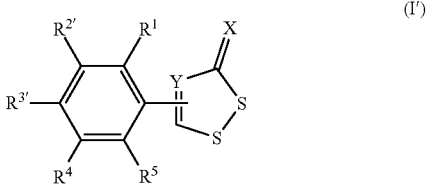

(I')

or a pharmaceutically acceptable tautomer, salt or solvate thereof wherein:
X represents S, O or NHOH; preferably X is S or O; more preferably, X is S;
Y represents CH, C or N; preferably Y is CH or N; more preferably Y is CH;
$R^1$, $R^4$ and $R^5$ each independently represent hydrogen, hydroxy, halo, amino, alkylsulfonyl, aminosulfonyl, cyano, nitro, carboxy, aryl, alkoxy, haloalkyl, alkylamino, aminoalkyl, nitrooxyalkyl or carboxyalkyl;

R2' and R3' together with the carbon atoms to which they are attached form a 5-membered heteroaryl moiety wherein —R3'—R2'— represents -A-CR6=B— or —B=CR6-A-; wherein:
A represents O, S or NR7; wherein R7 represents hydrogen, $C_1$-$C_8$ alkyl or alkyloxycarbonyl;
B represents CH or N; and
R6 represents hydrogen, hydroxy, halo, amino, alkylsulfonyl, aminosulfonyl, cyano, nitro, carboxy, aryl, alkoxy, haloalkyl, alkylamino, aminoalkyl, nitrooxyalkyl or carboxyalkyl.

According to a preferred embodiment, the inhibitors of the invention are compounds formula (II)

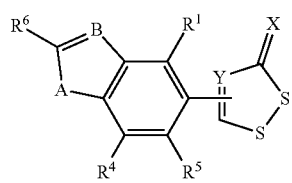
(II)

or a pharmaceutically acceptable tautomer, salt or solvate thereof, wherein X, Y, R1, R4, R5, R6, A and B are as defined in formula (I).

According to one embodiment, in formula (II):
X represents S, O or NHOH; preferably X is S;
Y represents CH, C or N; preferably Y is CH;
A represents O, S or NR7; wherein R7 represents hydrogen or $C_1$-$C_8$ alkyl group;
B represent CH or N;
R1, R4 and R5 each independently represent hydrogen, hydroxy, halo, amino, alkylsulfonyl, aminosulfonyl, cyano, nitro, carboxy, aryl, alkoxy, haloalkyl, alkylamino, aminoalkyl, nitrooxyalkyl or carboxyalkyl;
R6 represents hydrogen, hydroxy, halo, amino, alkylsulfonyl, aminosulfonyl, cyano, nitro, carboxy, aryl, alkoxy, haloalkyl, alkylamino, aminoalkyl, nitrooxyalkyl or carboxyalkyl.

According to a preferred embodiment, compounds of formula (II) are of formulae (IIa) or (IIb)

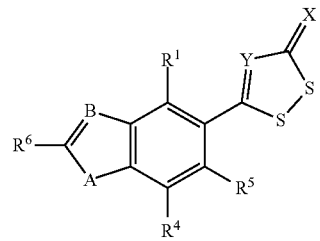
(IIa)

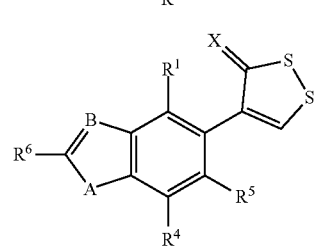
(IIb)

or a pharmaceutically acceptable tautomer, salt or solvate thereof, wherein X, Y, A, B, R1, R4, R5 and R6 are as defined above.

In a preferred embodiment, the inhibitors of the invention are of formula (IIa).

According to a preferred embodiment, compounds of formula (IIa) are of formulae (IIa-1) or (IIa-2)

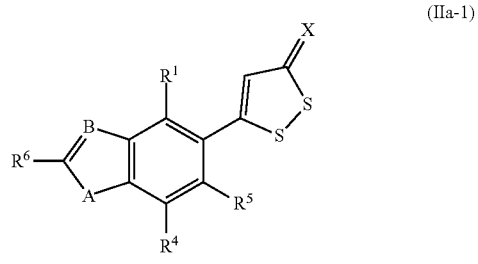
(IIa-1)

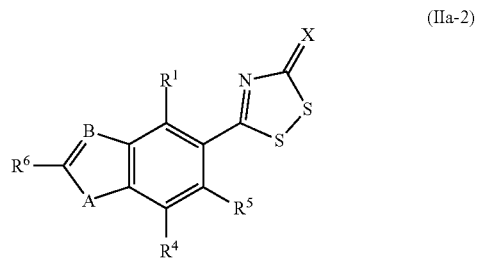
(IIa-2)

or a pharmaceutically acceptable tautomer, salt or solvate thereof, wherein X, A, B, R1, R4, R5 and R6 are as defined above.

In a preferred embodiment, the inhibitors of the invention are of formula (IIa-1). In another preferred embodiment, the inhibitors of the invention are of formula (IIa-2).

According to a preferred embodiment, compounds of formula (IIa-1) are of formulae (IIa-1'), (IIa-1") or (IIa-1''')

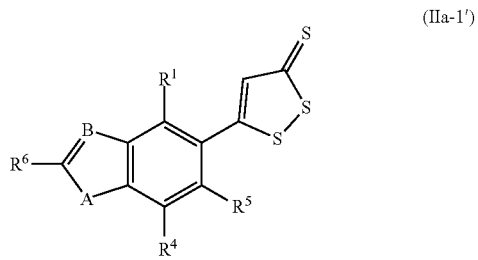
(IIa-1')

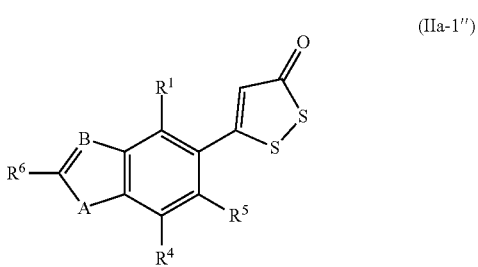
(IIa-1")

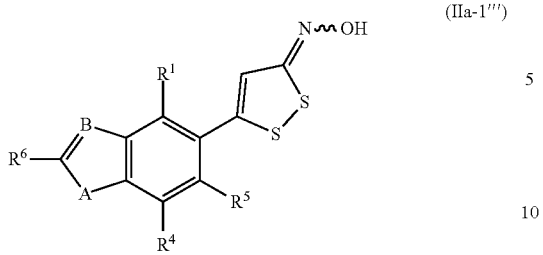
(IIa-1''')

or a pharmaceutically acceptable tautomer, salt or solvate thereof, wherein A, B, $R^1$, $R^4$, $R^5$ and $R^6$ are as defined above.

In a preferred embodiment, the inhibitors of the invention are of formula (IIa-1') or (IIa-1''), more preferably of formula (IIa-1').

According to a preferred embodiment, compounds of formula (IIa-2) are of formulae (IIa-2'), (IIa-2'') or (IIa-2''')

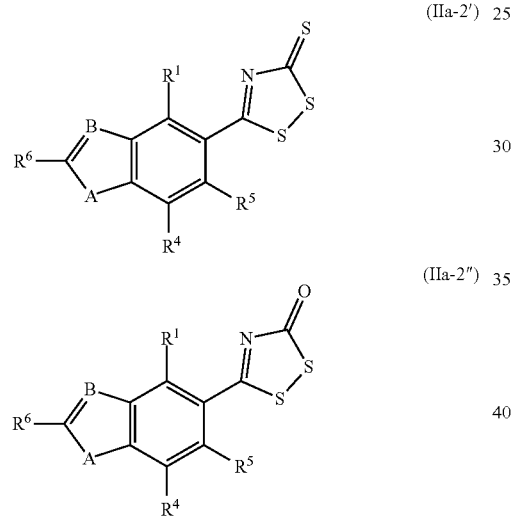
(IIa-2')
(IIa-2'')
(IIa-2''')

or a pharmaceutically acceptable tautomer, salt or solvate thereof, wherein A, B, $R^1$, $R^4$, $R^5$ and $R^6$ are as defined above.

In a preferred embodiment, the inhibitors of the invention are of formula (IIa-2') or (IIa-2'').

According to a preferred embodiment, compounds of formula (IIa-1) and (IIa-2) are of formulae (IIa-1a), (IIa-1b), (IIa-1c), (IIa-1d), (IIa-1e), (IIa-2a), (IIa-2b), (IIa-2c), (IIa-2d) or (IIa-2e)

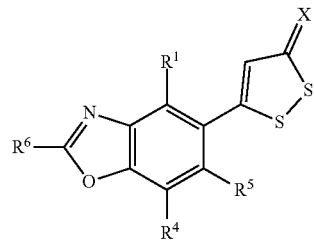
(IIa-1a)

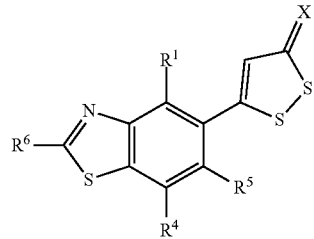
(IIa-1b)

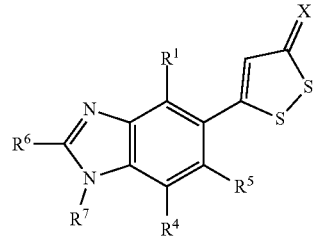
(IIa-1c)

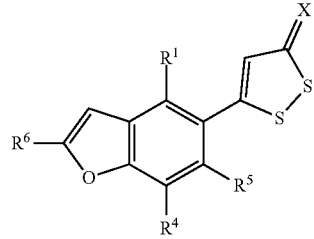
(IIa-1d)

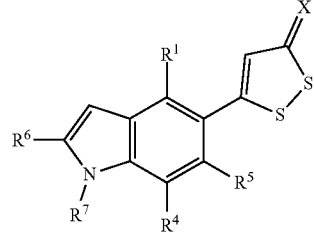
(IIa-1e)

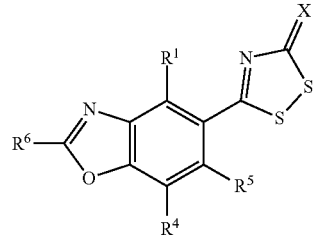
(IIa-2a)

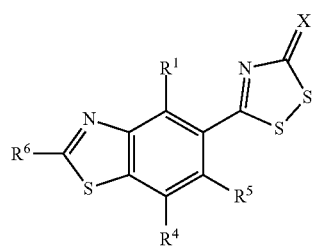
(IIa-2b)

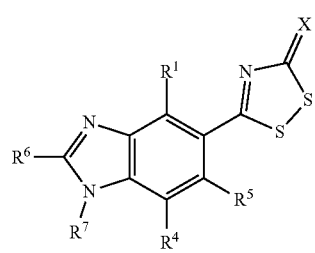
(IIa-2c)

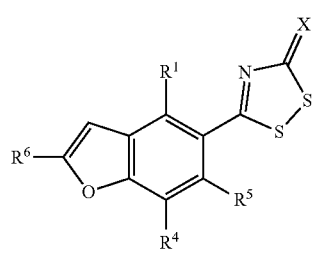
(IIa-2d)

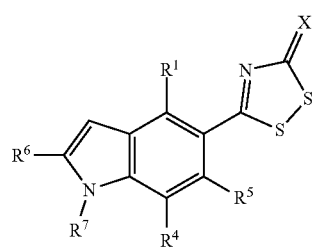
(IIa-2e)

or a pharmaceutically acceptable tautomer, salt or solvate thereof, wherein X, $R^1$, $R^4$, $R^5$, $R^6$ and $R^7$ are as defined above.

In a preferred embodiment, the inhibitors of the invention are of formula (IIa-1a), (IIa-1b), (IIa-1e), (IIa-2a), (IIa-2b) or (IIa-2e), more preferably of formula (IIa-1a) or (IIa-1e); more preferably of formula (IIa-1a).

According to a preferred embodiment, compounds of formula (IIb) are of formulae (IIb'), (IIb''), and (IIb''')

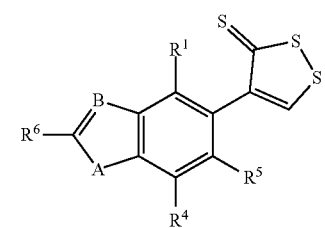
(IIb')

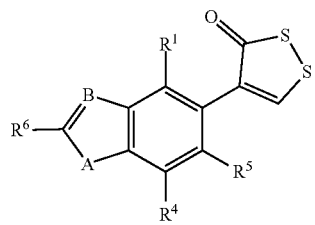
(IIb'')

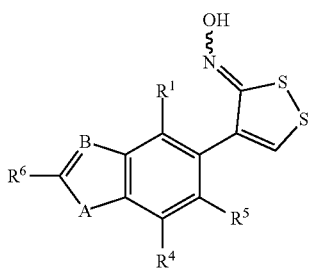
(IIb''')

or a pharmaceutically acceptable tautomer, salt or solvate thereof, wherein A, B, $R^1$, $R^4$, $R^5$ and $R^6$ are as defined above.

According to a preferred embodiment, compounds of formula (IIb) are of formulae (IIb-1), (IIb-2), IIb-3), (IIb-4) or (IIb-5)

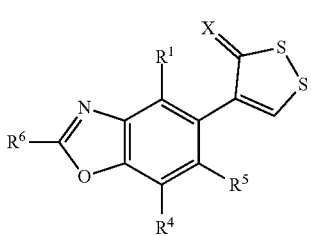
(IIb-1)

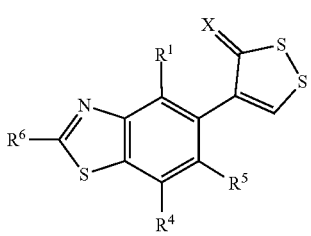
(IIb-2)

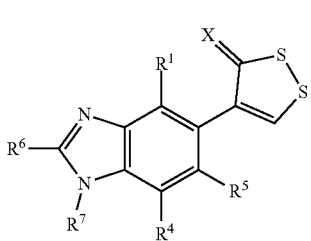
(IIb-3)

-continued

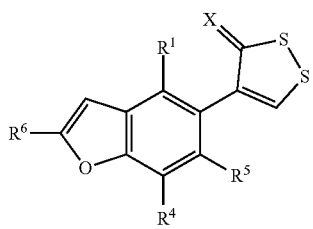
(IIb-4)

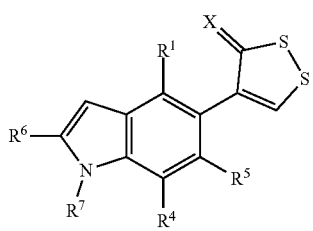
(IIb-5)

or a pharmaceutically acceptable tautomer, salt or solvate thereof, wherein X, $R^1$, $R^4$, $R^5$, $R^6$ and $R^7$ are as defined above.

According to a preferred embodiment, the inhibitors of the invention are compounds formula (III)

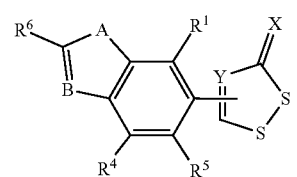
(III)

or a pharmaceutically acceptable tautomer, salt or solvate thereof, wherein X, Y, $R^1$, $R^4$, $R^5$, $R^6$, A and B are as defined in formula (I).

According to a preferred embodiment, compounds of formula (III) are of formulae (IIIa) or (IIIb)

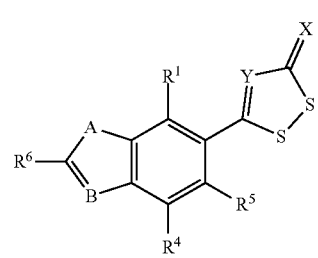
(IIIa)

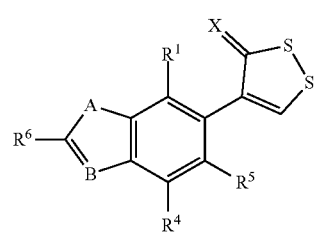
(IIIb)

or a pharmaceutically acceptable tautomer, salt or solvate thereof, wherein X, Y, A, B, $R^1$, $R^4$, $R^5$ and $R^6$ are as defined above.

In a preferred embodiment, the inhibitors of the invention are of formula (IIIa).

According to a preferred embodiment, compounds of formula (IIIa) are of formulae (IIIa-1) or (IIIa-2)

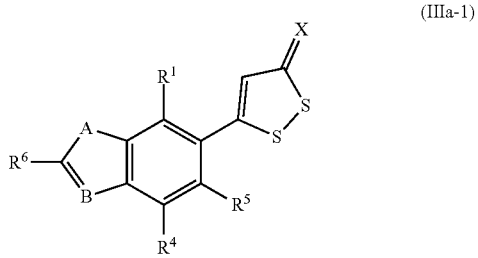
(IIIa-1)

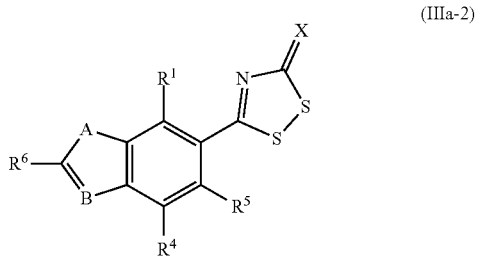
(IIIa-2)

or a pharmaceutically acceptable tautomer, salt or solvate thereof, wherein X, A, B, $R^1$, $R^4$, $R^5$ and $R^6$ are as defined above.

In a preferred embodiment, the inhibitors of the invention are of formula (IIIa-1). In another preferred embodiment, the inhibitors of the invention are of formula (IIIa-2).

According to a preferred embodiment, compounds of formula (IIIa-1) are of formulae (IIIa-1'), (IIIa-1") or (IIIa-1''')

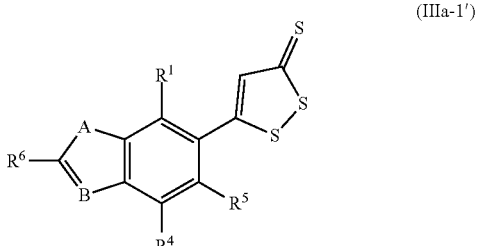
(IIIa-1')

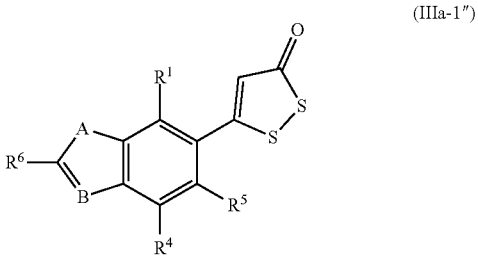
(IIIa-1")

(IIIa-1''')

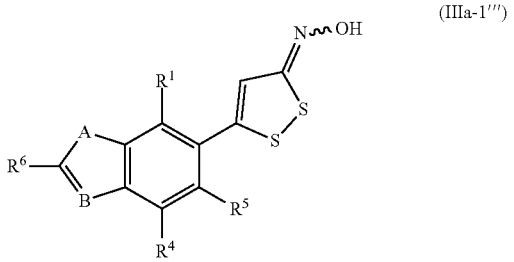

or a pharmaceutically acceptable tautomer, salt or solvate thereof, wherein A, B, $R^1$, $R^4$, $R^5$ and $R^6$ are as defined above.

In a preferred embodiment, the inhibitors of the invention are of formula (IIIa-1') or (IIIa-1''), more preferably of formula (IIIa-1').

According to a preferred embodiment, compounds of formula (IIIa-2) are of formulae (IIIa-2'), (IIIa-2'') or (IIIa-2''')

(IIIa-2')

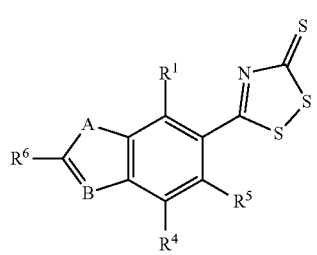

(IIIa-2'')

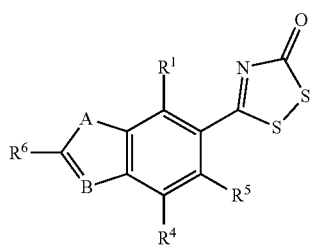

(IIIa-2''')

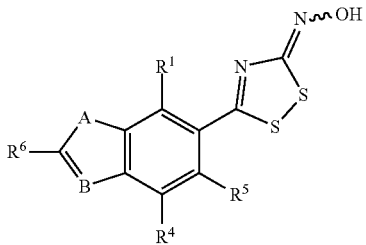

or a pharmaceutically acceptable tautomer, salt or solvate thereof, wherein A, B, $R^1$, $R^4$, $R^5$ and $R^6$ are as defined above.

In a preferred embodiment, the inhibitors of the invention are of formula (IIIa-2') or (IIIa-2'').

According to a preferred embodiment, compounds of formula (IIIa-1) and (IIIa-2) are of formulae (IIIa-1a), (IIIa-1b), (IIIa-1c), (IIIa-1d), (IIIa-1e), (IIIa-2a), (IIIa-2b), (IIIa-2c), (IIIa-2d) or (IIIa-2e)

(IIIa-1a)

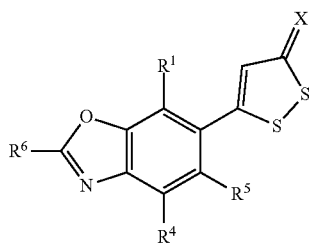

(IIIa-1b)

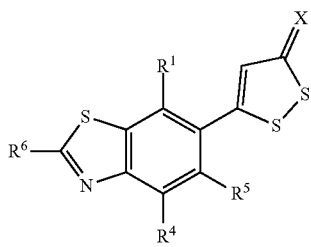

(IIIa-1c)

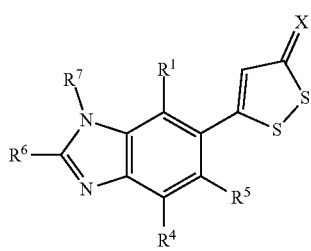

(IIIa-1d)

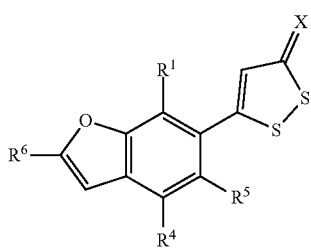

(IIIa-1e)

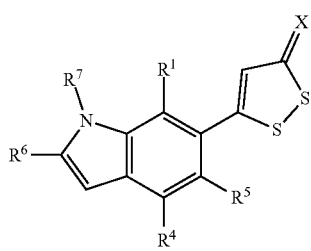

(IIIa-2a)

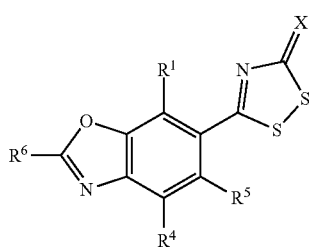

-continued (IIIa-2b)
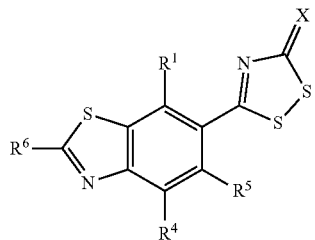

(IIIa-2c)
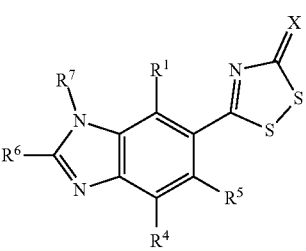

(IIIa-2d)
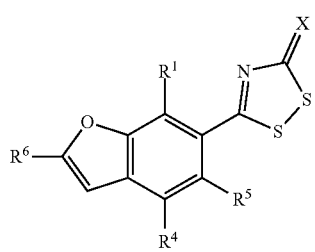

(IIIa-2e)
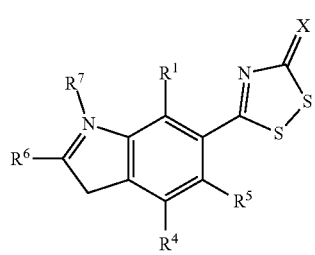

or a pharmaceutically acceptable tautomer, salt or solvate thereof, wherein X, $R^1$, $R^4$, $R^5$, $R^6$ and $R^7$ are as defined above.

In a preferred embodiment, the inhibitors of the invention are of formula (IIIa-1a), (IIIa-1b), (IIIa-1e), (IIIa-2a), (IIIa-2b) or (IIIa-2e), more preferably of formula (IIIa-1b).

According to a preferred embodiment, compounds of formula (IIIb) are of formulae (IIIb'), (IIIb") and (IIIb''')

(IIIb')
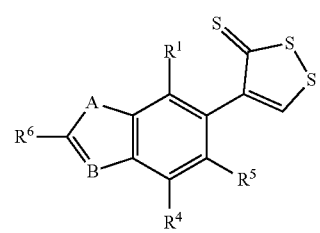

-continued (IIIb")
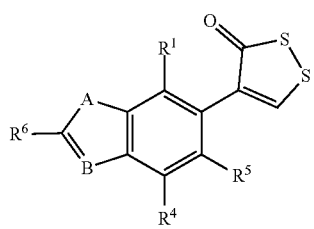

(IIIb''')
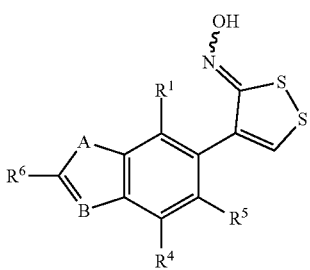

or a pharmaceutically acceptable tautomer, salt or solvate thereof, wherein A, B, $R^1$, $R^4$, $R^5$ and $R^6$ are as defined above.

According to a preferred embodiment, compounds of formula (IIIb) are of formulae (IIIb-1), (IIIb-2), (IIIb-3), (IIIb-4) or (IIIb-5)

(IIIb-1)
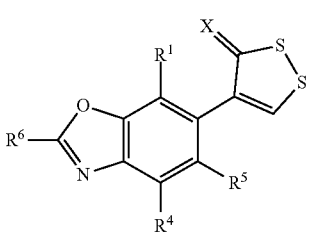

(IIIb-2)
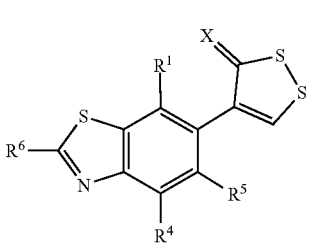

(IIIb-3)
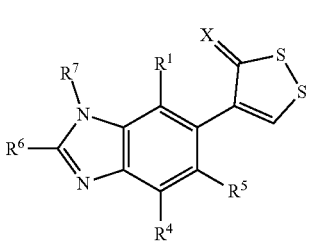

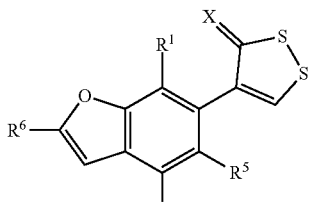

(IIIb-4)

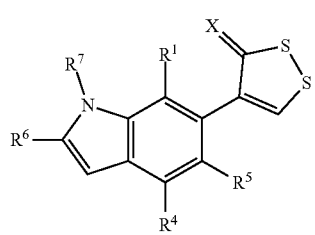

(IIIb-5)

or a pharmaceutically acceptable tautomer, salt or solvate thereof, wherein X, $R^1$, $R^4$, $R^5$, $R^6$ and $R^7$ are as defined above.

According to a specific embodiment, the inhibitors of the invention are selected from:
5-(4-methoxyphenyl)-3H-1,2-dithiole-3-thione (AOL);
5-(4-hydroxyphenyl)-3H-1,2-dithiole-3-thione (AOX);
5-(4-hydroxyphenyl)-3H-1,2-dithiol-3-one (Cp1);
5-(4-hydroxyphenyl)-3H-1,2-dithiol-3-one oxime (Cp2);
5-(4-hydroxyphenyl)-3H-1,2,4-dithiazole-3-thione (Cp3);
4-(4-hydroxyphenyl)-3H-1,2-dithiole-3-thione (Cp4);
5-(2-hydroxybenzo[d]oxazol-5-yl)-3H-1,2-dithiole-3-thione (Cp5);
5-(2-hydroxybenzo[d]thiazol-6-yl)-3H-1,2-dithiole-3-thione (Cp6a);
5-(benzofuran-5-yl)-3H-1,2-dithiole-3-thione (Cp8); and
methyl 5-(3-thioxo-3H-1,2-dithiol-5-yl)-1H-indole-1-carboxylate (Cp9a).

According to a preferred embodiment, the inhibitors of the invention are selected from AOL, AOX, Cp1, Cp3, Cp4, Cp5, Cp6a and Cp9a. According to a preferred embodiment, the inhibitors of the invention are selected from AOL, AOX, Cp1, Cp3, Cp5 and Cp6a.

According to a preferred embodiment, the inhibitor of the invention is selected from AOL and AOX.

According to a preferred embodiment, the inhibitor of the invention is AOL.

According to a preferred embodiment, the inhibitor of the invention is AOX. According to a preferred embodiment, the inhibitor of the invention is Cp1. According to a preferred embodiment, the inhibitor of the invention is Cp3. According to a preferred embodiment, the inhibitor of the invention is Cp5. According to a preferred embodiment, the inhibitor of the invention is Cp6a.

Solubilization Vehicle

The inhibitors of mitochondrial production of reactive oxygen species (ROS) are advantageous as they selectively inhibit the mitochondrial production of reactive oxygen species (ROS) by acting on at least one site selected from $I_Q$, $I_F$ and SDH of the mitochondrion.

Nevertheless, their therapeutic potential is hindered by their limited aqueous solubility.

The Applicant has screened several solubilization vehicles in view of improving the aqueous solubility of the previously described inhibitors, and found that cyclodextrins are particularly advantageous.

According to a first embodiment, the solubilization vehicle is thus a cyclodextrin.

In one embodiment, the cyclodextrin is an α-cyclodextrin. In one embodiment, the cyclodextrin is a γ-cyclodextrin. In a preferred embodiment, the cyclodextrin is a β-cyclodextrin.

According to a first embodiment, the cyclodextrin is a cyclodextrin of formula (IV)

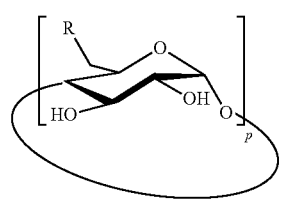

(IV)

wherein:
p is 6, 7 or 8;
R is —OH, 2-hydroxypropyl or —$R_{1'}$—$SO_3Na$;
$R_{1'}$ is selected from, short chain alkyls preferably selected from methyl, ethyl, propyl and butyl, even more preferably $R_{1'}$ is butyl;

In one embodiment, the cyclodextrin can be α-cyclodextrin, β-cyclodextrins or γ-cyclodextrin. In such embodiment, p is 6, 7 or 8 respectively. Preferably, the cyclodextrin is a β-cyclodextrin, wherein p=7.

In one preferred embodiment, the cyclodextrin is a cyclodextrin of formula (IV), with the proviso that at least one R is not OH.

According to a first embodiment, the cyclodextrin is a mono-substituted cyclodextrin of formula (IV) bearing one R=2-hydroxypropyl or —$R_{1'}$—$SO_3Na$. The average molar substitution of such cyclodextrin ranges from 0.5 to 1.5, preferably from 0.6 to 1.

According to a second embodiment, the cyclodextrin is a bi-substituted cyclodextrin of formula (IV) bearing two R=2-hydroxypropyl or —$R_{1'}$—$SO_3Na$. The average molar substitution of such cyclodextrin ranges from 1.6 to 2.5, preferably from 1.7 to 2.5.

According to a third embodiment, the cyclodextrin is a tri-substituted cyclodextrin of formula (IV) bearing three R=2-hydroxypropyl or —$R_{1'}$—$SO_3Na$. The average molar substitution of such cyclodextrin ranging from 2.6 to 3.5, preferably from 2.7 to 3.5.

In further embodiments, the cyclodextrin is a pluri-substituted cyclodextrin bearing at least four, five or six R=2-hydroxypropyl or —$R_{1'}$—$SO_3Na$.

In one embodiment, the cyclodextrin is a cyclodextrin of formula (IV) wherein p=6, 7 or 8 and at least one R=2-hydroxypropyl.

In a preferred embodiment, the cyclodextrin is a cyclodextrin of formula (IV) wherein p=7 and at least one R=2-hydroxypropyl (hydroxypropyl-β-cyclodextrin, HP-β-CD). In one embodiment, the molar substitution ratio of hydroxypropyl-β-cyclodextrin ranges from 0.4 to 1.5, from 0.6 to 1, from 0.6 to 0.95, from 0.6 to 0.7 or from 0.8 to 0.9. In one embodiment, the average degree of substitution (n) of the hydroxypropyl-β-cyclodextrin ranges from 3 to 5.4.

In another embodiment, the cyclodextrin is hydroxypropyl-α-cyclodextrin. In another embodiment, the cyclodextrin is hydroxypropyl-γ-cyclodextrin.

In one embodiment, the cyclodextrin is a cyclodextrin of formula (IV) wherein p=6, 7 or 8 and at least one R═—$R_1$—$SO_3Na$, $R_{1'}$ being as previously described. In one embodiment, the molar substitution ratio of such cyclodextrin ranges from 0.4 to 5.5, from 0.6 to 4.5 or from 0.6 to 3.5.

In one embodiment, the cyclodextrin is a cyclodextrin of formula (IV) wherein p=7 or 8 and at least one R═—$R_1$—$SO_3Na$. In one embodiment, the molar substitution ratio of such cyclodextrin ranges from 0.4 to 5.5, from 0.6 to 4.5 or from 0.6 to 3.5.

In a preferred embodiment, the cyclodextrin is a cyclodextrin of formula (IV) wherein p=7 and at least one R═—$R_1$—$SO_3Na$ (sulfobutylether-β-cyclodextrin, SBE-β-CD). In one embodiment, the molar substitution ratio of the hydroxypropyl-β-cyclodextrin ranges from 0.4 to 1.5, from 0.6 to 1, from 0.6 to 0.95, from 0.6 to 0.7 or from 0.8 to 0.9.

In one embodiment, the average degree of substitution (n) of the sulfobutylether-β-cyclodextrin ranges from 3.5 to 4.5 or from 6.2 to 6.9.

In another embodiment, the cyclodextrin is sulfobutylether-α-cyclodextrin. In another embodiment, the cyclodextrin is sulfobutylether-γ-cyclodextrin.

In another aspect, the solubilization vehicle may be whichever micro- or macro-molecular chemical entity bearing at least one hydroxypropyl or sulfobutylether moiety.

The Applicant surprisingly found that the molar ratio of the solubilization vehicle to the inhibitor of mitochondrial production of reactive oxygen species (ROS) is of particular interest. In the molar ratios of the invention, the inhibitor presents an advantageous aqueous solubility, is chemically stable while the obtained aqueous solution presents an advantageous viscosity.

In one embodiment, the molar ratio of the solubilization vehicle to the inhibitor is superior to 2, superior to 2.5, preferably superior to 10, even more preferably superior to 30.

In one embodiment, the molar ratio of the solubilization vehicle to the inhibitor ranges from 2.5 to 400. In one embodiment, the molar ratio of the solubilization vehicle to the inhibitor ranges from 5 to 400. In one embodiment, the molar ratio of the solubilization vehicle to the inhibitor ranges from 10 to 400. In one embodiment, the molar ratio of the solubilization vehicle to the inhibitor ranges from 20 to 400. In one embodiment, the molar ratio of the solubilization vehicle to the inhibitor ranges from 30 to 400. In one embodiment, the molar ratio of the solubilization vehicle to the inhibitor ranges from 40 to 400.

In one embodiment, the molar ratio of the solubilization vehicle to the inhibitor is more than 50. In one embodiment, the molar ratio of the solubilization vehicle to the inhibitor is more than 52. In one embodiment, the molar ratio of the solubilization vehicle to the inhibitor is more than 54. In one embodiment, the molar ratio of the solubilization vehicle to the inhibitor is more than 55. In one embodiment, the molar ratio of the solubilization vehicle to the inhibitor is more than 56.

In one embodiment, the molar ratio of the solubilization vehicle to the inhibitor is more than 57. In one embodiment, the molar ratio of the solubilization vehicle to the inhibitor is more than 58. In one embodiment, the molar ratio of the solubilization vehicle to the inhibitor is more than 59. In one embodiment, the molar ratio of the solubilization vehicle to the inhibitor is more than 60.

In one embodiment, the molar ratio of the solubilization vehicle to the inhibitor ranges from 53 to 400. In one embodiment, the molar ratio of the solubilization vehicle to the inhibitor ranges from 54 to 400. In one embodiment, the molar ratio of the solubilization vehicle to the inhibitor ranges from 55 to 400. In one embodiment, the molar ratio of the solubilization vehicle to the inhibitor ranges from 56 to 400. In one embodiment, the molar ratio of the solubilization vehicle to the inhibitor ranges from 57 to 400. In one embodiment, the molar ratio of the solubilization vehicle to the inhibitor ranges from 58 to 400. In one embodiment, the molar ratio of the solubilization vehicle to the inhibitor ranges from 59 to 400. In one embodiment, the molar ratio of the solubilization vehicle to the inhibitor ranges from 60 to 400. In one embodiment, the molar ratio of the solubilization vehicle to the inhibitor ranges from 65 to 400.

In one embodiment, the molar ratio of the solubilization vehicle to the inhibitor ranges from 2.5 to 200. In one embodiment, the molar ratio of the solubilization vehicle to the inhibitor ranges from 5 to 200. In one embodiment, the molar ratio of the solubilization vehicle to the inhibitor ranges from 10 to 200. In one embodiment, the molar ratio of the solubilization vehicle to the inhibitor ranges from 20 to 200. In one embodiment, the molar ratio of the solubilization vehicle to the inhibitor ranges from 30 to 200. In one embodiment, the molar ratio of the solubilization vehicle to the inhibitor ranges from 40 to 200.

In one embodiment, the molar ratio of the solubilization vehicle to the inhibitor ranges from 53 to 200. In one embodiment, the molar ratio of the solubilization vehicle to the inhibitor ranges from 54 to 200. In one embodiment, the molar ratio of the solubilization vehicle to the inhibitor ranges from 55 to 200. In one embodiment, the molar ratio of the solubilization vehicle to the inhibitor ranges from 56 to 200. In one embodiment, the molar ratio of the solubilization vehicle to the inhibitor ranges from 57 to 200. In one embodiment, the molar ratio of the solubilization vehicle to the inhibitor ranges from 58 to 200. In one embodiment, the molar ratio of the solubilization vehicle to the inhibitor ranges from 59 to 200. In one embodiment, the molar ratio of the solubilization vehicle to the inhibitor ranges from 60 to 200. In one embodiment, the molar ratio of the solubilization vehicle to the inhibitor ranges from 65 to 200.

In one embodiment, the molar ratio of the cyclodextrin of formula (IV) to the compound of formula (I) ranges from 2.5 to 400. In one embodiment, the molar ratio of the cyclodextrin of formula (IV) to the compound of formula (I) ranges from 5 to 400. In one embodiment, the molar ratio of the cyclodextrin of formula (IV) to the compound of formula (I) ranges from 10 to 400. In one embodiment, the molar ratio of the cyclodextrin of formula (IV) to the compound of formula (I) ranges from 20 to 400. In one embodiment, the molar ratio of the cyclodextrin of formula (IV) to the compound of formula (I) ranges from 30 to 400. In one embodiment, the molar ratio of the cyclodextrin of formula (IV) to the compound of formula (I) ranges from 40 to 400. In one embodiment, the molar ratio of the cyclodextrin of formula (IV) to the compound of formula (I) ranges from 10 to 200. In one embodiment, the molar ratio of the cyclodextrin of formula (IV) to the compound of formula (I) ranges from 30 to 200. In one embodiment, the molar ratio of the cyclodextrin of formula (IV) to the inhibitor ranges from 50 to 200. In one embodiment, the molar ratio of the cyclodextrin of formula (IV) to the inhibitor ranges from 51 to 200. In one embodiment, the molar ratio of the cyclodextrin of formula (IV) to the inhibitor ranges from 52 to 200. In one embodiment, the molar ratio of the cyclodextrin of formula (IV) to the inhibitor ranges from 53 to 200. In one embodiment, the molar ratio of the cyclodextrin of formula (IV) to the inhibitor ranges from 54 to 200. In one embodiment, the molar ratio of the cyclodextrin of formula (IV) to the inhibitor ranges from 55 to 200. In one embodiment, the molar ratio of the cyclodextrin of formula (IV) to the inhibitor ranges from 56 to 200. In one embodiment, the molar ratio of the cyclodextrin of formula (IV) to the inhibitor ranges from 57 to 200. In one embodiment, the molar ratio of the cyclodextrin of formula (IV) to the inhibitor ranges from 58 to 200. In one embodiment, the molar ratio of the cyclodextrin of formula (IV) to the inhibitor ranges from 59 to 200.

In one embodiment, the molar ratio of the cyclodextrin of formula (IV) to the inhibitor ranges from 60 to 200. In one embodiment, the molar ratio of the cyclodextrin of formula (IV) to the inhibitor ranges from 65 to 200.

In one embodiment, the molar ratio of the hydroxypropyl-β-cyclodextrin to the compound of formula (I) ranges from 60 to 300. In one embodiment, the molar ratio of the hydroxypropyl-β-cyclodextrin to the compound of formula (I) ranges from 60 to 250. In one embodiment, the molar ratio of the hydroxypropyl-β-cyclodextrin to the compound of formula (I) ranges from 70 to 250. In one embodiment, the molar ratio of the hydroxypropyl-β-cyclodextrin to the compound of formula (I) ranges from 100 to 250. In one embodiment, the molar ratio of the hydroxypropyl-β-cyclodextrin to the compound of formula (I) ranges from 65 to 230. In one embodiment, the molar ratio of the hydroxypropyl-β-cyclodextrin to the compound of formula (I) ranges from 60 to 150.

In one embodiment, the molar ratio of the sulfobutylether-β-cyclodextrin to the compound of formula (I) ranges from 2.5 to 400, preferably from 10 to 400, more preferably from 30 to 200, more preferably from 57 to 200.

In one embodiment, the molar ratio of the sulfobutylether-β-cyclodextrin to the compound of formula (I) ranges from 40 to 160. In one embodiment, the molar ratio of the sulfobutylether-β-cyclodextrin to the compound of formula (I) ranges from 40 to 150. In one embodiment, the molar ratio of the sulfobutylether-β-cyclodextrin to the inhibitor ranges from 50 to 160. In one embodiment, the molar ratio of the sulfobutylether-β-cyclodextrin to the inhibitor ranges from 51 to 160. In one embodiment, the molar ratio of the sulfobutylether-β-cyclodextrin to the inhibitor ranges from 52 to 160. In one embodiment, the molar ratio of the sulfobutylether-β-cyclodextrin to the inhibitor ranges from 53 to 160. In one embodiment, the molar ratio of the sulfobutylether-β-cyclodextrin to the inhibitor ranges from 54 to 160. In one embodiment, the molar ratio of the sulfobutylether-β-cyclodextrin to the inhibitor ranges from 55 to 160. In one embodiment, the molar ratio of the sulfobutylether-β-cyclodextrin to the inhibitor ranges from 56 to 160. In one embodiment, the molar ratio of the sulfobutylether-β-cyclodextrin to the inhibitor ranges from 57 to 160. In one embodiment, the molar ratio of the sulfobutylether-β-cyclodextrin to the inhibitor ranges from 58 to 160. In one embodiment, the molar ratio of the sulfobutylether-β-cyclodextrin to the inhibitor ranges from 59 to 160. In one embodiment, the molar ratio of the sulfobutylether-β-cyclodextrin to the inhibitor ranges from 60 to 160. In one embodiment, the molar ratio of the sulfobutylether-β-cyclodextrin to the inhibitor ranges from 65 to 160. In one embodiment, the molar ratio of the sulfobutylether-β-cyclodextrin to the compound of formula (I) ranges from 90 to 160.

In one embodiment, the molar ratio of the sulfobutylether-β-cyclodextrin to the inhibitor ranges from 50 to 150, preferably from 80 to 150.

In one embodiment, the molar ratio of the sulfobutylether-β-cyclodextrin to the inhibitor ranges from 50 to 120, or from 80 to 120.

In one embodiment, the molar ratio of the sulfobutylether-β-cyclodextrin to the inhibitor ranges from 80 to 120.

The following molar ratio ranges of the sulfobutylether-β-cyclodextrin or the hydroxypropyl-β-cyclodextrin to the compound of formula (I) are of particular interest. In fact, compositions of a compound of formula (I) in association with a sulfobutylether-β-cyclodextrin or a hydroxypropyl-β-cyclodextrin having the following ratios cyclodextrin: inhibitor ratios can lead to powder compositions whose reconstituted aqueous solutions comply with the guidelines relative to the permitted daily exposure to cyclodextrins (i.e., 300 mg/kg/day according the European Medicines Agency for the sulfobutylether-β-cyclodextrin or the hydroxypropyl-β-cyclodextrin; Loftsson & Brewster, 2010. *J Pharm Pharmacol.* 62(11):1607-21).

In one embodiment, the molar ratio of the hydroxypropyl-β-cyclodextrin to the compound of formula (I) ranges from 10 to 50. In one embodiment, the molar ratio of the hydroxypropyl-β-cyclodextrin to the compound of formula (I) ranges from 15 to 50. In one embodiment, the molar ratio of the hydroxypropyl-β-cyclodextrin to the compound of formula (I) ranges from 20 to 50. In one embodiment, the molar ratio of the hydroxypropyl-β-cyclodextrin to the compound of formula (I) ranges from 10 to 35. In one embodiment, the molar ratio of the hydroxypropyl-β-cyclodextrin to the compound of formula (I) is about 10, about 15, about 20, about 25 or about 35.

In one embodiment, the molar ratio of the sulfobutylether-β-cyclodextrin to the compound of formula (I) ranges from 55 to 150, from 56 to 150, from 57 to 150, from 58 to 150, preferably from 57 to 140.

In one embodiment, the molar ratio of the sulfobutylether-β-cyclodextrin to the compound of formula (I) is about 57, about 58, about 57, about 59, about 60, about 65.

In one embodiment, the molar ratio of the sulfobutylether-β-cyclodextrin to the compound of formula (I) is about 90, about 95, about 100, about 105, about 110, about 115, about 120, about 125, about 130, about 135, about 140 about 145, about 150, about 155, about 160 or about 165.

In one embodiment, the weight ratio of the sulfobutylether-β-cyclodextrin to the compound of formula (I) ranges from 400 to 2000, from 500 to 2000, from 800 to 1500, from 900 to 1200, from 900 to 1100. In one embodiment, the weight ratio of the sulfobutylether-β-cyclodextrin to the compound of formula (I) is about 500, about 600, about 700, about 800, about 900, about 1000 or about 1100.

Given, the restrictions by the guidelines relative to the permitted daily exposure to solubilization vehicles such as cyclodextrins, the amount of such solubilization vehicles does not exceed 60% (w/w) in the inventions compositions. In one embodiment, the amount of such solubilization vehicles does not exceed 40% (w/w) in the inventions compositions.

In one embodiment, the amount of the hydroxypropyl-β-cyclodextrin ranges from 1 to 40% (w/w), preferably 2.5 to 30% (w/w), even more preferably from 5 to 20% (w/w), in weight relative to the total weight of the composition.

In one embodiment, the amount of the sulfobutylether-β-cyclodextrin ranges from 1 to 40% (w/w), preferably 2.5 to 30% (w/w), even more preferably from 5 to 20% (w/w), in weight relative to the total weight of the composition. In one embodiment, the amount of the sulfobutylether-β-cyclodextrin is about 2.5, about 5, about 10, about 15, about 20, about 25, about 30, about 35 or about to 40% (w/w), in weight relative to the total weight of the composition.

In one embodiment, the amount of the sulfobutylether-β-cyclodextrin is about 5 or about 10% (w/w), in weight relative to the total weight of the composition.

In one embodiment, the amount of the sulfobutylether-β-cyclodextrin ranges from 10 to 600 mg/mL. In one embodiment, the amount of the sulfobutylether-β-cyclodextrin ranges from 40 to 600 mg/mL. In one embodiment, the amount of the sulfobutylether-β-cyclodextrin ranges from 60 to 400 mg/mL. In one embodiment, the amount of the sulfobutylether-β-cyclodextrin ranges from 80 to 400 mg/mL. In one embodiment, the amount of the sulfobutylether-β-cyclodextrin ranges from 100 to 400 mg/mL.

The concentration of the composition to be further processed by spray-drying or freeze-drying (lyophilized) preferably comprises sulfobutylether-β-cyclodextrin in amount ranging from 60 to 150 mg/mL. In one embodiment, the amount of the sulfobutylether-O-cyclodextrin ranges from 80 to 150 mg/mL. In one embodiment, the amount of the sulfobutylether-β-cyclodextrin is about 80, 90, 100, 110, 120, 130, 140 or 150 mg/mL.

Excipients

The composition of the invention may further comprise at least one excipient, preferably a pharmaceutically acceptable excipient.

In one embodiment, the excipient is selected from a list consisting of co-solvents, buffers, saline, Ringer's solution, dextrose solution, and solutions of ethanol, glucose, sucrose, dextran, mannose, mannitol, sorbitol, gelatin, collagen, Carbopol®, vegetable oils, and the like. The composition may additionally include suitable preservatives, stabilizers, antioxidants, antimicrobials, and buffering agents, such as, e.g., BHA, BHT, citric acid, ascorbic acid, tetracycline, and the like. In one embodiment, the composition further comprises at least one osmotic pressure regulating excipient such as for example sucrose or mannitol.

In one embodiment, the composition comprises a buffer selected from citrate buffer, tris(hydroxymethyl)aminomethane (Tris) buffer, 4-(2-hydroxyethyl)-1-piperazine ethanesulfonic acid (HEPES) buffer, ammonium sulfate, carbonate or acetate buffer.

In one embodiment, the composition comprises a buffer selected from citrate buffer, acetate buffer, tris or phosphate buffer. In one embodiment, the composition comprises a buffer selected from Tris or phosphate buffer.

In one embodiment, the composition comprises a buffer, preferably a phosphate buffer in an amount ranging from 10 to 150 mM, from 10 to 140 mM, from 25 to 140 mM, from 15 to 35 mM or from 60 to 140 mM.

In one embodiment, the aqueous composition does not comprise a buffer.

In one embodiment, the aqueous composition does not comprise a phosphate buffer.

In one embodiment, the pH of the aqueous solution ranges from 5 to 8, from 5.5 to 7.8, from 6 to 7.8 or from 6.5 to 7.5. In one embodiment, the pH of the aqueous solution is about 5.0, about 5.5, about 5.8, about 6.0, about 6.2, about 6.5, about 6.8, about 7.0, about 7.2, about 7.4, about 7.5, about 7.6, or about 7.8.

Other examples of pharmaceutically acceptable excipients that may be used in the composition of the invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, sodium carboxymethylcellulose, polyacrylates, waxes, polyethylene-polyoxypropylene-block polymers, polyethylene glycol and wool fat.

In addition some excipients may include, surfactants (e.g., hydroxypropylcellulose); suitable carriers, such as, e.g., solvents and dispersion media containing, e.g., water, ethanol, polyol (e.g., glycerol, propylene glycol, and liquid polyethylene glycol, and the like), suitable mixtures thereof, and vegetable oils, such as, e.g., peanut oil and sesame oil; isotonic agents, such as, e.g., sugars or sodium chloride; coating agents, such as, e.g., lecithin; agents delaying absorption, such as, e.g., aluminum monostearate and gelatin; preservatives, such as, e.g., benzalkonium chloride, benzethonium chloride, chlorobutanol, thimerosal and the like; buffers, such as, e.g., boric acid, sodium and potassium bicarbonate, sodium and potassium borates, sodium and potassium carbonate, sodium acetate, sodium biphosphate and the like; tonicity agents, such as, e.g., dextran 40, dextran 70, dextrose, glycerin, potassium chloride, propylene glycol, sodium chloride; antioxidants and stabilizers, such as, e.g., sodium bisulfite, sodium metabisulfite, sodium thiosulfite, thiourea and the like; nonionic wetting or clarifying agents, such as, e.g., polysorbate 80, polysorbate 20, poloxamer 282 and tyloxapol; viscosity modifying agents, such as, e.g., dextran 40, dextran 70, gelatin, glycerin, hydroxyethylcellulose, hydroxymethylpropylcellulose, lanolin, methylcellulose, petrolatum, polyethylene glycol, polyvinyl alcohol, polyvinylpyrrolidone, carboxymethylcellulose; and the like.

In view of obtaining concentrated compound of formula (I) within aqueous and not highly-viscous compositions, the composition of the invention may further comprise at least one excipient.

In one embodiment, the at least one pharmaceutically acceptable excipient is a co-solvent.

In one embodiment, at least one co-solvent is selected from a group consisting of polysorbates, propylene glycol, glycerin, paraffin oil, alpha-tocopherol, dimethyl sulfoxide, N-methyl-2-pyrrolidone, glycofurol, Solketal, glycerol formal, acetone, ethanol, tetrahydrofurfuryl alcohol, diglyme, dimethylacetamide, dimethyl isosorbide, ethyl lactate, Cremophor EL, Cremophor RH 40, Cremophor RH 60, Solutol HS 15, poloxamer 407, Labrasol, Gellucire 44/14, Softigen 767, mono- and di-fatty acid esters mono- and di-fatty acid esters of PEG 200, PEG 300, PEG 400, PEG 600, PEG 1750, PEG 2000 to 20000, PEG 1000 succinate; hydrogenated soy phosphatidylcholine, distearoylphosphatidylglycerol, L-α-dimyristoylphosphatidylcholine and L-α-dimyristoyl-phosphatidylglycerol.

In one embodiment, at least one co-solvent is selected from a group consisting of polysorbates, propylene glycol, glycerin, paraffin oil, alpha-tocopherol, dimethyl sulfoxide, N-methyl-2-pyrrolidone, glycofurol, Solketal, glycerol formal, acetone, ethanol, tetrahydrofurfuryl alcohol, diglyme, dimethylacetamide, dimethyl isosorbide, ethyl lactate, Cremophor RH 40, Cremophor RH 60, Solutol HS 15, poloxamer 407, Labrasol, Gellucire 44/14, Softigen 767, mono- and di-fatty acid esters mono- and di-fatty acid esters of PEG 200, PEG 300, PEG 400, PEG 600, PEG 1750, PEG 2000 to 20000, PEG 1000 succinate; hydrogenated soy phosphatidylcholine, distearoylphosphatidylglycerol, L-α-dimyristoylphosphatidylcholine and L-α-dimyristoyl-phosphatidylglycerol.

In one embodiment, at least one co-solvent is selected from a group consisting of polysorbates, propylene glycol, glycerin, paraffin oil, alpha-tocopherol, dimethyl sulfoxide, N-methyl-2-pyrrolidone, glycofurol, Solketal, glycerol formal, acetone, ethanol, tetrahydrofurfuryl alcohol, diglyme, dimethylacetamide, dimethyl isosorbide, ethyl lactate, Solutol HS 15, poloxamer 407, Labrasol, Gellucire 44/14, Softigen 767, mono- and di-fatty acid esters mono- and di-fatty acid esters of PEG 200, PEG 300, PEG 400, PEG 600, PEG 1750, PEG 2000 to 20000, PEG 1000 succinate; hydrogenated soy phosphatidylcholine, distearoylphosphatidylglycerol, L-α-dimyristoylphosphatidyl-choline and L-α-dimyristoyl-phosphatidylglycerol.

In one embodiment, at least one co-solvent is selected from a group consisting of polysorbates, propylene glycol, glycerin, paraffin oil, alpha-tocopherol, dimethyl sulfoxide, N-methyl-2-pyrrolidone, glycofurol, Solketal, glycerol formal, acetone, ethanol, tetrahydrofurfuryl alcohol, diglyme, dimethylacetamide, dimethyl isosorbide, ethyl lactate, poloxamer 407, Labrasol, Gellucire 44/14, Softigen 767, mono- and di-fatty acid esters mono- and di-fatty acid esters of PEG 200, PEG 300, PEG 400, PEG 600, PEG 1750, PEG 2000 to 20000, PEG 1000 succinate; hydrogenated soy phosphatidylcholine, distearoylphosphatidylglycerol, L-α-dimyristoylphosphatidylcholine and L-α-dimyristoyl-phosphatidylglycerol.

In one embodiment, at least one co-solvent is selected from a group consisting of polysorbates, propylene glycol, glycerin, paraffin oil, alpha-tocopherol, N-methyl-2-pyrrolidone, glycofurol, Solketal, glycerol formal, acetone, ethanol, tetrahydrofurfuryl alcohol, diglyme, dimethylacetamide, dimethyl isosorbide, ethyl lactate, poloxamer 407, Labrasol, Gellucire 44/14, Softigen 767, mono- and di-fatty acid esters mono- and di-fatty acid esters of PEG 200, PEG 300, PEG 400, PEG 600, PEG 1750, PEG 2000 to 20000, PEG 1000 succinate; hydrogenated soy phosphatidylcholine, distearoyl-phosphatidylglycerol, L-α-dimyristoylphosphatidylcholine and L-α-dimyristoyl-phosphatidylglycerol.

Polysorbates may be selected from polysorbate 80, polysorbate 20, polysorbate 40, polysorbate 60 or polysorbate 65. Preferably, the polysorbate is polysorbate 80, polysorbate 20 and mixtures thereof.

In one embodiment, the at least one co-solvent is selected from a group consisting of polysorbate 80, polysorbate 20, polysorbate 40, polysorbate 60 or polysorbate 65, propylene glycol, alpha-tocopherol, dimethyl sulfoxide, N-methyl-2-pyrrolidone, ethanol, tetrahydrofurfuryl alcohol, diglyme, dimethylacetamide, dimethyl isosorbide, polyethylene glycol 1000 succinate, poloxamer 407, mono- and di-fatty acid esters of PEG 300, 400, or 1750.

In one embodiment, the at least one co-solvent is selected from a group consisting of polysorbate 80, polysorbate 20, polysorbate 40, polysorbate 60 or polysorbate 65, propylene glycol, alpha-tocopherol, N-methyl-2-pyrrolidone, ethanol, tetrahydrofurfuryl alcohol, diglyme, dimethylacetamide, dimethyl isosorbide, polyethylene glycol 1000 succinate, poloxamer 407, mono- and di-fatty acid esters of PEG 300, 400, or 1750.

In one embodiment, the at least one co-solvent is selected from a group consisting of polysorbate 80, polysorbate 20 and mixtures thereof, propylene glycol, alpha-tocopherol, dimethyl sulfoxide, ethanol, tetrahydrofurfuryl alcohol, diglyme, polyethylene glycol (PEG) 1000 succinate, poloxamer 407, mono- and di-fatty acid esters of PEG 300, 400, or 1750.

In one embodiment, the at least one co-solvent is selected from a group consisting of polysorbate 80, polysorbate 20 and mixtures thereof, propylene glycol, alpha-tocopherol, ethanol, tetrahydrofurfuryl alcohol, diglyme, polyethylene glycol (PEG) 1000 succinate, poloxamer 407, mono- and di-fatty acid esters of PEG 300, 400, or 1750.

In one embodiment, the at least one co-solvent is selected from a group consisting of ethanol, polyethylene glycol (PEG) 1000 succinate, mono- and di-fatty acid esters of PEG 300, 400, or 1750.

In one embodiment, the at least one co-solvent is selected from a group consisting of ethanol, PEG 300, 400, or 1750. In one embodiment, the at least one co-solvent is selected from a group consisting of ethanol and PEG 400.

In one preferred embodiment, the at least one pharmaceutically acceptable excipient is a co-solvent selected from polysorbates.

In one preferred embodiment, the at least one pharmaceutically acceptable excipient is a co-solvent selected from polysorbates selected from a list consisting of polysorbate 80, polysorbate 20, polysorbate 40, polysorbate 60 or polysorbate 65 and mixtures thereof.

In one preferred embodiment, the at least one pharmaceutically acceptable excipient is polysorbate 80, polysorbate 20 or mixtures thereof.

In one preferred embodiment, the at least one pharmaceutically acceptable excipient is polysorbate 80.

Raising the amount of the co-solvent positively correlates with the aqueous solubility of the compound of the invention. Nevertheless, the Applicant found that excessive use of co-solvents raises the viscosity of the composition and may be deteriorating for the compound's chemical stability.

In one embodiment, the composition according to the present invention does not comprise a co-solvent.

In another embodiment, the composition according to the present invention comprises a co-solvent.

In one embodiment, the amount of co-solvent ranges from 1 to 40% (w/w), from 1 to 30% (w/w), from 1 to 20% (w/w), preferably 2 to 15% (w/w), even more preferably from 5 to 10% (w/w), in weight relative to the total weight of the composition.

In one embodiment, the amount of co-solvent ranges from 1 to 20% (w/w), preferably 2 to 15% (w/w), even more preferably from 5 to 10% (w/w), in weight relative to the total weight of the composition.

Solubility and Concentration of the Inhibitor

The composition of the invention allows to enhance the aqueous solubility of a compound of formula (I).

In one embodiment, the composition according of the invention comprises a compound of formula (I) in an amount ranging from 0.001 to 2 mg/mL, from 0.001 to 1.3 mg/mL. In one embodiment, the composition according of the invention comprises a compound of formula (I) in an amount ranging from 0.1 to 0.6 mg/mL. In one embodiment, the composition according of the invention comprises a compound of formula (I) 0.15 to 0.56 mg/mL.

In one embodiment, the composition according of the invention comprises a compound of formula (I) in an amount ranging from 0.02 to 2 mg/mL, from 0.02 to 1.2 mg/mL, 0.04 to 1.2 mg/mL, preferably from 0.1 to 1.0 mg/mL, even more preferably from 0.1 to 0.7 mg/mL.

In one embodiment, the composition according of the invention comprises AOX in an amount ranging from 0.001 to 1.3 mg/mL. In one embodiment, the composition according of the invention comprises AOX in an amount ranging from 0.1 to 0.6 mg/mL. In one embodiment, the composition according of the invention comprises AOX in an amount ranging from 0.15 to 0.56 mg/mL.

In one embodiment, the composition according of the invention comprises AOX in an amount ranging from 0.02 to 2 mg/mL, from 0.02 to 1.2 mg/mL, 0.04 to 1.2 mg/mL, preferably from 0.1 to 1.0 mg/mL, even more preferably from 0.1 to 0.7 mg/mL.

In one embodiment, the composition according of the invention comprises AOL in an amount ranging from 0.001 to 1.3 mg/mL. In one embodiment, the composition according of the invention comprises AOL in an amount ranging from 0.1 to 0.6 mg/mL. In one embodiment, the composition according of the invention comprises in an amount ranging from AOL 0.15 to 0.56 mg/mL.

In one embodiment, the composition according of the invention comprises AOL in an amount ranging from 0.02 to 2 mg/mL, from 0.02 to 1.2 mg/mL, 0.04 to 1.2 mg/mL, preferably from 0.1 to 1.0 mg/mL, even more preferably from 0.1 to 0.7 mg/mL.

In one embodiment, the composition is a solid composition, preferably a powder composition.

Alternatively, the composition is a liquid composition, preferably an aqueous composition.

In one embodiment, the composition further comprises at least one pharmaceutically acceptable liquid carrier, preferably the liquid carrier is an aqueous solution, more preferably, the liquid carrier is water.

In one embodiment, the viscosity of the aqueous solution does not exceed 7000 mPa·s. In one embodiment, the viscosity of the aqueous solution does not exceed 5000 mPa·s. In one embodiment, the viscosity of the aqueous solution does not exceed 4000 mPa·s. In one embodiment, the viscosity of the aqueous solution does not exceed 2000 mPa·s. In one embodiment, the viscosity of the aqueous solution does not exceed 1000 mPa·s.

In one embodiment, the viscosity of the aqueous solution ranges from 2 to 4000 mPa·s. In one embodiment, the viscosity of the aqueous solution ranges from 3 to 900 mPa·s. In one embodiment, the viscosity of the aqueous solution ranges from 5 to 800 mPa·s. In one embodiment, the viscosity of the aqueous solution ranges from 10 to 800 mPa·s. In one embodiment, the viscosity of the aqueous solution ranges from 50 to 1000 mPa·s. In one embodiment, the viscosity of the aqueous solution ranges from 80 to 1000 mPa·s. The viscosity being measured at 25° C.

The composition of the invention allows to enhance the aqueous solubility of a compound of formula (I).

Amounts and Ratios of the Components of the Composition

In one embodiment, the composition of the invention comprises a cyclodextrin of formula (IV), as previously described, and a compound of formula (I), as previously described; the molar ratio of the cyclodextrin of formula (IV) to the compound of formula (I) ranging from 2.5 to 400, from 10 to 400, preferably from 57 to 200.

In one embodiment, the composition of the invention comprises a cyclodextrin of formula (IV), as previously described, and a compound of formula (I), as previously described; the molar ratio of the cyclodextrin of formula (IV) to the compound of formula (I) ranging from 2.5 to 400, from 57 to 400, from 60 to 250, preferably from 65 to 230, even more preferably from preferably from 57 to 200.

In one embodiment, the composition of the invention comprises hydroxypropyl-β-cyclodextrin and a compound of formula (I), as previously described; the molar ratio of the hydroxypropyl-β-cyclodextrin to the compound of formula (I) ranging from 2.5 to 400, from 10 to 400, preferably from 30 to 200. In one embodiment, the composition of the invention comprises hydroxypropyl-β-cyclodextrin and a compound of formula (I), as previously described; the molar ratio of the hydroxypropyl-β-cyclodextrin to the compound of formula (I) ranging from 2.5 to 400, from 10 to 400, from 30 to 200, from 60 to 300, from 60 to 250.

In one embodiment, the composition of the invention comprises sulfobutylether-β-cyclodextrin and a compound of formula (I), as previously described; the molar ratio of the sulfobutylether-β-cyclodextrin to the compound of formula (I) ranging from 2.5 to 400, from 57 to 400, from 60 to 250, preferably from 65 to 230, even more preferably from preferably from 57 to 200. In one embodiment, the composition of the invention comprises sulfobutylether-β-cyclodextrin and a compound of formula (I), as previously described; the molar ratio of the sulfobutylether-β-cyclodextrin to the compound of formula (I) ranging from 60 to 160, preferably from 80 to 120.

In one embodiment, the composition of the invention comprises a cyclodextrin of formula (IV) and a compound of formula (I) selected from 5-(4-methoxyphenyl)-3H-1,2-dithiole-3-thione; 5-(4-hydroxyphenyl)-3H-1,2-dithiole-3-thione; 5-(4-hydroxyphenyl)-3H-1,2-dithiol-3-one; 5-(4-hydroxyphenyl)-3H-1,2-dithiol-3-one oxime; 5-(4-hydroxyphenyl)-3H-1,2,4-dithiazole-3-thione; 4-(4-hydroxyphenyl)-3H-1,2-dithiole-3-thione; 5-(2-hydroxybenzo[d]oxazol-5-yl)-3H-1,2-dithiole-3-thione; 5-(2-hydroxybenzo[d]thiazol-6-yl)-3H-1,2-dithiole-3-thione; 5-(benzofuran-5-yl)-3H-1,2-dithiole-3-thione; and methyl 5-(3-thioxo-3H-1,2-dithiol-5-yl)-1H-indole-1-carboxylate; the molar ratio of the cyclodextrin of formula (IV) to the compound of formula (I) ranging from 2.5 to 400, from 10 to 400, preferably from 30 to 200.

In one embodiment, the composition of the invention comprises hydroxypropyl-β-cyclodextrin and a compound of formula (I) selected from 5-(4-methoxyphenyl)-3H-1,2-dithiole-3-thione; 5-(4-hydroxyphenyl)-3H-1,2-dithiole-3-thione; 5-(4-hydroxyphenyl)-3H-1,2-dithiol-3-one; 5-(4-hydroxyphenyl)-3H-1,2-dithiol-3-one oxime; 5-(4-hydroxyphenyl)-3H-1,2,4-dithiazole-3-thione; 4-(4-hydroxyphenyl)-3H-1,2-dithiole-3-thione; 5-(2-hydroxybenzo[d]oxazol-5-yl)-3H-1,2-dithiole-3-thione; 5-(2-hydroxybenzo[d]thiazol-6-yl)-3H-1,2-dithiole-3-thione; 5-(benzofuran-5-yl)-3H-1,2-dithiole-3-thione; and methyl 5-(3-thioxo-3H-1,2-dithiol-5-yl)-1H-indole-1-carboxylate; the molar ratio of the hydroxypropyl-β-cyclodextrin to the compound of formula (I) ranging from 2.5 to 400, from 5 to 400, from 10 to 400, from 60 to 300, from 60 to 250 or from 30 to 200.

In one embodiment, the composition of the invention comprises sulfobutylether-β-cyclodextrin and a compound of formula (I) selected from 5-(4-methoxyphenyl)-3H-1,2-dithiole-3-thione; 5-(4-hydroxyphenyl)-3H-1,2-dithiole-3-thione; 5-(4-hydroxyphenyl)-3H-1,2-dithiol-3-one; 5-(4-hydroxyphenyl)-3H-1,2-dithiol-3-one oxime; 5-(4-hydroxyphenyl)-3H-1,2,4-dithiazole-3-thione; 4-(4-hydroxyphenyl)-3H-1,2-dithiole-3-thione; 5-(2-hydroxybenzo[d]oxazol-5-yl)-3H-1,2-dithiole-3-thione; 5-(2-hydroxybenzo[d]thiazol-6-yl)-3H-1,2-dithiole-3-thione; 5-(benzofuran-5-yl)-3H-1,2-dithiole-3-thione; and methyl 5-(3-thioxo-3H-1,2-dithiol-5-yl)-1H-indole-1-carboxylate; the molar ratio of the sulfobutylether-β-cyclodextrin to the compound of formula (I) ranging from 2.5 to 400, from 57 to 400, from 60 to 160, preferably from 80 to 150, even more preferably from preferably from 90 to 120.

In one embodiment, the composition of the invention comprises a cyclodextrin of formula (IV) and a compound of formula (I) selected from 5-(4-methoxyphenyl)-3H-1,2-dithiole-3-thione and 5-(4-hydroxyphenyl)-3H-1,2-dithiole-3-thione; the molar ratio of the cyclodextrin of formula (IV) to the compound of formula (I) ranging from 2.5 to 400, from 10 to 400, preferably from 30 to 200.

In one embodiment, the composition of the invention comprises hydroxypropyl-β-cyclodextrin and a compound of formula (I) selected from 5-(4-methoxyphenyl)-3H-1,2-dithiole-3-thione and 5-(4-hydroxyphenyl)-3H-1,2-dithiole-3-thione; the molar ratio of the hydroxypropyl-β-cyclodextrin to the compound of formula (I) ranging from 2.5 to 400, from 60 to 300, from 60 to 250 or from 30 to 200.

In one embodiment, the composition of the invention comprises sulfobutylether-β-cyclodextrin and a compound of formula (I) selected from 5-(4-methoxyphenyl)-3H-1,2-dithiole-3-thione and 5-(4-hydroxyphenyl)-3H-1,2-dithiole-3-thione; the molar ratio of the sulfobutylether-β-cyclodextrin to the compound of formula (I) ranging from 2.5 to 400, from 57 to 400, from 60 to 160, preferably from 80 to 120, even more preferably from preferably from 90 to 120.

In one embodiment, the composition of the invention comprises a cyclodextrin of formula (IV) and 5-(4-methoxyphenyl)-3H-1,2-dithiole-3-thione; the molar ratio of the cyclodextrin of formula (IV) to 5-(4-methoxyphenyl)-3H-1,2-dithiole-3-thione ranging from 2.5 to 400, from 10 to 400, preferably from 30 to 200.

In one embodiment, the composition of the invention comprises hydroxypropyl-β-cyclodextrin and 5-(4-methoxyphenyl)-3H-1,2-dithiole-3-thione; the molar ratio of the hydroxypropyl-β-cyclodextrin to 5-(4-methoxyphenyl)-3H-1,2-dithiole-3-thione ranging from 2.5 to 400, from 5 to 400, from 10 to 400, from 60 to 300, from 60 to 250 or from 30 to 200.

In one embodiment, the composition of the invention comprises sulfobutylether-β-cyclodextrin and 5-(4-methoxyphenyl)-3H-1,2-dithiole-3-thione; the molar ratio of the sulfobutylether-β-cyclodextrin to 5-(4-methoxyphenyl)-3H-1,2-dithiole-3-thione ranging from about 2.5 to about 400, from about 57 to about 400, from about 57 to about 200, preferably from about 57 to about 170, even more preferably from about 57 to about 160.

In one embodiment, the composition of the invention comprises sulfobutylether-β-cyclodextrin and 5-(4-methoxyphenyl)-3H-1,2-dithiole-3-thione; the molar ratio of the sulfobutylether-β-cyclodextrin to 5-(4-methoxyphenyl)-3H-1,2-dithiole-3-thione ranging from about 2.5 to about 400, from about 57 to about 400, from about 57 to about 200, preferably from about 57 to about 170, even more preferably from about 57 to about 160.

In one embodiment, the composition of the invention comprises sulfobutylether-β-cyclodextrin and 5-(4-methoxyphenyl)-3H-1,2-dithiole-3-thione; the molar ratio of the sulfobutylether-β-cyclodextrin to 5-(4-methoxyphenyl)-3H-1,2-dithiole-3-thione ranging from 2.5 to 400, from 57 to 400, from 60 to 160, preferably from 80 to 120, even more preferably from preferably from 90 to 110.

In one embodiment, the composition of the invention comprises sulfobutylether-β-cyclodextrin and 5-(4-methoxyphenyl)-3H-1,2-dithiole-3-thione; the molar ratio of the sulfobutylether-β-cyclodextrin to 5-(4-methoxyphenyl)-3H-1,2-dithiole-3-thione ranging from 57 to about 160.

In one embodiment, the composition of the invention comprises sulfobutylether-β-cyclodextrin and 5-(4-methoxyphenyl)-3H-1,2-dithiole-3-thione; the molar ratio of the sulfobutylether-β-cyclodextrin to 5-(4-methoxyphenyl)-3H-1,2-dithiole-3-thione ranging from about 70 to about 160.

In one embodiment, the composition of the invention comprises sulfobutylether-β-cyclodextrin and 5-(4-methoxyphenyl)-3H-1,2-dithiole-3-thione; the molar ratio of the sulfobutylether-β-cyclodextrin to 5-(4-methoxyphenyl)-3H-1,2-dithiole-3-thione ranging from about 80 to about 120.

In one embodiment, the composition of the invention comprises sulfobutylether-β-cyclodextrin and 5-(4-methoxyphenyl)-3H-1,2-dithiole-3-thione; the molar ratio of the sulfobutylether-β-cyclodextrin to 5-(4-methoxyphenyl)-3H-1,2-dithiole-3-thione ranging from about 90 to about 120.

In one embodiment, the composition of the invention comprises sulfobutylether-β-cyclodextrin and 5-(4-methoxyphenyl)-3H-1,2-dithiole-3-thione; the molar ratio of the sulfobutylether-β-cyclodextrin to 5-(4-methoxyphenyl)-3H-1,2-dithiole-3-thione being about 100.

In one embodiment, the composition of the invention comprises a cyclodextrin of formula (IV), a buffer selected from citrate buffer, tris(hydroxymethyl)aminomethane (Tris) buffer, 4-(2-hydroxyethyl)-1-piperazine ethanesulfonic acid (HEPES) buffer, ammonium sulfate, carbonate or acetate buffer, and 5-(4-methoxyphenyl)-3H-1,2-dithiole-3-thione; the molar ratio of the cyclodextrin of formula (IV) to 5-(4-methoxyphenyl)-3H-1,2-dithiole-3-thione ranging from 2.5 to 400, from 10 to 400, preferably from 30 to 200.

In one embodiment, the composition of the invention comprises hydroxypropyl-β-cyclodextrin, a buffer selected from citrate buffer, tris(hydroxymethyl)aminomethane (Tris) buffer, 4-(2-hydroxyethyl)-1-piperazine ethanesulfonic acid (HEPES) buffer, ammonium sulfate, carbonate or acetate buffer and 5-(4-methoxyphenyl)-3H-1,2-dithiole-3-thione; the molar ratio of the hydroxypropyl-β-cyclodextrin to 5-(4-methoxyphenyl)-3H-1,2-dithiole-3-thione ranging from 2.5 to 400, from 5 to 400, from 10 to 400, from 60 to 300, from 60 to 250 or from 30 to 200.

In one embodiment, the composition of the invention comprises sulfobutylether-β-cyclodextrin, a buffer selected from citrate buffer, tris(hydroxymethyl)aminomethane (Tris) buffer, 4-(2-hydroxyethyl)-1-piperazine ethanesulfonic acid (HEPES) buffer, ammonium sulfate, carbonate or acetate buffer and 5-(4-methoxyphenyl)-3H-1,2-dithiole-3-thione; the molar ratio of the sulfobutylether-β-cyclodextrin to 5-(4-methoxyphenyl)-3H-1,2-dithiole-3-thione ranging from about 2.5 to about 400, from about 57 to about 400, from about 57 to about 200, 5 preferably from about 57 to about 170, even more preferably from about 57 to about 160.

In one embodiment, the composition of the invention comprises sulfobutylether-β-cyclodextrin, a buffer selected from citrate buffer, tris(hydroxymethyl)aminomethane (Tris) buffer, 4-(2-hydroxyethyl)-1-piperazine ethanesulfonic acid (HEPES) buffer, ammonium sulfate, carbonate or acetate buffer, and 5-(4-methoxyphenyl)-3H-1,2-dithiole-3-thione; the molar ratio of the sulfobutylether-β-cyclodextrin to 5-(4-methoxyphenyl)-3H-1,2-dithiole-3-thione ranging from 2.5 to 400, from 57 to 400, from 60 to 160, preferably from 80 to 120, even more preferably from preferably from 90 to 120.

In one embodiment, the composition of the invention comprises sulfobutylether-β-cyclodextrin, a buffer selected from citrate buffer, tris(hydroxymethyl)aminomethane (Tris) buffer, 4-(2-hydroxyethyl)-1-piperazine ethanesulfonic acid (HEPES) buffer, ammonium sulfate, carbonate or acetate buffer, and 5-(4-methoxyphenyl)-3H-1,2-dithiole-3-thione; the molar ratio of the sulfobutylether-β-cyclodextrin to 5-(4-methoxyphenyl)-3H-1,2-dithiole-3-thione ranging from 57 to about 160.

In one embodiment, the composition of the invention comprises sulfobutylether-β-cyclodextrin, a buffer selected from citrate buffer, tris(hydroxymethyl)aminomethane (Tris) buffer, 4-(2-hydroxyethyl)-1-piperazine ethanesulfonic acid (HEPES) buffer, ammonium sulfate, carbonate or acetate buffer, and 5-(4-methoxyphenyl)-3H-1,2-dithiole-3-thione; the molar ratio of the sulfobutylether-β-cyclodextrin to 5-(4-methoxyphenyl)-3H-1,2-dithiole-3-thione ranging from about 70 to about 160.

In one embodiment, the composition of the invention comprises sulfobutylether-β-cyclodextrin, a buffer selected from citrate buffer, tris(hydroxymethyl)aminomethane (Tris) buffer, 4-(2-hydroxyethyl)-1-piperazine ethanesulfonic acid (HEPES) buffer, ammonium sulfate, carbonate or acetate buffer, and 5-(4-methoxyphenyl)-3H-1,2-dithiole-3-thione; the molar ratio of the sulfobutylether-β-cyclodextrin to 5-(4-methoxyphenyl)-3H-1,2-dithiole-3-thione ranging from about 80 to about 120.

In one embodiment, the composition of the invention comprises sulfobutylether-β-cyclodextrin, a buffer selected from citrate buffer, tris(hydroxymethyl)aminomethane (Tris) buffer, 4-(2-hydroxyethyl)-1-piperazine ethanesulfonic acid (HEPES) buffer, ammonium sulfate, carbonate or acetate buffer, and 5-(4-methoxyphenyl)-3H-1,2-dithiole-3-thione; the molar ratio of the sulfobutylether-β-cyclodextrin to 5-(4-methoxyphenyl)-3H-1,2-dithiole-3-thione ranging from about 90 to about 120.

In one embodiment, the composition of the invention comprises a cyclodextrin of formula (IV) and 5-(4-hydroxyphenyl)-3H-1,2-dithiole-3-thione; the molar ratio of the cyclodextrin of formula (IV) to 5-(4-hydroxyphenyl)-3H-1,2-dithiole-3-thione ranging from 2.5 to 400, from 10 to 400, preferably from 30 to 200.

In one embodiment, the composition of the invention comprises hydroxypropyl-β-cyclodextrin and 5-(4-hydroxyphenyl)-3H-1,2-dithiole-3-thione; the molar ratio of the hydroxypropyl-β-cyclodextrin to 5-(4-hydroxyphenyl)-3H-1,2-dithiole-3-thione ranging from about 2.5 to about 400, from about 10 to about 400, from about 60 to about 300, from about 60 to about 250.

In one embodiment, the composition of the invention comprises hydroxypropyl-β-cyclodextrin and 5-(4-hydroxyphenyl)-3H-1,2-dithiole-3-thione; the molar ratio of the hydroxypropyl-β-cyclodextrin to 5-(4-hydroxyphenyl)-3H-1,2-dithiole-3-thione ranging from about 2.5 to about 400, from about 10 to about 400, from about 60 to about 300, from about 60 to about 250.

In one embodiment, the composition of the invention comprises sulfobutylether-β-cyclodextrin and 5-(4-hydroxyphenyl)-3H-1,2-dithiole-3-thione; the molar ratio of the sulfobutylether-β-cyclodextrin to 5-(4-hydroxyphenyl)-3H-1,2-dithiole-3-thione ranging from about 2.5 to about 400, from about 10 to about 400, from about 30 to about 200, from about 10 to about 170, preferably from about 40 to about 170, even more preferably from about 40 to about 160.

In one embodiment, the composition of the invention comprises sulfobutylether-β-cyclodextrin and 5-(4-hydroxyphenyl)-3H-1,2-dithiole-3-thione; the molar ratio of the sulfobutylether-β-cyclodextrin to 5-(4-hydroxyphenyl)-3H-1,2-dithiole-3-thione ranging from 2.5 to 400, from 10 to 400, from 30 to 200, from 10 to 170, preferably from 40 to 170, even more preferably from 40 to 160.

In one embodiment, the composition of the invention comprises sulfobutylether-β-cyclodextrin and 5-(4-hydroxyphenyl)-3H-1,2-dithiole-3-thione; the molar ratio of the sulfobutylether-β-cyclodextrin to 5-(4-hydroxyphenyl)-3H-1,2-dithiole-3-thione ranging from 2.5 to 400, from 57 to 400, from 60 to 160, preferably from 80 to 120, even more preferably from preferably from 90 to 120.

In one embodiment, the composition of the invention comprises a cyclodextrin of formula (IV), as previously described, a compound of formula (I), as previously described; and at least one excipient, preferably the excipient being a co-solvent, as previously described; the molar ratio of the cyclodextrin of formula (IV) to the compound of formula (I) ranging from 2.5 to 400, from 10 to 400, preferably from 30 to 200.

In one embodiment, the composition of the invention comprises:
  a cyclodextrin of formula (IV), as previously described;
  a compound of formula (I), as previously described; and
  at least one co-solvent, selected from a list consisting of polysorbates, propylene glycol, glycerin, paraffin oil, alpha-tocopherol, dimethyl sulfoxide, N-methyl-2-pyrrolidone, glycofurol, Solketal, glycerol formal, acetone, ethanol, tetrahydrofurfuryl alcohol, diglyme, dimethylacetamide, dimethyl isosorbide, ethyl lactate, Cremophor EL, Cremophor RH 40, Cremophor RH 60, Solutol HS 15, poloxamer 407, Labrasol, Gellucire 44/14, Softigen 767, mono- and di-fatty acid esters mono- and di-fatty acid esters of PEG 200, PEG 300, PEG 400, PEG 600, PEG 1750, PEG 2000 to 20000, PEG 1000 succinate; hydrogenated soy phosphatidylcholine, distearoylphosphatidylglycerol, L-α-dimyristoyl-phosphatidylcholine, L-α-dimyristoyl-phosphatidylglycerol and mixtures thereof;
the molar ratio of the cyclodextrin of formula (IV) to the compound of formula (I) ranging 2.5 to 400, from 10 to 400, preferably from 30 to 200.

In one embodiment, the composition of the invention comprises:
  a cyclodextrin of formula (IV), as previously described;
  a compound of formula (I), as previously described; and
  at least one co-solvent, selected from a list consisting of polysorbate 80, polysorbate 20 and mixtures thereof, propylene glycol, alpha-tocopherol, dimethyl sulfoxide, ethanol, tetrahydrofurfuryl alcohol, diglyme, polyethylene glycol (PEG) 1000 succinate, poloxamer 407, mono- and di-fatty acid esters of PEG 300, 400, or 1750;
the molar ratio of the cyclodextrin of formula (IV) to the compound of formula (I) ranging 2.5 to 400, from 10 to 400, preferably from 57 to 200.

In one embodiment, the composition of the invention comprises:
  hydroxypropyl-β-cyclodextrin;
  a compound of formula (I), as previously described; and
  at least one co-solvent, selected from a list consisting of polysorbate 80, polysorbate 20 and mixtures thereof, propylene glycol, alpha-tocopherol, dimethyl sulfoxide, ethanol, tetrahydrofurfuryl alcohol, diglyme, polyethylene glycol (PEG) 1000 succinate, poloxamer 407, mono- and di-fatty acid esters of PEG 300, 400, or 1750;
the molar ratio of the hydroxypropyl-β-cyclodextrin to the compound of formula (I) ranging from 2.5 to 400, from 60 to 300, from 60 to 250.

In one embodiment, the composition of the invention comprises:
  sulfobutylether-β-cyclodextrin;
  a compound of formula (I), as previously described; and optionally
  at least one co-solvent, selected from a list consisting of polysorbates, propylene glycol, glycerin, paraffin oil, alpha-tocopherol, dimethyl sulfoxide, N-methyl-2-pyrrolidone, glycofurol, Solketal, glycerol formal, acetone, ethanol, tetrahydrofurfuryl alcohol, diglyme, dimethylacetamide, dimethyl isosorbide, ethyl lactate, Cremophor EL, Cremophor RH 40, Cremophor RH 60, Solutol HS 15, poloxamer 407, Labrasol, Gellucire 44/14, Softigen 767, mono- and di-fatty acid esters mono- and di-fatty acid esters of PEG 200, PEG 300, PEG 400, PEG 600, PEG 1750, PEG 2000 to 20000, PEG 1000 succinate; hydrogenated soy phosphatidylcholine, distearoylphosphatidylglycerol, L-α-dimyristoyl-phosphatidylcholine, L-α-dimyristoyl-phosphatidylglycerol and mixtures thereof;

the molar ratio of the sulfobutylether-β-cyclodextrin to the compound of formula (I) ranging from 2.5 to 400, from 57 to 400, from 60 to 160, preferably from 80 to 120, even more preferably from preferably from 90 to 120.

In one embodiment, the composition of the invention comprises:
  sulfobutylether-β-cyclodextrin;
  a compound of formula (I), as previously described; and optionally
  at least one co-solvent, selected from a list consisting of polysorbate 80, polysorbate 20 and mixtures thereof, propylene glycol, alpha-tocopherol, dimethyl sulfoxide, ethanol, tetrahydrofurfuryl alcohol, diglyme, polyethylene glycol (PEG) 1000 succinate, poloxamer 407, mono- and di-fatty acid esters of PEG 300, 400, or 1750;

the molar ratio of the sulfobutylether-β-cyclodextrin to the compound of formula (I) ranging from 2.5 to 400, from 57 to 400, from 60 to 160, preferably from 80 to 120, even more preferably from preferably from 90 to 120.

In one embodiment, the composition of the invention comprises:
  sulfobutylether-β-cyclodextrin;
  a compound of formula (I), as previously described; and optionally
  at least one co-solvent, selected from a list consisting of polysorbate 80, polysorbate 20 and mixtures thereof;

the molar ratio of the sulfobutylether-β-cyclodextrin to the compound of formula (I) ranging from 2.5 to 400, from 57 to 400, from 60 to 160, preferably from 80 to 120, even more preferably from preferably from 90 to 120.

In one embodiment, the composition of the invention comprises:
  sulfobutylether-β-cyclodextrin;
  a compound of formula (I) selected from 5-(4-methoxyphenyl)-3H-1,2-dithiole-3-thione; 5-(4-hydroxyphenyl)-3H-1,2-dithiole-3-thione; 5-(4-hydroxyphenyl)-3H-1,2-dithiol-3-one; 5-(4-hydroxyphenyl)-3H-1,2-dithiol-3-one oxime; 5-(4-hydroxyphenyl)-3H-1,2,4-dithiazole-3-thione; 4-(4-hydroxyphenyl)-3H-1,2-dithiole-3-thione; 5-(2-hydroxybenzo[d]oxazol-5-yl)-3H-1,2-dithiole-3-thione; 5-(2-hydroxybenzo[d]thiazol-6-yl)-3H-1,2-dithiole-3-thione; 5-(benzofuran-5-yl)-3H-1,2-dithiole-3-thione; and methyl 5-(3-thioxo-3H-1,2-dithiol-5-yl)-1H-indole-1-carboxylate; and optionally
  at least one co-solvent, selected from a list consisting of polysorbates, propylene glycol, glycerin, paraffin oil, alpha-tocopherol, dimethyl sulfoxide, N-methyl-2-pyrrolidone, glycofurol, Solketal, glycerol formal, acetone, ethanol, tetrahydrofurfuryl alcohol, diglyme, dimethylacetamide, dimethyl isosorbide, ethyl lactate, Cremophor EL, Cremophor RH 40, Cremophor RH 60, Solutol HS 15, poloxamer 407, Labrasol, Gellucire 44/14, Softigen 767, mono- and di-fatty acid esters mono- and di-fatty acid esters of PEG 200, PEG 300, PEG 400, PEG 600, PEG 1750, PEG 2000 to 20000, PEG 1000 succinate; hydrogenated soy phosphatidylcholine, distearoylphosphatidylglycerol, L-α-dimyristoyl-phosphatidylcholine, L-α-dimyristoyl-phosphatidylglycerol and mixtures thereof;

the molar ratio of the sulfobutylether-β-cyclodextrin to the compound of formula (I) ranging from 2.5 to 400, from 57 to 400, from 60 to 160, preferably from 80 to 120, even more preferably from preferably from 90 to 120.

In one embodiment, the composition of the invention comprises:
  sulfobutylether-β-cyclodextrin;
  a compound of formula (I) selected from 5-(4-methoxyphenyl)-3H-1,2-dithiole-3-thione; 5-(4-hydroxyphenyl)-3H-1,2-dithiole-3-thione; 5-(4-hydroxyphenyl)-3H-1,2-dithiol-3-one; 5-(4-hydroxyphenyl)-3H-1,2-dithiol-3-one oxime; 5-(4-hydroxyphenyl)-3H-1,2,4-dithiazole-3-thione; 4-(4-hydroxyphenyl)-3H-1,2-dithiole-3-thione; 5-(2-hydroxybenzo[d]oxazol-5-yl)-3H-1,2-dithiole-3-thione; 5-(2-hydroxybenzo[d]thiazol-6-yl)-3H-1,2-dithiole-3-thione; 5-(benzofuran-5-yl)-3H-1,2-dithiole-3-thione; and methyl 5-(3-thioxo-3H-1,2-dithiol-5-yl)-1H-indole-1-carboxylate;
  a buffer selected from citrate buffer, phosphate buffer tris(hydroxymethyl)-aminomethane (Tris) buffer, 4-(2-hydroxyethyl)-1-piperazine ethanesulfonic acid (HEPES) buffer, ammonium sulfate buffer, carbonate buffer or acetate buffer, preferably the buffer being phosphate buffer; and
  optionally at least one co-solvent, selected from a list consisting of polysorbates, propylene glycol, glycerin, paraffin oil, alpha-tocopherol, dimethyl sulfoxide, N-methyl-2-pyrrolidone, glycofurol, Solketal, glycerol formal, acetone, ethanol, tetrahydrofurfuryl alcohol, diglyme, dimethylacetamide, dimethyl isosorbide, ethyl lactate, mono- and di-fatty acid esters mono- and di-fatty acid esters of PEG 200, PEG 300, PEG 400, PEG 600, PEG 1750, PEG 2000 to 20000, PEG 1000 succinate; hydrogenated soy phosphatidylcholine, distearoylphosphatidylglycerol, L-α-dimyristoyl-phosphatidylcholine, L-α-dimyristoyl-phosphatidylglycerol and mixtures thereof;

the molar ratio of the sulfobutylether-β-cyclodextrin to the compound of formula (I) ranging from 2.5 to 400, from 57 to 400, from 60 to 160, preferably from 80 to 120, even more preferably from preferably from 90 to 120.

In one embodiment, the composition of the invention comprises:
  sulfobutylether-β-cyclodextrin;
  a compound of formula (I) selected from 5-(4-methoxyphenyl)-3H-1,2-dithiole-3-thione; 5-(4-hydroxyphenyl)-3H-1,2-dithiole-3-thione; 5-(4-hydroxyphenyl)-3H-1,2-dithiol-3-one; 5-(4-hydroxyphenyl)-3H-1,2-dithiol-3-one oxime; 5-(4-hydroxyphenyl)-3H-1,2,4-dithiazole-3-thione; 4-(4-hydroxyphenyl)-3H-1,2-dithiole-3-thione; 5-(2-hydroxybenzo[d]oxazol-5-yl)-3H-1,2-dithiole-3-thione; 5-(2-hydroxybenzo[d]thiazol-6-yl)-3H-1,2-dithiole-3-thione; 5-(benzofuran-5-yl)-3H-1,2-dithiole-3-thione; and methyl 5-(3-thioxo-3H-1,2-dithiol-5-yl)-1H-indole-1-carboxylate;
  a buffer selected from citrate buffer, phosphate buffer tris(hydroxymethyl)-aminomethane (Tris) buffer, 4-(2-hydroxyethyl)-1-piperazine ethanesulfonic acid (HEPES) buffer, ammonium sulfate buffer, carbonate buffer or acetate buffer, preferably the buffer being phosphate buffer; and optionally at least one co-solvent, selected from a list consisting of polysorbate 80, polysorbate 20 and mixtures thereof;

the molar ratio of the sulfobutylether-β-cyclodextrin to the compound of formula (I) ranging from 2.5 to 400, from 57 to 400, from 60 to 160, preferably from 80 to 120, even more preferably from preferably from 90 to 120.

In one embodiment, the composition of the invention comprises:
- sulfobutylether-β-cyclodextrin;
- a compound of formula (I) selected from 5-(4-methoxyphenyl)-3H-1,2-dithiole-3-thione; 5-(4-hydroxyphenyl)-3H-1,2-dithiole-3-thione; 5-(4-hydroxyphenyl)-3H-1,2-dithiol-3-one; 5-(4-hydroxyphenyl)-3H-1,2-dithiol-3-one oxime; 5-(4-hydroxyphenyl)-3H-1,2,4-dithiazole-3-thione; 4-(4-hydroxyphenyl)-3H-1,2-dithiole-3-thione; 5-(2-hydroxybenzo[d]oxazol-5-yl)-3H-1,2-dithiole-3-thione; 5-(2-hydroxybenzo[d]thiazol-6-yl)-3H-1,2-dithiole-3-thione; 5-(benzofuran-5-yl)-3H-1,2-dithiole-3-thione; and methyl 5-(3-thioxo-3H-1,2-dithiol-5-yl)-1H-indole-1-carboxylate;
- a buffer selected from citrate buffer, phosphate buffer tris(hydroxymethyl)-aminomethane (Tris) buffer, 4-(2-hydroxyethyl)-1-piperazine ethanesulfonic acid (HEPES) buffer, ammonium sulfate buffer, carbonate buffer or acetate buffer, preferably the buffer being phosphate buffer; and
- optionally at least one co-solvent, selected from a list consisting of polysorbate 80, polysorbate 20 and mixtures thereof;

the molar ratio of the sulfobutylether-β-cyclodextrin to the compound of formula (I) ranging from 2.5 to 400, from 57 to 400, from 60 to 160, preferably from 80 to 120, even more preferably from preferably from 90 to 120.

In one preferred embodiment, the composition of the invention comprises:
- sulfobutylether-β-cyclodextrin;
- a compound of formula (I) selected from 5-(4-methoxyphenyl)-3H-1,2-dithiole-3-thione and 5-(4-hydroxyphenyl)-3H-1,2-dithiole-3-thione; and
- optionally at least one co-solvent, selected from a list consisting of polysorbates, propylene glycol, glycerin, paraffin oil, alpha-tocopherol, dimethyl sulfoxide, N-methyl-2-pyrrolidone, glycofurol, Solketal, glycerol formal, acetone, ethanol, tetrahydrofurfuryl alcohol, diglyme, dimethylacetamide, dimethyl isosorbide, ethyl lactate, Cremophor EL, Cremophor RH 40, Cremophor RH 60, Solutol HS 15, poloxamer 407, Labrasol, Gellucire 44/14, Softigen 767, mono- and di-fatty acid esters mono- and di-fatty acid esters of PEG 200, PEG 300, PEG 400, PEG 600, PEG 1750, PEG 2000 to 20000, PEG 1000 succinate; hydrogenated soy phosphatidylcholine, distearoylphosphatidylglycerol, L-α-dimyristoyl-phosphatidylcholine, L-α-dimyristoyl-phosphatidylglycerol and mixtures thereof;

the molar ratio of the sulfobutylether-β-cyclodextrin to the compound of formula (I) ranging from 2.5 to 400, from 57 to 400, from 60 to 160, preferably from 80 to 120, even more preferably from preferably from 90 to 120.

In one preferred embodiment, the composition of the invention comprises:
- sulfobutylether-β-cyclodextrin;
- a compound of formula (I) selected from 5-(4-methoxyphenyl)-3H-1,2-dithiole-3-thione and 5-(4-hydroxyphenyl)-3H-1,2-dithiole-3-thione;
- a buffer selected from citrate buffer, phosphate buffer tris(hydroxymethyl)-aminomethane (Tris) buffer, 4-(2-hydroxyethyl)-1-piperazine ethanesulfonic acid (HEPES) buffer, ammonium sulfate buffer, carbonate buffer or acetate buffer, preferably the buffer being phosphate buffer; and
- optionally at least one co-solvent, selected from a list consisting of polysorbate 80, polysorbate 20 and mixtures thereof, propylene glycol, alpha-tocopherol, dimethyl sulfoxide, ethanol, tetrahydrofurfuryl alcohol, diglyme, polyethylene glycol (PEG) 1000 succinate, poloxamer 407, mono- and di-fatty acid esters of PEG 300, 400, or 1750;

the molar ratio of the sulfobutylether-β-cyclodextrin to the compound of formula (I) ranging from 2.5 to 400, from 57 to 400, from 60 to 160, preferably from 80 to 120, even more preferably from preferably from 90 to 120.

In one embodiment, the composition of the invention comprises:
- sulfobutylether-β-cyclodextrin;
- 5-(4-methoxyphenyl)-3H-1,2-dithiole-3-thione;
- a buffer selected from citrate buffer, phosphate buffer tris(hydroxymethyl)-aminomethane (Tris) buffer, 4-(2-hydroxyethyl)-1-piperazine ethanesulfonic acid (HEPES) buffer, ammonium sulfate buffer, carbonate buffer or acetate buffer, preferably the buffer being phosphate buffer; and optionally
- at least one co-solvent, selected from a list consisting of polysorbate 80, polysorbate 20 and mixtures thereof, propylene glycol, alpha-tocopherol, dimethyl sulfoxide, ethanol, tetrahydrofurfuryl alcohol, diglyme, polyethylene glycol (PEG) 1000 succinate, poloxamer 407, mono- and di-fatty acid esters of PEG 300, 400, or 1750;

the molar ratio of the sulfobutylether-β-cyclodextrin to 5-(4-methoxyphenyl)-3H-1,2-dithiole-3-thione ranging from 2.5 to 400, from 57 to 200, from 60 to 160, preferably from 80 to 120, even more preferably from preferably from 90 to 120.

In one preferred embodiment, the composition of the invention comprises:
- sulfobutylether-β-cyclodextrin;
- 5-(4-methoxyphenyl)-3H-1,2-dithiole-3-thione; and
- at least one co-solvent, selected from a list consisting of polysorbate 80, polysorbate 20 and mixtures thereof, preferably the co-solvent in polysorbate 80;

the molar ratio of the sulfobutylether-β-cyclodextrin to 5-(4-methoxyphenyl)-3H-1,2-dithiole-3-thione ranging from 2.5 to 400, from 57 to 200, from 60 to 160, preferably from 80 to 120, even more preferably from preferably from 90 to 120.

In one embodiment, the composition of the invention comprises:
- sulfobutylether-β-cyclodextrin, in an amount ranging from 1 to 40% (w/w), preferably 2.5 to 30% (w/w), even more preferably from 5 to 20% (w/w), in weight relative to the total weight of the composition;
- 5-(4-methoxyphenyl)-3H-1,2-dithiole-3-thione at a concentration ranging from 00.04 to 1.2 mg/mL, preferably from 0.1 to 1.0 mg/mL, even more preferably from 0.1 to 0.7 mg/mL; and optionally
- at least one co-solvent, selected from a list consisting of polysorbate 80, polysorbate 20 and mixtures thereof, preferably the co-solvent in polysorbate 80; the at least one co-solvent ranging from 1 to 40% (w/w), from 1 to 30% (w/w), from 1 to 20% (w/w), preferably 2 to 15% (w/w), in weight relative to the total weight of the composition;

the molar ratio of the sulfobutylether-β-cyclodextrin to 5-(4-methoxyphenyl)-3H-1,2-dithiole-3-thione ranging from about 2.5 to about 400, from about 57 to about 200, from about 60 to about 160, preferably from about 80 to about 120, even more preferably from about 90 to about 120.

In one embodiment, the composition of the invention comprises:
- sulfobutylether-β-cyclodextrin, in an amount ranging from 1 to 40% (w/w), preferably 2.5 to 30% (w/w), even more preferably from 5 to 20% (w/w), in weight relative to the total weight of the composition;
- 5-(4-methoxyphenyl)-3H-1,2-dithiole-3-thione at a concentration ranging 0.02 to 2 mg/mL, from 0.02 to 1.2 mg/mL, 0.04 to 1.2 mg/mL, preferably from 0.1 to 1.0 mg/mL, even more preferably from 0.1 to 0.7 mg/mL; and optionally
- at least one co-solvent, selected from a list consisting of polysorbate 80, polysorbate 20 and mixtures thereof, preferably the co-solvent in polysorbate 80; the at least one co-solvent ranging from 1 to 40% (w/w), from 1 to 30% (w/w), from 1 to 20% (w/w), preferably 2 to 15% (w/w), in weight relative to the total weight of the composition;

the molar ratio of the sulfobutylether-β-cyclodextrin to 5-(4-methoxyphenyl)-3H-1,2-dithiole-3-thione ranging from 2.5 to 400, from 57 to 200, from 60 to 160, preferably from 80 to 120, even more preferably from preferably from 90 to 120.

In one embodiment, the composition of the invention comprises:
- sulfobutylether-β-cyclodextrin, in an amount ranging from 1 to 40% (w/w), preferably 2.5 to 30% (w/w), even more preferably from 5 to 20% (w/w), in weight relative to the total weight of the composition;
- 5-(4-methoxyphenyl)-3H-1,2-dithiole-3-thione at a concentration ranging 0.02 to 2 mg/mL, from 0.02 to 1.2 mg/mL, 0.04 to 1.2 mg/mL, preferably from 0.1 to 1.0 mg/mL, even more preferably from 0.1 to 0.7 mg/mL;
- Phosphate buffer in an amount ranging from 10 to 150 mM; and optionally
- at least one co-solvent, selected from a list consisting of polysorbate 80, polysorbate 20 and mixtures thereof, preferably the co-solvent in polysorbate 80; the at least one co-solvent ranging from 1 to 40% (w/w), from 1 to 30% (w/w), from 1 to 20% (w/w), preferably 2 to 15% (w/w), in weight relative to the total weight of the composition;

the molar ratio of the sulfobutylether-β-cyclodextrin to 5-(4-methoxyphenyl)-3H-1,2-dithiole-3-thione ranging from 2.5 to 400, from 57 to 200, from 60 to 160, preferably from 80 to 120, even more preferably from preferably from 90 to 120.

In one embodiment, the composition of the invention comprises:
- sulfobutylether-β-cyclodextrin, in an amount ranging 5 to 20% (w/w), in weight relative to the total weight of the composition;
- 5-(4-methoxyphenyl)-3H-1,2-dithiole-3-thione at a concentration ranging from 0.1 to 1.0 mg/mL, preferably from 0.1 to 0.7 mg/mL;
- Phosphate buffer in an amount ranging from 10 to 150 mM;

the molar ratio of the sulfobutylether-β-cyclodextrin to 5-(4-methoxyphenyl)-3H-1,2-dithiole-3-thione ranging from 60 to 160, preferably from 80 to 120, even more preferably from preferably from 90 to 120.

In one embodiment, the composition of the invention comprises:
- sulfobutylether-β-cyclodextrin, in an amount of about 5 or about 10% (w/w), in weight relative to the total weight of the composition;
- 5-(4-methoxyphenyl)-3H-1,2-dithiole-3-thione at a concentration ranging from 0.1 to 0.7 mg/mL;
- Phosphate buffer in an amount ranging from 25 to 100 mM;

the molar ratio of the sulfobutylether-β-cyclodextrin to 5-(4-methoxyphenyl)-3H-1,2-dithiole-3-thione ranging from 90 to 120.

In one embodiment, the composition of the invention comprises:
- sulfobutylether-β-cyclodextrin, in an amount of about 20% (w/w), in weight relative to the total weight of the composition;
- 5-(4-methoxyphenyl)-3H-1,2-dithiole-3-thione at a concentration ranging from 0.1 to 0.7 mg/mL;
- Phosphate buffer in an amount ranging from 25 to 100 mM;

the molar ratio of the sulfobutylether-β-cyclodextrin to 5-(4-methoxyphenyl)-3H-1,2-dithiole-3-thione ranging from 90 to 120, preferably the molar ratio of the sulfobutylether-β-cyclodextrin to 5-(4-methoxyphenyl)-3H-1,2-dithiole-3-thione is about 115 or about 100.

In one embodiment, the composition of the invention comprises:
- sulfobutylether-β-cyclodextrin, in an amount of about 10% (w/w), in weight relative to the total weight of the composition;
- 5-(4-methoxyphenyl)-3H-1,2-dithiole-3-thione at a concentration ranging from 0.1 to 0.7 mg/mL;
- Phosphate buffer in an amount ranging from 25 to 100 mM;

the molar ratio of the sulfobutylether-β-cyclodextrin to 5-(4-methoxyphenyl)-3H-1,2-dithiole-3-thione ranging from 90 to 120, preferably the molar ratio of the sulfobutylether-β-cyclodextrin to 5-(4-methoxyphenyl)-3H-1,2-dithiole-3-thione is about 115 or about 100.

Composition for Use/Method of Treating

The composition may be further formulated in the form of a pharmaceutical composition.

Thus, the invention further relates to a pharmaceutical composition comprising the composition of the invention In a third aspect, the invention relates to a composition, as previously described, for use as a drug.

In one embodiment, the composition is for use as an inhibitor of production of reactive oxygen species (ROS) in the treatment and/or prevention of free oxygen radical-related diseases.

In a third aspect, the invention relates to a method of preventing and/or treating a free oxygen radical-related disease. The method of the invention comprises a step of administering a therapeutically effective dose of the composition according to the invention, to a subject in need thereof.

In one embodiment, the method comprises administering an effective dose of the composition according to the invention by bolus injection.

In one embodiment, the method comprises administering an effective dose of the composition according to the invention by continuous infusion.

In one embodiment, the method comprises (a) administering an effective dose of the composition according to the invention by bolus injection to treat the acute phase of the disease, then (b) administering in a continuous way by infusion an effective dose of the composition according to the invention.

In one embodiment, the bolus injection is on the site of the acute manifestation of the disease. In one embodiment, the site is the myocardium. In one embodiment, the site is near the myocardium. In one embodiment, the bolus injection is via a catheter, preferably the catheter for angiography.

In one embodiment, the continuous infusion lasts at least one day, at least two days or at least three days.

Free oxygen radical-related diseases relate to oxidative stress imbalances and mitochondrial dysfunction. In particular, diseases related to mitochondrial dysfunctions are induced by mitochondrial ROS production.

In one embodiment, free oxygen radical-related diseases are selected from the group comprising cardiovascular diseases; aging diseases; auto-immune diseases; progeroid syndromes; Parkinsonian syndromes; neurological diseases; ischemic and reperfusion injuries; infectious diseases; muscles diseases; radiation effects, especially ionizing radiation effects; and lung, kidney and liver diseases.

Cardiovascular Diseases

Free oxygen radical-related cardiovascular diseases include, but are not limited to, hypertension, cardiac toxicity (including, cardiac toxicity of anthracyclines, cardiac toxicity of anti-cancer drugs, cardiac toxicity of quinolones and cardiac toxicity of antiviral drugs), heart failure regardless of origin, ischemia, ischemia-reperfusion injury, myocardial infarction, heart attack, stroke, atherosclerosis, cardiac fibrillation, hypertension, thrombosis and embolism, allergic/inflammatory conditions such as bronchial asthma, rheumatoid arthritis, inflammatory Bowel disease, type II diabetes, diabetes mellitus and deafness (DAD, also known as Ballinger-Wallace syndrome), inflammatory diseases, rheumatic fever, pulmonary arterial hypertension, syndromic cardiomyopathies (such as, Barth syndrome, Costello syndrome, Friedreich ataxia, LEOPARD syndrome, Noonan syndromes, cardiofaciocutaneous syndrome, cardioencephalomyopathy and Alstrom syndrome), innate immune responses and cardiopulmonary diseases such as chronic obstructive pulmonary disease, pulmonary embolism, pericarditis, coarctation of aorta, tetralogy of Fallot, aortic stenosis, mitral stenosis, aortic regurgitation, mitral regurgitation, pneumoconiosis, bronchiectasis, cardiomyopathies, peripheral artery disease (such as, arteriosclerosis, stenosis, aortoiliac occlusive disease, Degos disease, erythromelalgia, fibromuscular dysplasia and Raynaud's phenomenon) and/or endothelial nitroglycerin tolerance.

Aging Diseases

Free oxygen radical-related aging diseases include, but are not limited to, age-related macular degeneration (AMD), skin ageing, UV damage to the skin, thinning, sagging, wrinkling, the appearance of age spots, broken blood vessels and areas of dryness, seborrhoeic keratosis, solar keratoses, Kindler Syndrome, Bowen's disease, skin cancer, arthritis, ankylosing spondylitis, inflammatory polyarthropathies, knee arthritis, epidemic polyarthritis, psoriatic arthritis, cataract, deafness, cancer, metastasis, metastasis processes prevention, liver diseases, transplantation, neoplasms and toxicity of anti-neoplastic or immunosuppressive agents and chemicals, osteoporosis, poikiloderma, acrogeria, hereditary sclerosing poikiloderma, dyskeratosis congenita, xeroderma pigmentosum, Bloom's disease, Fanconi anemia, Cockayne syndrome and pollution-induced diseases.

Autoimmune Diseases

Free oxygen radical-related autoimmune diseases include, but are not limited to, multiple sclerosis, rheumatoid arthritis, systemic lupus erythematosis, type I diabetes mellitus, Crohn's disease; myasthenia gravis, Grave's disease, scleroderma, Sjogren's syndrome, ulcerative colitis, primary biliary cirrhosis, autoimmune hepatitis, Hashimoto's thyroiditis, ankylosing spondylitis, psoriasis.

The autoimmune disease can be an autoimmune disease related to blood disorders such as autoimmune hemolytic anemia, pernicious anemia and autoimmune thrombocytopenia.

The autoimmune disease can also be temporal arteritis, anti-phospholipid syndrome, vasculitides such as Wegener's granulomatosis and Behcet's disease.

Other autoimmune diseases include polymyositis, dermatomyositis, spondyloarthropathies such as ankylosing spondylitis, anti-phospholipid syndrome and polymyocysitis.

Progeroid Syndromes

Free oxygen radical-related progeroid syndromes include, but are not limited to, progeria, Bloom syndrome, Cockayne syndrome, De Barsy syndrome, dyskeratosis congenita, restrictive dermopathy, Rothmund-Thomson syndrome, trichothiodystrophy, Werner syndrome, Wiedemann-Rautenstrauch syndrome and xeroderma pigmentosum.

Parkinsonian Syndromes

Free oxygen radical-related parkinsonian syndromes include, but are not limited to, Parkinson's disease (PD), progressive supranuclear palsy, multiple system atrophy, corticobasal degeneration or Lewy body dementia, toxin-induced Parkinsonism, and an early-onset variant of PD such as an autosomal recessive PARK6-linked Parkinsonism or an autosomal recessive PINK1-linked Parkinsonism.

Neurologic Diseases

Free oxygen radical-related neurologic diseases include, but are not limited to, dementia, Alzheimer's disease, Parkinson's disease and ageing, Huntington's disease, Friedreich's Ataxia, Wilson's disease, Leigh syndrome, Kearns-Sayre syndrome, Leber hereditary optic neuropathy, cognitive disorders, mood disorders, movement disorders, tardive dyskinesia, brain injury, apoptosis, dementia, epilepsy, epileptic dementia, presenile dementia, post traumatic dementia, senile dementia, vascular dementia, HIV-1-associated dementia, post-stroke dementia, schizophrenia, Down's syndrome, motor neuron disease, amyloidosis, amyloid associated with type II diabetes, Creutzfelt-Jakob disease, necrotic cell death, Gerstmann-Straussler syndrome, kuru and animal scrapie, amyloid associated with long-term hemodialysis, senile cardiac amyloid and familial amyloidotic polyneuropathy, cerebropathy, neurospanchnic disorders, memory loss, aluminum intoxication, reducing the level of iron in the cells of living subjects, reducing free transition metal ion levels in mammals, patients having toxic amounts of metal in the body or in certain body compartments, multiple sclerosis, amyotrophic lateral sclerosis, akinetopsia, alcohol-related dementia, primary age-related tauopathy, anomic aphasia, anosognosia, apraxia, apraxia of speech, auditory verbal agnosia, frontotemporal dementia, frontotemporal lobar degeneration, logopenic progressive aphasia, neurofibrillary tangle, phonagnosia, Pick's disease, primary progressive aphasia, progressive nonfluent aphasia, semantic dementia, steroid dementia syndrome, visuospatial dysgnosia, ototoxic secondary effects of aminoglycosides and cocaine toxicity.

Ischemic and Reperfusion Injury

Free oxygen radical-related ischemic and reperfusion injury include, but are not limited to, stroke, brain ischemia, brainstem stroke syndrome, carotid endarterectomy, cerebellar stroke syndrome, cerebral achromatopsia, cerebral hemorrhage, cerebral infarction, cerebral venous sinus thrombosis, intraparenchymal hemorrhage, intracranial hemorrhage, lacunar stroke, lateral medullary syndrome, lateral pontine syndrome, partial anterior circulation infarct, posterior circulation infarct, silent stroke, stroke Association, stroke belt, stroke recovery, transient ischemic attack, Watershed stroke, Weber's syndrome, obesity, organ preservation for transplantation, ischemia and reperfusion injury.

Infectious Diseases

Free oxygen radical-related infectious diseases include, but are not limited to, hepatitis C, sepsis, infectious myopathies and septic shock.

Muscle Diseases

Free oxygen radical-related muscles diseases include, but are not limited to, myopathies, mitochondrial myopathies, facioscapulohumeral muscular dystrophy, facioscapulohumeral muscular dystrophy type 1, facioscapulohumeral muscular dystrophy type 2, Ryanodine Receptor 1 (RYR1) related myopathy, selenoprotein 1 (SEPN1)-related myopathy Kearns-Sayre syndrome, cardiomyopathies, movement disorder, immobilization-induced muscle atrophy, skeletal muscle burn injury and Dupuytren's contracture.

Lung, Kidney and Liver Diseases

Free oxygen radical-related lung, kidney and liver diseases include, but are not limited to, cystic fibrosis, asthma, pollution-induced diseases, cardio-pulmonary diseases, pulmonary arterial hypertension, chronic obstructive pulmonary disease, pulmonary embolism, pneumoconiosis, bronchiectasis, bronchial asthma, ventilator-induced diaphragm dysfunction, lung cancer, alcoholic fatty liver disease, nonalcoholic fatty liver disease, diabetes, kidney preservation ex vivo, liver inflammation in hepatitis C, kidney damage in type I diabetes and cirrhosis.

Radiation Effects

In one embodiment, the free oxygen radical-related diseases correspond to radiation effects, and especially ionizing radiation effects.

Radiation, and especially ionizing radiation, is classified as either electromagnetic or particulate. Whereas X and γ rays belong to electromagnetic radiation, energetic electrons, protons, neutrons, α particles and heavy charged particles are different forms of particulate radiation. In irradiated cells, such energy deposition causes endogenous bursts of ROS in and around the radiation track as well as in the intercellular matrix.

Exposure to ionizing radiation can be classified into 3 exposure situations. The first, planned exposure situations, results from the deliberate introduction and operation of radiation sources with specific purposes, as is the case with the medical use of radiation for diagnosis or treatment of patients, or the use of radiation in industry or research. The second type of situation, existing exposures, is where exposure to radiation already exists, and a decision on control must be taken—for example, exposure to radon in homes or workplaces or exposure to natural background radiation from the environment. The last type, emergency exposure situations, result from unexpected events requiring prompt response such as nuclear accidents or malicious acts.

Medical use of radiation accounts for 98% of the population dose contribution from all artificial sources, and represents 20% of the total population exposure. (WHO, fact sheets 2016)

Ionizing radiation effects include, but are not limited to, radiation injury, skin lesions, skin redness, hair loss, radiation burns, or acute radiation syndrome. Acute radiation syndrome comprises the symptoms of nausea, vomiting, diarrhea, headache, cognitive impairment, lethargy, ataxia, tremor, seizures, leukopenia, fatigue, purpura and hemorrhage.

Preferred Lists of Diseases to be Treated

In one embodiment, diseases to be treated in particular in the present invention are age-related macular degeneration, Parkinson's disease, Alzheimer's disease, ischemic and reperfusion injury, pulmonary arterial hypertension, scleroderma, atherosclerosis, heart failure, myocardial infarction, arthritis, pulmonary toxicity, cardiopulmonary diseases, inflammatory diseases, cancer, metastasis, cardiac toxicity (including, cardiac toxicity of anthracyclines, cardiac toxicity of anti-cancer drugs, cardiac toxicity of quinolones and cardiac toxicity of antiviral drugs), heart failure regardless of origin, ischemia, heart attack, stroke, thrombosis and embolism, asthma, allergic/inflammatory conditions, bronchial asthma, rheumatoid arthritis, Inflammatory Bowel Disease, Huntington's disease, cognitive disorders, Progeria, progeroid syndromes, epileptic dementia, presenile dementia, post traumatic dementia, senile dementia, vascular dementia, HIV-1-associated dementia, post-stroke dementia, Down's syndrome, motor neuron disease, amyloidosis, amyloid associated with type 2 diabetes, Creutzfelt-Jakob disease, necrotic cell death, Gerstmann-Straussler syndrome, kuru and animal scrapie, amyloid associated with long-term hemodialysis, senile cardiac amyloid and Familial Amyloidotic Polyneuropathy, cerebropathy, neurospanchnic disorders, memory loss, aluminum intoxication, reducing the level of iron in the cells of living subjects, reducing free transition metal ion levels in mammals, patients having toxic amounts of metal in the body or in certain body compartments, multiple sclerosis, amyotrophic lateral sclerosis, cataract, diabetes, cancer, liver diseases, skin ageing, transplantation, ototoxic secondary effects of aminoglycosides, neoplasms and toxicity of anti-neoplastic or immunosuppressive agents and chemicals, innate immune responses, and, Friedreich's Ataxia.

In one embodiment, diseases to be treated in particular in the present invention are free oxygen-radical-related cardiovascular diseases selected from the group comprising myocardial infarction, ischemia-reperfusion injury, cardiac toxicity (including, cardiac toxicity of anthracyclines, cardiac toxicity of anti-cancer drugs, cardiac toxicity of quinolones and cardiac toxicity of antiviral drugs, preferably, cardiac toxicity of anthracyclines), pulmonary arterial hypertension, heart failure, cardiac fibrillation, cardiopulmonary diseases, ischemia, heart attack, stroke, thrombosis and embolism, hypertension and cardiomyopathies.

In one embodiment, diseases to be treated in particular in the present invention are aging disease, AMD, skin aging, cardiovascular diseases such as, e.g., cardiac toxicity of anthracyclines, progeria and progeroid syndromes, Parkinson's disease, Alzheimer's disease, Friedreich's Ataxia, ischemia reperfusion, cardio-pulmonary diseases, asthma, cancer, metastasis and/or pollution-induced diseases.

In one embodiment, a disease to be particularly prevented and/or treated in the present invention is cardiac toxicity, preferably cardiac toxicity of anthracyclines. A mechanism responsible for anthracyclines toxicity refers to ROS production and site-specific DNA damage. Oxidative stress induction plays indeed a role in cardiac toxicity of anthracyclines by inducing DNA damage, sarcomere damage, mitochondrial dysfunction and loss of pro-survival signaling, mediating both death and survival of cardiomyocytes (Valcovici et al., 2016. *Arch Med Sci.* 12(2):428-35).

In one embodiment, a disease to be particularly prevented and/or treated in the present invention is pulmonary hypertension. Indeed, the deleterious effect of agents promoting ROS generation on pulmonary vasculature has been shown, and conversely, the beneficial effect of antioxidant agents in animal models of pulmonary hypertension. ROS production has thus been directly linked to pulmonary vascular remodeling, endothelial dysfunction, altered vasoconstrictive responses, inflammation and modifications of the extracellular matrix, all important features of pulmonary hypertension pathophysiology (Freund-Michel et al., 2013. *Ther Adv Respir Dis.* 7(3):175-200).

In one embodiment, a disease to be particularly prevented and/or treated in the present invention is ischemic and reperfusion injury. Indeed, excess production of ROS is a critical factor in the genesis of reperfusion injury (Granger et al., 2015. *Redox Biol.* 6:524-51).

In one embodiment, diseases to be treated in particular in the present invention are free oxygen radical-related liver diseases selected from the group comprising diabetes, alcoholic fatty liver disease, non-alcoholic fatty liver disease, liver inflammation in hepatitis C and cirrhosis.

In one embodiment, a disease to be particularly prevented and/or treated in the present invention is diabetes. Indeed, chronic hyperglycemia and subsequent augmentation of reactive oxygen species (ROS) deteriorate cell function and increase insulin resistance which leads to the aggravation of type 2 diabetes (Kaneto et al., 2010. *Mediators Inflamm.* 2010:453892), but also of other types of diabetes, such as MODY (Maturity Onset Diabetes of the Young).

In one embodiment, the composition, as previously described, is for use in increasing insulin secretion in a subject in need thereof, in particular for increasing glucose-stimulated insulin secretion (GSIS), such as in a subject affected with an insulin secretion deficiency, e.g., in a subject affected with a free oxygen radical-related liver disease as described above.

In one embodiment, the composition, as previously described, is for use in decreasing body weight and/or food intake in a subject in need thereof, in particular for decreasing body weight comprises decreasing fat mass and/or blood glucose levels in the subject in need thereof, such as in a subject affected with a free oxygen radical-related liver disease as described above and/or in a subject affected with dietary obesity.

In one embodiment, a disease to be particularly prevented and/or treated in the present invention is Parkinson disease. Indeed, mitochondrial dysfunction and oxidative damage, which results in increased production of ROS, are conditions often found in damaged brain areas of Parkinson's disease (Munoz et al., 2016. *Parkinsons Dis.* 2016:7049108).

In one embodiment, a disease to be particularly prevented and/or treated in the present invention is macular degeneration. Indeed, excessive ROS production and accumulation together with the oxidative stress, in particular in retinal pigment epithelium cells, plays a role in macular degeneration pathogenesis. ROS levels increase in the aging retina, leading to the oxidative stress and result in damage of photoreceptors, retinal pigment epithelium cells, and choriocapillaris in apoptosis process (Nita et al., 2016. *Oxid Med Cell Longev.* 2016:3164734).

In one embodiment, a disease to be particularly prevented and/or treated in the present invention is scleroderma. Indeed, NADPH oxidase, an important source of ROS, has been shown to be upregulated in scleroderma fibroblasts, resulting in large accumulations of ROS, which in turn plays a critical role in cell activation and DNA damage (Spadoni et al., 2015. *Arthritis Rheumatol.* 67(6):1611-22).

In one embodiment, a disease to be particularly prevented and/or treated in the present invention is metastasis. Indeed, ROS production is involved in mechanisms of tumor growth and metastasis: tumor cell migration, invasion, clonogenicity, metastatic take, and spontaneous metastasis are promoted by the natural selection of a mitochondrial phenotype associated with ROS production and aberrant TCA cycle activity, a mechanism named "metastatic mitochondrial switch" (Porporato et al., 2014. *Cell Reports.* 8(3):754-766). ROS hyper production also promotes angiogenesis and reciprocally inhibitors of ROS production are antiangiogenic products.

In a preferred embodiment, free oxygen radical-related diseases are selected from the group comprising cardiovascular diseases.

In one embodiment, cardiovascular diseases are selected from the group comprising myocardial infarction, ischemia-reperfusion injury, cardiac toxicity (including, cardiac toxicity of anthracyclines, cardiac toxicity of anti-cancer drugs, cardiac toxicity of quinolones and cardiac toxicity of antiviral drugs, preferably, cardiac toxicity of anthracyclines), pulmonary arterial hypertension, heart failure, cardiac fibrillation, cardiopulmonary diseases, ischemia, heart attack, stroke, thrombosis and embolism, hypertension and cardiomyopathies.

In a specific embodiment, the free oxygen radical-related disease to be prevented and/treated is myocardial infarction. In a specific embodiment, the free oxygen radical-related disease to be prevented and/treated is heart failure. In a specific embodiment, the free oxygen radical-related disease to be prevented and/treated is cardiac toxicity, preferably cardiac toxicity of anthracyclines, cardiac toxicity of anti-cancer drugs, cardiac toxicity of quinolones and/or cardiac toxicity of antiviral drugs, more preferably cardiac toxicity of anthracyclines. In a specific embodiment, the free oxygen radical-related disease to be prevented and/treated is pulmonary hypertension. In a specific embodiment, the free oxygen radical-related disease to be prevented and/treated is ischemia-reperfusion injury. In a specific embodiment, the free oxygen radical-related disease to be prevented and/treated is stroke.

In one embodiment, the prevention and/or treatment of free oxygen radical-related diseases is driven by inhibiting mitochondrial ROS production at site $I_Q$ of the mitochondrial complex I.

In one embodiment, the prevention and/or treatment of free oxygen radical-related diseases is driven without inhibiting cytosolic ROS production.

In one embodiment, the prevention and/or treatment of free oxygen radical-related diseases is driven by neutralizing ROS by an antioxidant effect.

Conservation Medium

Another object of the invention is a conservation medium or preservation medium comprising or consisting of or consisting essentially of the composition of the invention.

In one embodiment, the conservation medium is for the preservation of organs, biological tissues and/or living cells. In one embodiment, said organs include, but are not limited to, heart, liver, kidney, lung, pancreas, intestine, skin and cornea. In one embodiment, said organs are for transplantation, i.e., the transfer of any organ or body tissue from its site of origin to a recipient site. Specifically, in an allograft transplant procedure, the site of origin of the transplant is in a donor individual and the recipient site is in another, recipient individual.

Consistently, another object of the invention is a method for preserving organs, biological tissues and/or living cells, preferably before a transplantation procedure, comprising contacting said organs, biological tissues and/or living cells with the conservation medium or preservation medium of the invention.

Cosmetic/Cosmeceutical Compositions

The present invention also relates to a cosmetic composition comprising the composition of the invention.

The present invention also relates to a cosmeceutical composition comprising the composition of the invention.

Administration Modes

In one embodiment, the composition, the pharmaceutical composition or the drug of the invention is to be administered systemically or locally.

In one embodiment, the composition, the pharmaceutical composition or the drug of the invention is to be administered by injection, orally, topically, nasally, buccally, rectally, vaginaly, intratracheally, by endoscopy, transmucosally, or by percutaneous administration. In a preferred embodiment, the pharmaceutical composition or the drug of the invention is to be administered by injection.

Injection

In one embodiment, the composition, the pharmaceutical composition, the drug, the cosmetic composition or the cosmeceutical composition of the invention is to be injected, preferably systemically injected. Examples of formulations adapted to systemic injections include, but are not limited to, liquid solutions or suspensions, solid forms suitable for solution in, or suspension in, liquid prior to injection. Examples of systemic injections include, but are not limited to, intravenous, subcutaneous, intramuscular, intradermal and intraperitoneal injection, and perfusion.

In another embodiment, when injected, the composition, the pharmaceutical composition, the drug, the cosmetic composition or the cosmeceutical composition of the invention is sterile. Methods for obtaining a sterile pharmaceutical composition include, but are not limited to, GMP synthesis (GMP stands for "Good manufacturing practice").

In one embodiment, the composition, the pharmaceutical composition or the drug, of the invention is to be administered by injection. In one embodiment, the injection is a bolus injection. In one embodiment, the injection is a continuous infusion.

Oral Administration

In another embodiment, the composition, the pharmaceutical composition or the drug of the invention is to be orally administered. Examples of formulations adapted to oral administration include, but are not limited to, solid forms, liquid forms and gels. Examples of solid forms adapted to oral administration include, but are not limited to, pill, tablet, capsule, soft gelatine capsule, hard gelatine capsule, caplet, compressed tablet, cachet, wafer, sugar-coated pill, sugar coated tablet, or dispersing/or disintegrating tablet, powder, solid forms suitable for solution in, or suspension in, liquid prior to oral administration and effervescent tablet. Examples of liquid form adapted to oral administration include, but are not limited to, solutions, suspensions, drinkable solutions, elixirs, sealed phial, portion, drench, syrup and liquor.

Topical Administration

In another embodiment, the composition, the pharmaceutical composition or the drug composition of the invention is to be topically administered. Examples of formulations adapted to topical administration include, but are not limited to creams, gels, leave-on washes and/or the like.

Topical administration characterizes the delivery, administration or application of the composition, the pharmaceutical composition or the drug of the invention is directly to the site of interest for a localized effect (generally onto one or more exposed or outer surfaces thereof, such as the outermost layer of the epidermis, which is exposed and visually observable), e.g., using hands, fingers or a wide variety of applicators (roll-up, roll-on or other stick container, tube container, cotton ball, powder puff, Q-tip, pump, brush, mat, cloth and/or the like). The application may be made, e.g., by laying, placing, rubbing, sweeping, pouring, spreading and/or massaging into, or onto, the skin, or by any other convenient or suitable method.

Transdermal Administration

In one embodiment, the composition, the pharmaceutical composition or the drug of the invention can be administered as a transdermal patch, more particularly as a sustained-release transdermal patch. The transdermal patches can include any conventional form such as, e.g., adhesive matrix, polymeric matrix, reservoir patch, matrix or mono-lithic-type laminated structure, and are generally comprised of one or more backing layers, adhesives, penetration enhancers, an optional rate controlling membrane and a release liner which is removed to expose the adhesives prior to application. Polymeric matrix patches also comprise a polymeric-matrix forming material. Suitable transdermal patches are described in more detail in, e.g., U.S. Pat. Nos. 5,262,165, 5,948,433, 6,010,715 and 6,071,531, the disclosure of each of which are incorporated herein in their entirety.

Examples of formulations adapted to transdermal administration include, but are not limited to, ointment, paste, cream, film, balm, patch, such as, e.g., transdermal patch, gel, liposomal forms and the like.

In one embodiment, the transdermal composition is a patch, such as, e.g., transdermal patch, a gel or the like.

Ocular Administration

In another embodiment, a particular administration route may be intraocularly. In another embodiment, the administration route may be a topical ocular administration, such as, e.g., the administration of eye drops or by bathing the eye in an ophthalmic solution comprising the inhibitor of the invention.

The ophthalmic solution refers to sterile liquid, semi-solid or solid preparations intended for administration upon the eyeball and/or to the conjunctiva, or for insertion in the conjunctival sac or for administration into the posterior segment of the eye. As used herein, the term "posterior segment of the eye" refers to the back two third of the eye, comprising the anterior hyaloids membrane and the structures behind it (vitreous humor, retina, choroid, optic nerve). In particular, an ophthalmic composition may be administered into the vitreous, e.g., by intravitreous injection. Examples of ophthalmic compositions include, but are not limited to, eye drops, eye lotions, powders for eye drops and powders for eye lotions, and compositions to be injected into the conjunctival sac or into the vitreous.

Examples of carriers include, but are not limited to, water; buffered saline; natural polymers, such as, e.g., xanthanes, gelatin, cellulose, collagen, starch, or gum arabic; synthetic polymers; alcohols; polyols; and the like.

Delivery Systems

In one embodiment, the composition, the pharmaceutical composition or the drug of the invention may be used in conjunction with delivery systems that facilitate delivery of the agents to the central nervous system. For example, various blood brain barrier (BBB) permeability enhancers may be used to transiently and reversibly increase the permeability of the blood brain barrier to a treatment agent. Such BBB permeability enhancers include but are not limited to leukotrienes, bradykinin agonists, histamine, tight junction disruptors (e.g., zonulin, zot), hyperosmotic solutions (e.g., mannitol), cytoskeletal contracting agents, and short chain alkylglycerols (e.g., 1-O-pentylglycerol). Oral, sublingual, parenteral, implantation, nasal and inhalational routes can provide delivery of the active agent to the central nervous system. In some embodiments, the compounds of the present invention may be administered to the central nervous system with minimal effects on the peripheral nervous system.

The blood-brain barrier (BBB) is a physical barrier and system of cellular transport mechanisms between the blood vessels in the central nervous system (CNS) and most areas of the CNS itself. The BBB maintains homeostasis by restricting the entry of potentially harmful chemicals from the blood, and by allowing the entry of essential nutrients. However, the BBB can pose a formidable barrier to delivery of pharmacological agents to the CNS for treatment of disorders or maintaining or enhancing normal and desirable brain functions, such as cognition, learning, and memory.

Sustained-Release Administration

In one embodiment, the composition, the pharmaceutical composition, the drug, the cosmetic composition or the cosmeceutical composition of the invention is to be administered in a sustained-release form. In another embodiment, the composition, the pharmaceutical composition or the medicament comprises a delivery system that controls the release of the composition of the invention.

In one embodiment, the release of the composition is controlled by an electronic syringe.

Dosage Regimen

In one embodiment, the composition, the pharmaceutical composition, the drug, the cosmetic composition or the cosmeceutical composition of the invention is to be administered at a dose determined by the skilled artisan and personally adapted to each subject.

It will be understood that the total daily usage of the composition, the pharmaceutical composition, the drug, the cosmetic composition or the cosmeceutical composition of the invention will be decided by the attending physician within the scope of sound medical judgment. The specific therapeutically effective amount for any particular patient will depend upon a variety of factors including the disease being treated and the severity of the disease; the specific composition employed, the age, body weight, general health, sex and diet of the subject; the time of administration, route of administration, the duration of the treatment; drugs used in combination or coincidental with the composition, the pharmaceutical composition, the drug, the cosmetic composition or the cosmeceutical composition of the invention; and like factors well-known in the medical arts. For example, it is well within the skill of the art to start doses of a therapeutic compound at levels lower than those required to achieve the desired therapeutic effect and to gradually increase the dosage until the desired effect is achieved; but, at the opposite, it can be equally useful to start with a loading dose, a manner to reach steady-state plasma concentration more quickly, and then to follow with a maintenance dose calculated to exactly compensate the effect of the elimination process.

In one embodiment, a therapeutically effective amount of the composition, the pharmaceutical composition, the drug, the cosmetic composition or the cosmeceutical composition of the invention is to be administered at least once a day, twice a day, at least three times a day.

In another embodiment, a therapeutically effective amount of the composition, the pharmaceutical composition, the drug, the cosmetic composition or the cosmeceutical composition of the invention is to be administered every two, three, four, five, six days.

In another embodiment, a therapeutically effective amount of the composition, the pharmaceutical composition, the drug, the cosmetic composition or the cosmeceutical composition of the invention is to be administered twice a week, every week, every two weeks, once a month.

mg/day

In one embodiment, the daily amount of the composition, the pharmaceutical composition, the drug, the cosmetic composition or the cosmeceutical composition of the invention to be administered to a subject ranges from about 1 µg/day to about 100 mg/day, from about 1 µg/day to about 50 mg/day, from about 1 µg/day to about 10 mg/day, from about 1 µg/day to about 9 mg/day, from about 1 µg/day to about 8 mg/day, from about 1 µg/day to about 7 mg/day, from about 1 µg/day to about 6 mg/day, from about 1 µg/day to about 5 mg/day, from about 1 µg/day to about 4 mg/day, from about 1 µg/day to about 3 mg/day, from about 1 µg/day to about 2 mg/day, from about 1 µg/day to about 1 mg/day, from about 1 µg/day to about 100 µg/day.

In one embodiment, the daily amount of the composition, the pharmaceutical composition, the drug, the cosmetic composition or the cosmeceutical composition of the invention to be administered to a subject ranges from about 1 µg/day to about 10 mg/day, from about 5 µg/day to about 10 mg/day, from about 10 µg/day to about 7.5 mg/day, from about 10 µg/day to about 5 mg/day, from about 10 µg/day to about 2.5 mg/day, from about 10 µg/day to about 2 mg/day, from about 10 µg/day to about 1 mg/day, from about 10 µg/day to about 0.75 mg/day, from about 10 µg/day to about 0.5 mg/day, from about 10 µg/day to about 0.25 mg/day.

In one embodiment, the daily amount of the composition, the pharmaceutical composition, the drug, the cosmetic composition or the cosmeceutical composition of the invention to be administered to a subject ranges from about 0.1 mg/day to about 2000 mg/day, from about 0.1 mg/day to about 1500 mg/day, from about 0.1 mg/day to about 1000 mg/day, from about 0.1 mg/day to about 500 mg/day, from about 0.1 mg/day to about 200 mg/day, from about 0.5 mg/day to about 2000 mg/day, from about 0.5 mg/day to about 1500 mg/day, from about 0.5 mg/day to about 1000 mg/day, from about 0.5 mg/day to about 500 mg/day, from about 0.5 mg/day to about 200 mg/day, from about 1 mg/day to about 2000 mg/day, from about 1 mg/day to about 1500 mg/day, from about 1 mg/day to about 1000 mg/day, from about 1 mg/day to about 500 mg/day, from about 1 mg/day to about 200 mg/day.

In one embodiment, the daily amount of the composition, the pharmaceutical composition, the drug, the cosmetic composition or the cosmeceutical composition of the invention to be administered to a subject is about 1 µg/day, about 2 µg/day, about 4 µg/day, about 6 µg/day, about 8 µg/day, about 10 µg/day, about 15 µg/day, about 20 µg/day, about 25 µg/day, about 30 µg/day, about 35 µg/day, about 40 µg/day, about 45 µg/day, about 50 µg/day, about 55 µg/day, about 60 µg/day, about 65 µg/day, about 70 µg/day, about 75 µg/day, about 80 µg/day, about 85 µg/day, about 90 µg/day, about 95 µg/day, about 100 µg/day, about 150 µg/day, about 200 µg/day, about 250 µg/day, about 300 µg/day, about 350 µg/day, about 400 µg/day, about 450 µg/day, about 500 µg/day.

In one embodiment, the daily amount of the composition, the pharmaceutical composition, the drug, the cosmetic composition or the cosmeceutical composition of the invention to be administered to a subject is about 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1 mg/day, 2 mg/day, 4 mg/day, 6 mg/day, 8 mg/day, 10 mg/day, 15 mg/day, 20 mg/day, 25 mg/day, 30 mg/day, 35 mg/day, 40 mg/day, 45 mg/day, 50 mg/day, 75 mg/day, 100 mg/day, 125 mg/day, 150 mg/day, 175 mg/day, 200 mg/day, 300 mg/day, 400 mg/day, 500 mg/day, 600 mg/day, 700 mg/day, 800 mg/day, 900 mg/day, 1000 mg/day, 1200 mg/day, 1400 mg/day, 1600 mg/day, 1800 mg/day, 2000 mg/day.
mg/kg/day In one embodiment, the daily amount of the composition, the pharmaceutical composition, the drug, the cosmetic composition or the cosmeceutical composition of the invention to be administered to a subject ranges from about 0.1 µg/kg/day to about 10 mg/kg/day, from about 0.1 µg/kg/day to about 5 mg/kg/day, from about 0.1 µg/kg/day to about 1 mg/kg/day, from about 0.1 µg/kg/day to about 0.9 mg/kg/day, from about 0.1 µg/kg/day to about 0.8 mg/kg/day, from about 0.1 µg/kg/day to about 0.7 mg/kg/day, from about 0.1 µg/kg/day to about 0.6 mg/kg/day, from about 0.1 µg/kg/day to about 0.5 mg/kg/day, from about 0.1 µg/kg/day to about 0.4 mg/kg/day, from about 0.1 µg/kg/day to about 0.3 mg/kg/day, from about 0.1 µg/kg/day to about 0.2 mg/kg/day, from about 0.1 µg/kg/day to about 0.1 mg/kg/day, from about 0.1 µg/kg/day to about 10 µg/kg/day.

In one embodiment, the daily amount of the composition, the pharmaceutical composition, the drug, the cosmetic composition or the cosmeceutical composition of the invention to be administered to a subject ranges from about 0.1 µg/kg/day to about 1 mg/kg/day, from about 0.5 µg/kg/day to about 1 mg/kg/day, from about 1 µg/kg/day to about 0.75 mg/kg/day, from about 1 µg/kg/day to about 0.5 mg/kg/day, from about 1 µg/kg/day to about 0.25 mg/kg/day, from about 1 µg/kg/day to about 0.2 mg/kg/day, from about 1 µg/kg/day to about 0.1 mg/kg/day, from about 1 µg/kg/day to about 0.075 mg/kg/day, from about 1 µg/kg/day to about 0.05 mg/kg/day, from about 1 µg/kg/day to about 0.025 mg/kg/day.

In one embodiment, the daily amount of the composition, the pharmaceutical composition, the drug, the cosmetic composition or the cosmeceutical composition of the invention to be administered to a subject ranges from about 0.01 mg/kg/day to about 20 mg/kg/day, from about 0.01 mg/kg/day to about 15 mg/kg/day, from about 0.01 mg/kg/day to about 12 mg/kg/day, from about 0.01 mg/kg/day to about 10 mg/kg/day, from about 0.01 mg/kg/day to about 9 mg/kg/day, from about 0.01 mg/kg/day to about 8 mg/kg/day, from about 0.01 mg/kg/day to about 7 mg/kg/day, from about 0.01 mg/kg/day to about 6 mg/kg/day, from about 0.01 mg/kg/day to about 5 mg/kg/day, from about 0.01 mg/kg/day to about 4 mg/kg/day, from about 0.01 mg/kg/day to about 3 mg/kg/day, from about 0.01 mg/kg/day to about 2 mg/kg/day, from about 0.01 mg/kg/day to about 1 mg/kg/day.

In one embodiment, the daily amount of the composition, the pharmaceutical composition, the drug, the cosmetic composition or the cosmeceutical composition of the invention to be administered to a subject is about 0.1 µg/kg/day, about 0.2 µg/kg/day, about 0.4 µg/kg/day, about 0.6 µg/kg/day, about 0.8 µg/kg/day, about 1 µg/kg/day, about 1.5 µg/kg/day, about 2.0 µg/kg/day, about 2.5 µg/kg/day, about 3.0 µg/kg/day, about 3.5 µg/kg/day, about 4.0 µg/kg/day, about 4.5 µg/kg/day, about 5.0 µg/kg/day, about 5.5 µg/kg/day, about 6.0 µg/kg/day, about 6.5 µg/kg/day, about 7.0 µg/kg/day, about 7.5 µg/kg/day, about 8.0 µg/kg/day, about 8.5 µg/kg/day, about 9.0 µg/kg/day, about 9.5 µg/kg/day, about 10.0 µg/kg/day, about 15.0 µg/kg/day, about 20.0 µg/kg/day, about 25.0 µg/kg/day, about 30.0 µg/kg/day, about 35.0 µg/kg/day, about 40.0 µg/kg/day, about 45.0 µg/kg/day, about 50.0 µg/kg/day.

In one embodiment, the daily amount of the composition, the pharmaceutical composition, the drug, the cosmetic composition or the cosmeceutical composition of the invention to be administered to a subject is about 0.01 mg/kg/day, about 0.02 mg/kg/day, about 0.03 mg/kg/day, about 0.04 mg/kg/day, about 0.05 mg/kg/day, about 0.06 mg/kg/day, about 0.07 mg/kg/day, about 0.08 mg/kg/day, about 0.09 mg/kg/day, about 0.1 mg/kg/day, about 0.2 mg/kg/day, about 0.3 mg/kg/day, about 0.4 mg/kg/day, about 0.5 mg/kg/day, about 0.6 mg/kg/day, about 0.7 mg/kg/day, about 0.8 mg/kg/day, about 0.9 mg/kg/day, about 1 mg/kg/day, about 1.5 mg/kg/day, about 2 mg/kg/day, about 2.5 mg/kg/day, about 3 mg/kg/day, about 3.5 mg/kg/day, about 4 mg/kg/day, about 4.5 mg/kg/day, about 5 mg/kg/day, about 6 mg/kg/day, about 7 mg/kg/day, about 8 mg/kg/day, about 9 mg/kg/day, about 10 mg/kg/day, about 12 mg/kg/day, about 14 mg/kg/day, about 16 mg/kg/day, about 18 mg/kg/day, about 20 mg/kg/day.

In one embodiment, the composition, the pharmaceutical composition, the drug, the cosmetic composition or the cosmeceutical composition of the invention is to be administered at a quantity of about 1 µg to about 100 mg, from about 1 µg to about 50 mg, from about 1 µg to about 10 mg, from about 1 µg to about 9 mg, from about 1 µg to about 8 mg, from about 1 µg to about 7 mg, from about 1 µg to about 6 mg, from about 1 µg to about 5 mg, from about 1 µg to about 4 mg, from about 1 µg to about 3 mg, from about 1 µg to about 2 mg, from about 1 µg to about 1 mg, from about 1 µg to about 100 µg.

In one embodiment, the composition, the pharmaceutical composition, the drug, the cosmetic composition or the cosmeceutical composition of the invention is to be administered at a quantity of about 1 µg to about 10 mg, from about 5 µg to about 10 mg, from about 10 µg to about 7.5 mg, from about 10 µg to about 5 mg, from about 10 µg to about 2.5 mg, from about 10 µg to about 2 mg, from about 10 µg to about 1 mg, from about 10 µg to about 0.75 mg, from about 10 µg to about 0.5 mg, from about 10 µg to about 0.25 mg.

In another embodiment, the composition, the pharmaceutical composition, the drug, the cosmetic composition or the cosmeceutical composition of the invention is to be administered at a quantity of about 0.02 mg to about 2000 mg, from about 0.02 mg to about 1500 mg, from about 0.02 mg to about 1000 mg, from about 0.02 mg to about 500 mg, from about 0.02 mg to about 200 mg, from about 0.02 mg to about 100 mg, from about 0.02 mg to about 50 mg, from about 0.02 mg to about 25 mg, from about 0.02 mg to about 10 mg, from about 0.02 mg to about 5 mg.

In another embodiment, the composition, the pharmaceutical composition, the drug, the cosmetic composition or the cosmeceutical composition of the invention is to be administered at a quantity of about 0.02 mg, 0.04 mg, 0.06 mg, 0.08 mg, 0.1 mg, 0.2 mg, 0.3 mg, 0.4 mg, 0.5 mg, 0.6 mg, 0.7 mg, 0.8 mg, 0.9 mg, 1 mg, 1.5 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, 10 mg, 15 mg, 20 mg, 25 mg, 30 mg, 35 mg, 40 mg, 45 mg, 50 mg, 75 mg, 100 mg, 125 mg, 150 mg, 175 mg, 200 mg, 300 mg, 400 mg, 500 mg, 600 mg, 700 mg, 800 mg, 900 mg, 1000 mg, 1200 mg, 1400 mg, 1600 mg, 1800 mg, 2000 mg.

In one embodiment, the method of the invention is for a chronic treatment. In another embodiment, the method of the invention is for an acute treatment.

Subject

In one embodiment, the subject is diagnosed with a free oxygen radical-related disease. In another embodiment, the subject is at risk of developing a free oxygen radical-related disease.

In one embodiment, said subject is an adult, a teenager, a child, a young child or a new born child.

Kit-of Parts/Device

In a further aspect, the invention relates to a kit-of-parts comprising the invention of the invention.

In one embodiment, the kit-of-parts comprises a first container comprising the composition of the invention as previously described and a second container comprising a pharmaceutically acceptable excipient and/or carrier.

In one embodiment, the kit-of-parts comprises a first container comprising the composition of the invention comprising the compound of formula (I) and a cyclodextrin of formula (IV); and second container comprising a pharmaceutically acceptable aqueous excipient and/or carrier.

In one embodiment, the kit-of-parts comprises a first container comprising the composition of the invention comprising the compound of formula (I) and a cyclodextrin of formula (IV); and second container comprising a pharmaceutically acceptable aqueous excipient and/or carrier.

In one embodiment, the kit-of-parts comprises a first container comprising the composition of the invention comprising the compound of formula (I) selected from 5-(4-methoxyphenyl)-3H-1,2-dithiole-3-thione; 5-(4-hydroxyphenyl)-3H-1,2-dithiole-3-thione; 5-(4-hydroxyphenyl)-3H-1,2-dithiol-3-one; 5-(4-hydroxyphenyl)-3H-1,2-dithiol-3-one oxime; 5-(4-hydroxyphenyl)-3H-1,2,4-dithiazole-3-thione; 4-(4-hydroxyphenyl)-3H-1,2-dithiole-3-thione; 5-(2-hydroxybenzo[d]oxazol-5-yl)-3H-1,2-dithiole-3-thione; 5-(2-hydroxybenzo[d]thiazol-6-yl)-3H-1,2-dithiole-3-thione; 5-(benzofuran-5-yl)-3H-1,2-dithiole-3-thione; and methyl 5-(3-thioxo-3H-1,2-dithiol-5-yl)-1H-indole-1-carboxylate and a cyclodextrin of formula (IV); and second container comprising a pharmaceutically acceptable aqueous excipient and/or carrier.

In one embodiment, the kit-of-parts comprises a first container comprising the composition of the invention comprising:
  a compound of formula (I) selected from 5-(4-methoxyphenyl)-3H-1,2-dithiole-3-thione; 5-(4-hydroxyphenyl)-3H-1,2-dithiole-3-thione; 5-(4-hydroxyphenyl)-3H-1,2-dithiol-3-one; 5-(4-hydroxyphenyl)-3H-1,2-dithiol-3-one oxime; 5-(4-hydroxyphenyl)-3H-1,2,4-dithiazole-3-thione; 4-(4-hydroxyphenyl)-3H-1,2-dithiole-3-thione; 5-(2-hydroxybenzo[d]oxazol-5-yl)-3H-1,2-dithiole-3-thione; 5-(2-hydroxybenzo[d]thiazol-6-yl)-3H-1,2-dithiole-3-thione; 5-(benzofuran-5-yl)-3H-1,2-dithiole-3-thione; and methyl 5-(3-thioxo-3H-1,2-dithiol-5-yl)-1H-indole-1-carboxylate, and
  hydroxypropyl-β-cyclodextrin;
and second container comprising a pharmaceutically acceptable aqueous excipient and/or carrier.

In one embodiment, the kit-of-parts comprises a first container comprising the composition of the invention comprising:
  a compound of formula (I) selected from 5-(4-methoxyphenyl)-3H-1,2-dithiole-3-thione; 5-(4-hydroxyphenyl)-3H-1,2-dithiole-3-thione; 5-(4-hydroxyphenyl)-3H-1,2-dithiol-3-one; 5-(4-hydroxyphenyl)-3H-1,2-dithiol-3-one oxime; 5-(4-hydroxyphenyl)-3H-1,2,4-dithiazole-3-thione; 4-(4-hydroxyphenyl)-3H-1,2-dithiole-3-thione; 5-(2-hydroxybenzo[d]oxazol-5-yl)-3H-1,2-dithiole-3-thione; 5-(2-hydroxybenzo[d]thiazol-6-yl)-3H-1,2-dithiole-3-thione; 5-(benzofuran-5-yl)-3H-1,2-dithiole-3-thione; and methyl 5-(3-thioxo-3H-1,2-dithiol-5-yl)-1H-indole-1-carboxylate, and
  sulfobutylether-β-cyclodextrin; the molar ratio of the sulfobutylether-β-cyclodextrin to the compound of formula (I) ranging from 2.5 to 400, from 10 to 400, preferably from 57 to 200, even more preferably from 60 to 160;
and second container comprising a pharmaceutically acceptable aqueous excipient and/or carrier.

In one embodiment, the kit-of-parts comprises a first container comprising the composition of the invention comprising:
  a compound of formula (I) selected from 5-(4-methoxyphenyl)-3H-1,2-dithiole-3-thione and 5-(4-hydroxyphenyl)-3H-1,2-dithiole-3-thione, and
  sulfobutylether-β-cyclodextrin; the molar ratio of the sulfobutylether-β-cyclodextrin to the compound of formula (I) ranging from 2.5 to 400, from 10 to 400, preferably from 57 to 200, even more preferably from 60 to 160;
and second container comprising a pharmaceutically acceptable aqueous excipient and/or carrier.

In one embodiment, the kit-of-parts comprises a first container comprising the composition of the invention comprising:
  5-(4-hydroxyphenyl)-3H-1,2-dithiole-3-thione, and
  sulfobutylether-β-cyclodextrin; the molar ratio of the sulfobutylether-β-cyclodextrin to the compound of formula (I) ranging from 2.5 to 400, from 10 to 400, preferably from 57 to 200, even more preferably from 60 to 160;
and second container comprising a pharmaceutically acceptable aqueous excipient and/or carrier.

In one embodiment, the kit-of-parts comprises a first container comprising the composition of the invention comprising:
  5-(4-methoxyphenyl)-3H-1,2-dithiole-3-thione, and
  sulfobutylether-β-cyclodextrin; the molar ratio of the sulfobutylether-β-cyclodextrin to the compound of formula (I) ranging from 2.5 to 400, from 10 to 400, preferably from 57 to 200, even more preferably from 60 to 160;
and second container comprising a pharmaceutically acceptable aqueous excipient and/or carrier.

In one embodiment, the pharmaceutically acceptable aqueous carrier of the second container is an aqueous solution.

In one embodiment, the pharmaceutically acceptable aqueous excipient comprises or essentially consists of a polysorbate selected from polysorbate 80, polysorbate 20 and mixtures thereof.

In one embodiment, the polysorbate selected from polysorbate 80, polysorbate 20 and mixtures thereof, is in an amount ranging from 1 to 40% (w/w), from 1 to 30% (w/w), from 1 to 20% (w/w), preferably 2 to 15% (w/w), in weight relative to the total aqueous excipient composition.

In one embodiment, the compositions of both the first and the second container are liquid compositions.

In one embodiment, the composition of the first container is solid, preferably a powder composition and the composition of the second container is a liquid aqueous composition.

The two containers may be physically isolated or interconnected by an intermediate retractable separating surface.

Thus, the operator may mix the composition of the first and the second container manually in a third container or delivery device. Alternatively, the operator may mix the composition of the first and the second container within the interconnected container system by removing the retractable separating surface.

In a further aspect, the invention relates to a device, preferably a delivery device, comprising the composition, the pharmaceutical composition or the kit-of-parts according to the invention. The device may therefore be a delivery device such as for example a prefilled syringe. In one embodiment, the prefilled syringe comprises a composition or a pharmaceutical composition of the invention. In one embodiment, the prefilled syringe comprises the two containers of the kit-of-parts of the invention. The composition of the two containers being mixed prior to the operation of the delivery device.

Method for Solubilizinig a Compound of Formula (I)

In a last aspect, the invention relates to a method for solubilizing a compound of formula (I) in an aqueous medium.

In one embodiment, the method comprising the steps of mixing the compound of formula (I) with a cyclodextrin of formula (IV), in a molar ratio of cyclodextrin to compound of formula (I) ranging from 10 to 400, preferably from 30 to 200.

In one embodiment, the method comprising the steps of mixing the compound of formula (I) with sulfobutylether-beta-cyclodextrin, in a molar ratio of cyclodextrin to compound of formula (I) ranging from 10 to 400, preferably from 57 to 200.

In one embodiment, the method comprising the steps of mixing the compound of formula (I) with hydroxypropyl-beta-cyclodextrin, in a molar ratio of cyclodextrin to compound of formula (I) ranging from 10 to 400, preferably from 30 to 200.

In one embodiment, the method further optionally comprises adding a co-solvent selected from polysorbates, preferably polysorbates selected from polysorbate 80 and polysorbate 20, even more preferably the co-solvent is polysorbate 80. In one embodiment, the amount of co-solvent is as previously described.

In one embodiment, the method comprises the steps of:
a) mixing the compound of formula (I) with a cyclodextrin of formula (IV), in a molar ratio of cyclodextrin: compound of formula (I) ranging from 10 to 400, preferably 30 to 200; then
b) freeze-drying or spray-drying, preferably freeze-drying the mix obtained in step (a) leading to the obtention of a powder; then
c) reconstituting the powder of step (b) in an aqueous medium.

In one embodiment, the mixing of step (a) is in a spray-drying compatible solvent system. In another embodiment, the mixing of step (a) is in a freeze-drying compatible solvent system.

In one embodiment, the compound of formula (I) and the cyclodextrin of formula (IV) are mixed at a temperature ranging from 20° C. to 80° C., preferably from 20° C. to 70° C., more preferably from 20° C. to 35° C., preferably from 20° C. to 30° C.

In one embodiment, the compound of formula (I) and the cyclodextrin of formula (IV) are mixed at a temperature ranging from 20° C. to 35° C., preferably 20 to 30° C. for 1 to 96 hours, for 3 to 72 hours, for 6 to 48 hours, for 4 to 40 hours, for 3 to 36 hours, for 3 to 30 hours, for 3 to 24 hours or for 3 to 20 hours.

In one embodiment, the compound of formula (I) and the cyclodextrin of formula (IV) are mixed at a temperature of about 70° C. for 3 hours. In one embodiment, the compound of formula (I) and the cyclodextrin of formula (IV) are mixed at a temperature of about 70° C. for 1 hour. In one embodiment, the compound of formula (I) and the cyclodextrin of formula (IV) are mixed at room temperature (about 25° C.) for a mixing time ranging from about 1 hour to about 3 hours.

The mixing can take place by any means for mixing known in the art. In one embodiment, the mixing is a magnetic stirring. In one embodiment, the mixing is a trituration.

In one embodiment, the mixing step (a) is by magnetic stirring, high-shear mixing or sonication.

In one embodiment, the mixing step (a) is under inert gas environment. In one embodiment, the inert gas is $N_2$. In one embodiment, the mixing step (a) is under $N_2$ gas flux.

In one embodiment, the aqueous medium of step (c) is pure water.

In one embodiment, the aqueous medium of step (c) is saline water for injection (i.e., NaCl 0.9% w/v, preferably sterile NaCl 0.9% w/v).

In one embodiment, the reconstitution of the powder (c) is made in an aqueous medium optionally comprising at least one co-solvent selected from polysorbates, preferably polysorbates selected from polysorbate 80 and polysorbate 20, even more preferably the at least one co-solvent is polysorbate 80.

The invention further relates to a composition obtainable from the solubilization method of the present invention.

In one embodiment, the composition is directly obtained from the solubilization method of the present invention.

EXAMPLES

The present invention is further illustrated by the following examples.

Abbreviations

AOL: anethole trithione
AOL/HP-β-CD: anethole trithione mixture with hydroxypropyl-β-cyclodextrin
AOL/SBE-β-CD: anethole trithione mixture with sulfobutylether-β-cyclodextrin
CD: cyclodextrin.
DCM: dichloromethane
EtOH: ethanol
H(U)PLC: High (Ultra) performance liquid chromatography
HP-β-CD: hydroxypropyl-β-cyclodextrin
m/z: mass number/charge number of a mass spectrometry fragment
$Me_2CO$: acetone
MeOH: methanol
min: minutes
$R_M$: designates the molar ratio of the cyclodextrin in the solution over the solubilized solute
$R_m$: designates the weight ratio of the cyclodextrin in the solution over the solubilized solute
s designates seconds
$S/S_0$: designates the ratio of the AOL solubility relative to the intrinsic solubility of AOL in water
SBE-β-CD: sulfobutylether-β-cyclodextrin (also referred to as SBE)

$T_R$: retention time of a compound in a chromatography column v/v: concentration of a compound/solvent in volume relative to the total volume of the composition comprising said compound/solvent w/w: concentration of a compound/solvent in weight relative to the total weight of the composition comprising said compound/solvent α-CD: α-cyclodextrin β-CD: β-cyclodextrin γ-CD: γ-cyclodextrin Materials and Methods Materials Standard compounds we supplied as follows: Trithioanethole (AOL, M2I; Ref. 0000032766; Lot. IL97A81-1 or OP2 Drugs SAS batch GIG201747), trithioanole (M2I; Ref. 0000032781; Lot. JJ15C168-A), thioamide (M2I; Ref. 0000032782; Lot. SDM-14O-015), trans-anethole (Sigma; Ref. PHR1218-2,2ML; Lot. LRAA9031).

Formulation vehicles we supplied as follows: Captisol β-cyclodextrin SBE sulfobutyl ethers (CYDEX; Lot. NC-04A-11071, DS 6.4), Kleptose HPB hydroxypropyl β-cyclodextrin (ROQUETTE; Ref. 772607), Propylene glycol (COOPER; Lot. 11060089/M), Polyethylene glycol, PEG 200 (ACROS; Ref. 19221; Lot. A0227337), Polyethylene glycol, PEG 400 (ACROS; Ref. 19223; Lot. A0210931001), Polyethylene glycol, PEG 600 (ACROS; Ref. 19224; Lot. A0222645), Polyethylene glycol, PEG 20000 (SIGMA; Ref. 81275; Lot. BCBS2337V), Polysorbate 20 (ACROS; Ref. 23336; Lot. A0204618001), Polysorbate 80 (ACROS; Ref. 27863; Lot. A0245809).

Solvents: Ultra-pure water was obtained by MERCK MILLIPORE Milli-Q® Gradient model; Methanol (FISHER; Ref. M/4058/17; Lot. 1417312); Dichloromethane Chem-lab 22.4522701; Ethanol Chem-lab 23.5652406; Ethyl acetate Sigma Aldrich SZBF135MV; NaOH pellets Acros 1414713; Potassium dihydrogen phosphate VWR 17C164123;

Methods

HPLC-System

DIONEX Ultimate 3000 U(H)PLC equipped with an LPG-3400-RS pump; an automatic injector WPS-3000-RS; a heated column chamber TCC-3000-SD; and a diode-array UV-Visible detector.

The HPLC system was monitored by Chromeleon™ version 6.8 software.

HPLC Conditions

Column: PHENOMENEX Prodigy® ODS (3), 3 µm, 150×2.00 mm; mobile phase: methanol/water (80:20 v/v); temperature: 30° C.; flow: 0.2 mL/min; injection volume: 1 µL; UV detection: 230 nm and 350 nm; run time: 8 min.

Solubility Testing in Solvents for Spray-Drying

First, the solubility of the SBE-β-CD was visually determined in seven combinations of solvents:

Methanol/dichloromethane 90/10 (w/w);

Methanol/ethyl acetate 90/10 (w/w);

Ethanol/water 10/90 (w/w);

Acetone/water 50/50 and 75/25 (w/w); and

Acetonitrile/water 50/50 and 75/25 (w/w).

For the solvent/water mixtures, 0.2 g of SBE-β-CD was added to the media at a 10 g scale with a start concentration of 2% w/w. If SBE-β-CD was completely dissolved (visual inspection), more SBE-β-CD was added stepwise until a concentration of 10% w/w or visual saturation of the test medium was obtained.

For the solvent mixtures, 0.1 g of SBE-β-CD was added to the media at a 10 g scale with a start concentration of 1% w/w. If SBE-β-CD was completely dissolved (visual inspection), more SBE-β-CD was added stepwise until a concentration of 20% w/w or visual saturation of the test medium was obtained.

Then, the solubility of AOL was evaluated in the selected media containing solvents and SBE-β-CD, by adding stepwise AOL to the media. Samples were mixed using a magnetic stirrer in closed SEPAC clear bottles. Batch scales were depending of the solvent mixtures composition used:

50 g for EtOH/H$_2$O mixture containing 10% SBE-β-CD and for acetone/H$_2$O mixture containing 10% SBE-β-CD 100 g for ACN/H$_2$O mixture containing 4% of SBE-β-CD 200 g for ACN/H$_2$O mixture containing 2% of SBE-β-CD, MeOH/DCM mixture containing 1.5% SBE-β-CD and MeOH/ethyl acetate mixture containing 1.5% SBE-β-CD Solubility was determined by visual inspection. These experiments were carried out at room temperature under yellow light. Each medium was tested in a single sample only (n=1).

Spray-Drying

Solid dispersions are prepared by spray-drying of a feed solution using a lab scale spray-dryer, type B 290 inert loop (Buchi, Flawil, Switzerland). The feed solution is fed to a two-fluid nozzle (orifice diameter: 0.7 mm) at the top of the spray dryer by means of a peristaltic pump, type 520U (Watson Marlow, Cornwall, UK). The spray dryer is operated in co-current air flow mode. To limit oxidative degradation, compressed nitrogen was used as atomizing gas instead of air. The applied process parameters are summarized in Table 1. The spray-dried particles are collected in a reservoir attached to a cyclone, where they are cooled down to room temperature.

TABLE 1

Spray-drying conditions

| Process parameters | Setting/reading during spray-drying of AOL/SBE in: | | |
|---|---|---|---|
| | Acetone/H$_2$O | MeOH/DCM | H$_2$O |
| Inlet drying nitrogen temperature (° C.) | 97-103 | 87-95 | 97-103 |
| Outlet drying nitrogen temperature (° C.) | 48-53 | 46-49 | 51.53 |
| Condenser temperature (° C.) | 10 | −20 | NA |
| Drying nitrogen aspirator (%) | 100 | 100 | 100 |
| Atomising nitrogen pressure (bar) | 0.3 | 0.3 | 0.3 |
| Feed spray rate (g/min) | 5.5-5.8 | 6.0-6.3 | 2.5-2.6 |
| Oxygen concentration (%) | <6 | <6 | NA |

The spray-dried powders were collected in ambers glass vials and, due to timing issues, first stored at 2-8° C. for at least 48 hours, before transferring to a Heraeus vacuum oven type VT6060M (Thermo Fisher Scientific Inc., MA, USA) in order to remove residual solvents. The powders were dried at a temperature of 25° C. under vacuum (<300 mbar) using nitrogen flushing for 16 hours.

Assay and purity of spray-dried powders were determined using HPLC as previously described.

Aqueous Reconstitution of the Spray-Dried Powders

Aqueous solutions of the obtained powders were prepared. In order to assess the effect of solid dispersions containing AOL on the solubility in purified water, varying amounts of the solid dispersions were added to 10 mL glass vials containing either 2.5 mL or 3.3 mL of water or Tween 80 (10% and 20% w/w) aqueous solutions in order to obtain the different targeted ratios.

The stability of the solutions was evaluated in function of time over 48 hours by visual inspection.

Freeze-Drying 10 mL Adelphi® vials were filled with 5 mL of AOL solution. 20 mm Freeze Dry stoppers (Grey RTS Silicone A) were used to enable the moisture extraction during the lyophilization process. The lyophilization run was performed with the Telstar Lyobeta 6PL freeze drier, equipped with a 316 L stainless steel chamber, a condenser with a minimum temperature below −80° C., a condensation capacity of 30 kg of ice and a vacuum pump which can reach <20 mbar. The Telstar 6PL was equipped with an external Julabo FL4003 cooling unit.

The lyophilization run was monitored using Lyobeta Lyosuitelab 3.0 software. The samples were loaded in the freeze drier at a shelf temperature of 20° C. To initiate the freezing step, the shelves were cooled to −40° C. with a ramp rate of 1° C./min. After maintaining this temperature for 6 hours, the pressure in the drying chamber was lowered from the atmospheric pressure until 100 µbar. The Primary drying stage was performed by increasing the temperature to −20° C. and maintaining this temperature for 40 hours. During the second drying stage, the pressure was lowered below 20 µbar and the shelf temperature was increased up to 25° C. These conditions were maintained for 20 hours, followed by stoppering of the vials. After closing the vials under vacuum, the chamber was aerated until atmospheric pressure. The vials were removed from the drying chamber and capped with aluminum Complete Tear-Off Seals (Adelphi®).

Determination of the Reconstitution Time of the Dried Cakes

The time of reconstitution, (i.e., the time required to disperse the solid cake into its reconstituted solution after addition of a liquid), is determined by addition of a certain amount of purified water Type I or 0.9% NaCl solution to target a certain final concentration of AOL. The time needed to obtain a clear solution is tracked.

Results

Example 1: Incompatibility of AOL with Lipid Carriers 100 mg of AOL were successfully dissolved in 20 mL of polyglyceryl-3 dioleate (Plurol® Oleique). A homogenous vividly orange colored solution was obtained with less than 5 minutes of magnetic stirring.

Visual examination of the obtained solution after 24 hours at room temperature revealed an intense color change. The obtained solution turned greed with obvious aspect and odor having turned rancid.

100 mg of AOL were successfully dissolved in 20 mL of 2-[2,3-bis(2-hydroxyethoxy)propoxy]ethanol; hexadecanoic acid; octadecanoic acid (Labrafil® M1944). A homogenous orange colored solution was obtained with less than 5 minutes of magnetic stirring.

Visual examination of the obtained solution after 24 hours at room temperature revealed an intense color change. The obtained solution turned dark green.

A new solution of 5 mg/mL AOL in Labrafil® M1944 and stocked in a hermetically closed recipient. Visual examination of the obtained solution after 24 hours at room temperature revealed the same stability problem.

Thus, the presence of oxygen does not interfere with the stability of AOL in lipid carriers.

Solubilization of AOL with lipid carriers was effective in less than 5 minutes of mild stirring. Nevertheless, AOL was unstable within such carriers and in the period of 24 hours was degraded, as evidenced by visual observation of the obtained solution.

Example 2: AOL Quantitative Analysis Method

Standard solutions of AOL, trithioanole, thioamide and trans-anethole were prepared in methanol.

Then, 3 solutions containing a mixture of the standards in 0.4, 1.0 and 2.0 mg/mL respectively. The chromatographic analysis of such mixture is presented in FIG. 1.

Under the HPLC conditions used, AOL, trithioanole, thioamide and trans-anethole showed a retention time of 2.92, 3.75, 5.71 and 6.56 minutes respectively. The resolution of the chromatographic conditions applied qualifies them as specific for the compounds' analysis.

Three control solutions of each of the 4 reference standards were prepared at concentrations of 10, 25 and 50 mg/mL and analyzed in the same HPLC conditions.

The regression lines and correlation coefficients were calculated as follows:

Trithioanethole: y=0.2546x−0.1165; $R^2$ 0.9999

Trithioanole: y=0.2455x−0.202; $R^2$ 1,0000

Thioamide: y=0.1971x+0.2431; $R^2$ 1,0000 trans-Anethole: y=0.1229x−0.0083; $R^2$ 1,0000

All correlation coefficients were superior to 0.999 and the linearity of the response to the standard compounds was shown in the concentration range of 10 to 50 mg/mL.

The accuracy of the quantitative analysis was measured on the overlap between the known concentration test solutions and the theoretical calculation based on the calculated regression lines.

Individual compound overlap was between 99.5% and 100.8%. Thus, the quantitative analysis method is accurate.

Example 3: Cyclodextrins Enhance the Solubility of AOL

This assay evaluated the potential of different cyclodextrins to solubilize AOL. A solubilization screening is carried out with the four cyclodextrins (CD) selected from α-CD, γ-CD, HP-β-CD and SBE-β-CD.

Aqueous solutions containing 100 mM of cyclodextrin are prepared in pure water. An excess of AOL (approximately 5 mg/mL) is suspended in 2 mL of each of these cyclodextrin solutions. Each duplicate sample is shaken at 25° C. for 3 hours and 20 hours (vortex to 1400 rpm). Each sample is centrifuged (12,500 g) then filtered through a 0.45 μm membrane. The solubility of the AOL is quantified by HPLC as previously described (Example 2). Results are given in Table 2.

TABLE 2

Results of cyclodextrin solubilization screening.

| CD | Stirring time | AOL Solubility (mg/L) | $R_M$[a] | $R_m$[b] | $S/S_0$[c] |
|---|---|---|---|---|---|
| None-$H_2O$ | 3 h | 0.22 | — | — | — |
| | 20 h | 0.16 | — | — | — |
| α-CD | 3 h | 8.83 | 2721 | 11010 | 41 |
| | 20 h | 13.51 | 1779 | 7198 | 87 |
| γ-CD | 3 h | 2.86 | 8399 | 45316 | 13 |
| | 20 h | 1.67 | 14405 | 77723 | 11 |

TABLE 2-continued Results of cyclodextrin solubilization screening.

| CD | Stirring time | AOL Solubility (mg/L) | $R_M{}^a$ | $R_m{}^b$ | $S/S_0{}^c$ |
|---|---|---|---|---|---|
| HP-β-CD | 3 h | 110.19 | 218 | 1270 | 510 |
|  | 20 h | 95.52 | 252 | 1465 | 617 |
| SBE-β-CD | 3 h | 142.3 | 169 | 1575 | 659 |
|  | 20 h | 160.74 | 150 | 1395 | 1038 |

[a] $R_M$ designating the molar ratio of the cyclodextrin in the solution over the solubilized solute.
[b] $R_m$ designating the weight ratio of the cyclodextrin in the solution over the solubilized solute.
[c] $S/S_0$ designating the ratio of the AOL solubility relative to the intrinsic solubility of AOL in water.

The solubilization equilibrium seems to be reached quite rapidly because the results after 3 hours and 20 hours stirring are comparable.

The intrinsic solubility of AOL in water at 25° C. was estimated at approximately 0.2 mg/L. The two cyclodextrins that appear to have sufficient affinity to solubilize the AOL are HP-β-CD and SBE-β-CD.

The solubility of AOL has been multiplied by 600 with HP-β-CD and per 1000 with SBE-β-CD.

Without willing to be bound by a theory, the relatively large values of the molar ratios calculated for these two cyclodextrins suggest weak interactions with AOL. The solubilization of the solute preferentially may pass through the formation of complex association (interaction outside the cavity) to the detriment of the formation of inclusion complexes (interaction inside the cavity). Cyclodextrins will rather behave with AOL as solvating agents and not as a stable complex that can significantly modify the physicochemical properties and the bioavailability of AOL.

Example 4: Cyclodextrin—AOL Solubility Diagrams

A cyclodextrin-AOL solubility diagram would reveal the profile of the solubility curve of the AOL depending on the concentration of the cyclodextrin. The principle of this method is to add an excess of AOL to cyclodextrin solutions of increasing concentration, then to measure the amount of solubilized AOL. This method confirms the solubilization and evaluates more precisely the cyclodextrin solubilizing power, to define a stoichiometry of the complexes (molar and mass ratios) over the entire range of concentrations studied and to estimate the solubility limit and the stability of the mixtures.

The solubilization was carried out with HP-β-CD and SBE-β-CD in a range of concentration ranging from 2.5% to 40% (m/m) at 20° C., 25° C. and 30° C. To check the stability of the solution, a storage test at 4° C. for 48 hours was carried out with the solutions previously prepared at 20° C.

Aqueous solutions of cyclodextrin at in weight (m/m) concentrations of 2.5%, 5%, 10%, 20%, 30% and 40% were prepared in pure water. An excess of AOL was suspended in 2 mL each of these solutions. Each sample is shaken at 20° C., 25° C. or 30° C. for 4 hours (vortex at 1400 rpm). Each sample is centrifuged (12,500 g) and filtered through a 0.45 μm membrane.

The solubility of AOL in each test solution was quantified by HPLC as detailed in Example 2. Results are given in Tables 3 and 4.

TABLE 3

Solubility of AOL relative to the HP-β-cyclodextrin (HP-β-CD) and the temperature.

| Solubilization T° | CD | CD % (w/w) | AOL solubility mg/L | $S/S_0$ | CD/AOL ratio $R_m$ | $R_M$ |
|---|---|---|---|---|---|---|
| 20° C. | None | 0 | 0 | — | — | — |
|  | HP-β-CD | 2.5 | 13.4 | 34 | 1866 | 200 |
|  |  | 5 | 27.3 | 68 | 1832 | 196 |
|  |  | 10 | 61.3 | 153 | 1631 | 175 |
|  |  | 20 | 144.8 | 362 | 1381 | 148 |
|  |  | 30 | 243 | 608 | 1235 | 132 |
|  |  | 40 | 344.2 | 861 | 1162 | 124 |
| 25° C. | None | 0 | — | — | — | — |
|  | HP-β-CD | 2.5 | 19.5 | 49 | 1282 | 137 |
|  |  | 5 | 40.1 | 100 | 1247 | 133 |
|  |  | 10 | 83.9 | 210 | 1192 | 128 |
|  |  | 20 | 184.2 | 46 | 1086 | 116 |
|  |  | 30 | 287.4 | 719 | 1044 | 112 |
|  |  | 40 | 417.5 | 1044 | 958 | 103 |
| 30° C. | None | 0 | — | — | — | — |
|  | HP-β-CD | 2.5 | 26.1 | 65 | 958 | 103 |
|  |  | 5 | 51.4 | 129 | 973 | 104 |
|  |  | 10 | 114.4 | 286 | 874 | 94 |
|  |  | 20 | 255.1 | 638 | 784 | 84 |
|  |  | 30 | 457.7 | 1144 | 655 | 70 |
|  |  | 40 | 644.3 | 1611 | 621 | 66 |
| 20° C. followed by 48 hours at 4° C. | None | 0 | — | — | — | — |
|  | HP-β-CD | 2.5 | 11.6 | 29 | 2155 | 231 |
|  |  | 5 | 25.1 | 63 | 1992 | 213 |
|  |  | 10 | 52.7 | 132 | 1898 | 203 |
|  |  | 20 | 108.7 | 272 | 1840 | 197 |
|  |  | 30 | 186.7 | 467 | 1607 | 172 |
|  |  | 40 | 270 | 675 | 1481 | 159 |

$R_M$ designating the molar ratio of the cyclodextrin in the solution over the solubilized solute.
$R_m$ designating the weight ratio of the cyclodextrin in the solution over the solubilized solute.
$S/S_0$ designating the ratio of the AOL solubility relative to the intrinsic solubility of AOL in water.

TABLE 4

Solubility of AOL relative to the SBE-β-cyclodextrin (SBE-β-CD) and the temperature.

| Solubilization T° | CD | CD % (w/w) | AOL solubility mg/L | $S/S_0$ | CD/AOL ratio $R_m$ | $R_M$ |
|---|---|---|---|---|---|---|
| 20° C. | none | 0 | 0 | — | — | — |
|  | SBE-β-CD | 2.5 | 29.3 | 73 | 853 | 91 |
|  |  | 5 | 59.7 | 149 | 838 | 90 |
|  |  | 10 | 125.3 | 313 | 798 | 85 |
|  |  | 20 | 277.2 | 693 | 722 | 77 |
|  |  | 30 | 461.6 | 1154 | 650 | 70 |
|  |  | 40 | 666.8 | 1667 | 600 | 64 |
| 25° C. | none | 0 | — | — | — | — |
|  | SBE-β-CD | 2.5 | 35.8 | 90 | 698 | 75 |
|  |  | 5 | 74.9 | 187 | 668 | 71 |
|  |  | 10 | 156.5 | 391 | 639 | 68 |
|  |  | 20 | 340.5 | 851 | 587 | 63 |
|  |  | 30 | 575.2 | 1438 | 522 | 56 |
|  |  | 40 | 843.6 | 2109 | 474 | 51 |
| 30° C. | none | 0 | — | — | — | — |
|  | SBE-β-CD | 2.5 | 44.7 | 112 | 559 | 60 |
|  |  | 5 | 96.2 | 241 | 520 | 56 |
|  |  | 10 | 197.3 | 493 | 507 | 54 |
|  |  | 20 | 426.8 | 1067 | 469 | 50 |
|  |  | 30 | 720.2 | 1801 | 417 | 45 |
|  |  | 40 | 1043.7 | 2609 | 383 | 41 |
| 20° C. followed by 48 hours at 4° C. | none | 0 | — | — | — | — |
|  | SBE-β-CD | 2.5 | 16.9 | 42 | 1479 | 158 |
|  |  | 5 | 34.6 | 87 | 1445 | 155 |
|  |  | 10 | 70.7 | 177 | 1414 | 151 |
|  |  | 20 | 165.2 | 413 | 1211 | 130 |

TABLE 4-continued

Solubility of AOL relative to the SBE-β-cyclodextrin
(SBE-β-CD) and the temperature.

| Solubilization | | CD % | AOL solubility | | CD/AOL ratio | |
|---|---|---|---|---|---|---|
| T° | CD | (w/w) | mg/L | S/S$_0$ | R$_m$ | R$_M$ |
| | | 30 | 286.1 | 715 | 1049 | 112 |
| | | 40 | 456.7 | 1142 | 876 | 94 |

R$_M$ designating the molar ratio of the cyclodextrin in the solution over the solubilized solute.
R$_m$ designating the weight ratio of the cyclodextrin in the solution over the solubilized solute.
S/S$_0$ designating the ratio of the AOL solubility relative to the intrinsic solubility of AOL in water.

Using HP-β-CD, the highest solubility of AOL reached was 650 mg/L, at 30° C. with 40% (w/w) of HP-β-CD relative to the total weight of the composition. The solubility of AOL was multiplied by 1600.

Using SBE-β-CD, the solubility of AOL exceeded 1.0 g/L, at 30° C. with 40% of SBE-β-CD. The solubility was multiplied by 2600.

These values represent approximately the upper limits of solubility that can be reach with these two cyclodextrins.

Furthermore, the solubilization of AOL with SBE-β-CD did not modify the osmolarity of the initial SBE-β-CD solution. Consequently, AOL/SBE-β-CD formulations can be used with no risks of adverse effects associated to the hypertonia of the injected formulation.

Example 5: Solubility Testing in Buffer Containing Media

The solubility of AOL was tested in aqueous HP-β-CD and SBE-β-CD media at various concentrations and pH levels at room temperature. Some initial tests, where the pH of the formulations was adjusted only by addition of HCl or NaOH solutions, did evidence high variation in pH and difficulties to reach the target pH. Therefore, it was decided to prepare samples containing a buffering agent to get a stable pH and to facilitate the preparation of the formulations.

A citrate buffer was used at pH 5.5 and phosphate buffer were used at pH 6.5 and 7.5. The solubility results and the measured pH of the tested media, before and after addition of AOL are given in Tables 5 and 6. The solubility (mg/mL) is the mean of 2 independent replicates.

TABLE 5

Solubilization of AOL in different HP-β-CD buffered solutions.

| CD | CD % (w/w) | Buffer Agent (100 μM) | pH before adding AOL | pH after AOL solubilization | AOL solubility mg/mL | SD |
|---|---|---|---|---|---|---|
| HP-β-CD | 10.0 | Citrate | 5.61 | 5.61 | 0.079 | ±0.000 |
| | 10.0 | Phosphate 6.5 | 6.64 | 6.62 | 0.111 | ±0.002 |
| | 10.0 | Phosphate 7.5 | 7.66 | 7.64 | 0.112 | ±0.000 |
| | 20.0 | Citrate | 5.56 | 5.54 | 0.212 | ±0.005 |
| | 20.0 | Phosphate 6.5 | 6.61 | 6.59 | 0.274 | ±0.000 |
| | 20.0 | Phosphate 7.5 | 7.69 | 7.66 | 0.283 | ±0.001 |
| | 30.0 | Citrate | 5.59 | 5.57 | 0.505 | ±0.001 |
| | 30.0 | Phosphate 6.5 | 6.54 | 6.45 | 0.480 | ±0.016 |
| | 30.0 | Phosphate 7.5 | 7.70 | 7.67 | 0.540 | ±0.002 |
| | 40.0 | Citrate | 5.68 | 5.63 | 0.721 | ±0.006 |
| | 40.0 | Phosphate 6.5 | 6.75 | 6.72 | 0.676 | ±0.001 |
| | 40.0 | Phosphate 7.5 | 7.85 | 7.77 | 0.723 | ±0.029 |

TABLE 6

Solubilization of AOL in different HP-β-CD buffered solutions.

| CD | CD % (w/w) | Buffer Agent (100 μM) | pH before adding AOL | pH after AOL solubilization | AOL solubility mg/mL | SD |
|---|---|---|---|---|---|---|
| SBE-β-CD | 10.0 | Citrate | 5.40 | 5.63 | 0.165 | ±0.001 |
| | 10.0 | Phosphate 6.5 | 6.45 | 6.67 | 0.168 | ±0.001 |
| | 10.0 | Phosphate 7.5 | 7.50 | 7.68 | 0.170 | ±0.002 |
| | 20.0 | Citrate | 5.41 | 5.63 | 0.369 | ±0.002 |
| | 20.0 | Phosphate 6.5 | 6.47 | 6.72 | 0.382 | ±0.002 |
| | 20.0 | Phosphate 7.5 | 7.45 | 7.63 | 0.375 | ±0.002 |
| | 30.0 | Citrate | 5.57 | 5.27 | 0.675 | ±0.048 |
| | 30.0 | Phosphate 6.5 | 6.56 | 6.27 | 0.676 | ±0.005 |
| | 30.0 | Phosphate 7.5 | 7.49 | 7.26 | 0.685 | ±0.001 |
| | 40.0 | Citrate | 5.55 | 5.26 | 1.136 | ±0.004 |
| | 40.0 | Phosphate 6.5 | 6.54 | 6.30 | 1.207 | ±0.055 |
| | 40.0 | Phosphate 7.5 | 7.52 | 7.32 | 1.183 | ±0.005 |

HP-β-cyclodextrin and SBE-β-cyclodextrin gave the highest solubility values of 0.723 mg/mL and 1.207 mg/mL respectively at 40% of cyclodextrin and at pH 7.5 for HP-β-cyclodextrin and at pH 6.5 for SBE-β-cyclodextrin (both using phosphate buffer).

It is clearly observed that with increasing concentrations of cyclodextrin the solubility of AOL also increases with tested cyclodextrines. No effect of the different buffers at different pH values is observed. After AOL has been dissolved and reached its maximum solubility in the media, the pH remains in the range of ±0.4 compared to the pure media for SBE-β-cyclodextrin and in the range of ±0.2 for all other cyclodextrin media. This indicates that the buffer capacity of the medium is sufficient.

Example 6: SBE-β-CD Enhances the Chemical Stability of AOL

Figure 2:
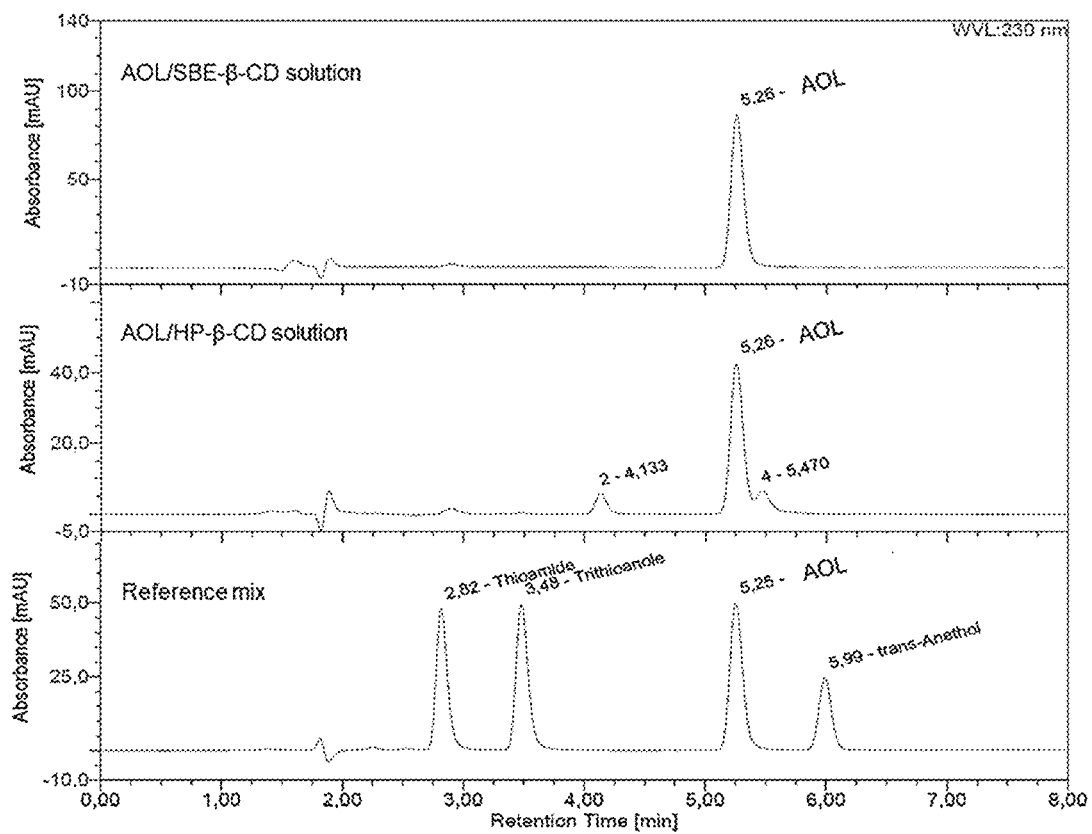
FIG. 2 is a comparative HPLC chromatogram showing the chemical stability of AOL in the AOL/SBE-β-CD solution (top). The AOL/HP-β-CD solution HPLC analysis (in the middle) showed impurities at retention time 4.13 and 5.5 min that were not related to the standard mixture of compounds AOL, trithioanole, thioamide and trans-anethole (bottom).

During the experimental condition of Example 4, AOL presented chemical instability when associated with HP-β-CD as evidenced by the HPLC analysis shown in FIG. 2.

The HPLC analysis of the AOL/HP-β-CD solution revealed impurities having a retention time ($T_R^{-4.1}$ and 5.5 min) not corresponding to any one of the compounds of the standard mixture (Example 2).

On the contrary, the HPLC analysis of the AOL/SBE-β-CD revealed no impurities.

Consequently, SBE-β-CD not only enhances the solubility of AOL in aqueous media, but also ensures its chemical stability. Further evidence regarding the influence of SBE-β-CD to the chemical stability of AOL is presented in example 11.

Example 7: Co-Solvent Addition

SBE-β-CD compatible excipients, namely polyethylene glycol and polysorbate (Tween), were evaluated for their AOL aqueous solubilizing power. Screening was carried out in same conditions as that of solubilization screening by cyclodextrins (see Example 3).

Figure 3:
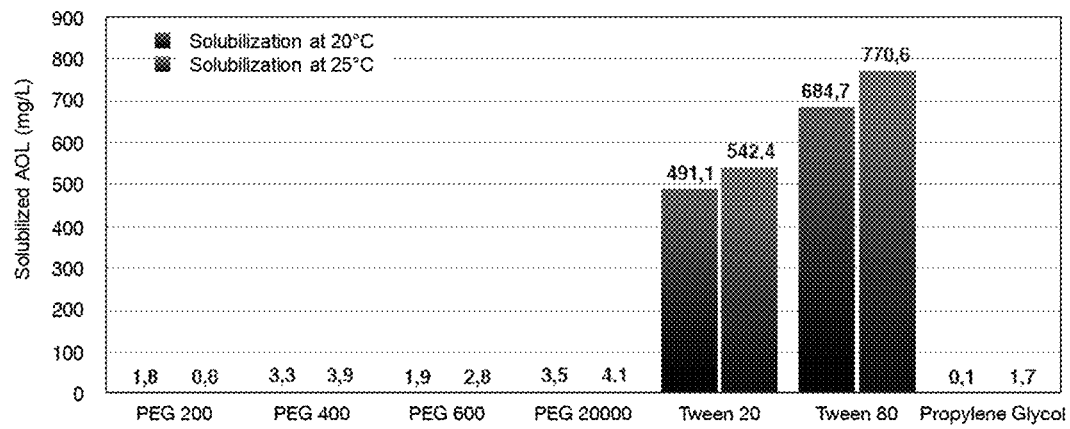
FIG. 3 is a graph showing the screening of SBE-β-CD compatible co-solvents at 20% (w/w) for the solubilization of AOL.

Briefly, 20% (w/w) solutions of each excipient were prepared. An excess of AOL was added and the solutions were analyzed by HPLC after 4 hours of stirring. The results are shown in FIG. 3.

Figure 4:
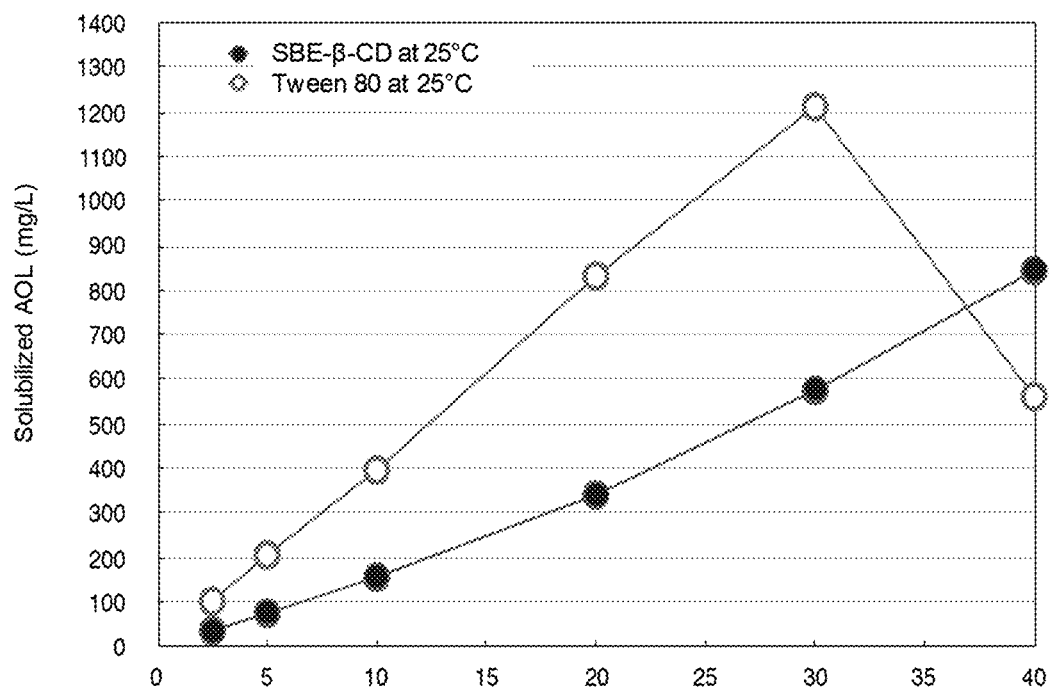
FIG. 4 is a graph showing the comparative solubility diagram of AOL in presence of SBE-β-CD and Tween 80 in the concentrations of 2.5, 5, 10, 20, 30 and 40% (w/w) each.

As presented in FIG. 4, at the same temperature and concentration of excipient, AOL presented a higher solubility in Tween 80 (Polysorbate 80) than in SBE-β-CD solutions.

Nevertheless, raising the concentration of Tween 80 was hindered by the increased viscosity of the solution.

Furthermore, AOL presented chemical stability issues when stored in Tween 80 at 20% (w/w) aqueous media.

Figure 5:
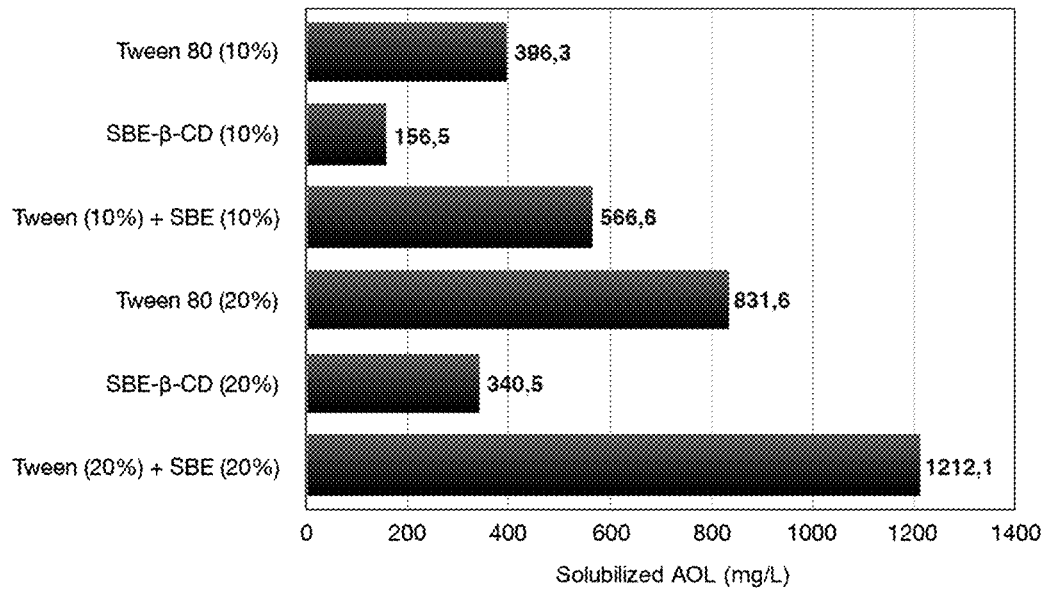
FIG. 5 is a graph showing the solubilization of AOL at 25° C. by Tween 80, 10% (w/w); SBE-β-CD 10% (w/w); Tween 80 and SBE-β-CD 10% (w/w) each; Tween 80 20% (w/w); SBE-β-CD 20% (w/w); and Tween 80 and SBE-β-CD 20% (w/w) each.

The effect of the combination of SBE-β-CD and Tween 80 was measured in a comparative assay by solubilizing AOL in: (A) Tween 80, 10% (w/w); (B) SBE-β-CD 10% (w/w) (C) Tween 80 and SBE-β-CD 10% (w/w) each; (D) Tween 80 20% (w/w) (E) SBE-β-CD 20% (w/w); and (F) Tween 80 and SBE-β-CD 20% (w/w) each. The results are presented in FIG. 5.

Combining excipients of such different types may have led to incompatibilities leading for example to precipitation and/or may have also led to deleterious effects on solubility of AOL. Surprisingly, the solubilization effect of the combination Tween 80/SBE-β-CD had a cumulative effect of each excipient and no incompatibility was identified.

Further assays, resumed in Tables 7 and 8, confirmed that Tween 80/SBE-β-CD is a promising excipient mixture for the solubilization of AOL.

PVP 12PF did not had any influence on the solubility of AOL. Cremophor ELP increased the viscosity of the formulation causing difficulties to stir and handle the solution. For this reason, some of these Cremophor ELP containing concepts could not be further processed.

TABLE 7

Results of AOL solubility enhancement by adding PVP 12PF, Cremophor ELP and Tween 80 in SBE-β-cyclodextrin media.

| CD | | Co-solvent | | AOL solubility | |
|---|---|---|---|---|---|
| Type | % (w/w) | Type2 | % (w/w) | mg/mL | SD |
| HP-B-CD | 20 | PVP 12PF | 0 | 0.283 | ±0.001 |
| | 20 | | 0.5 | 0.296 | ±0.003 |
| | 20 | | 2.0 | 0.291 | ±0.001 |
| | 30 | | 0 | 0.540 | ±0.002 |
| | 30 | | 0.5 | 0.532 | ±0.001 |
| | 30 | | 2.0 | 0.517 | ±0.001 |
| | 20 | Cremophor | 0 | 0.283 | ±0.001 |
| | 20 | | 10 | 0.545 | ±0.001 |
| | 20 | | 20 | 0.814 | ±0.002 |
| | 30 | | 0 | 0.540 | ±0.002 |
| | 30 | | 10 | 0.642 | ±0.001 |
| | 30 | | 20 | * | |
| | 20 | Tween 80 | 0 | 0,283 | ±0.001 |
| | 20 | | 2 | 0.329 | ±0.000 |
| | 20 | | 10 | 0.396 | ±0.001 |
| | 20 | | 20 | 0.660 | ±0.009 |
| | 30 | | 0 | 0.540 | ±0.002 |
| | 30 | | 2 | 0.426 | ±0.003 |
| | 30 | | 10 | 0.439 | ±0.007 |
| | 30 | | 20 | 1.685 | ±0.018 |

*: the viscosity of the sample did not allow the handling and the quantification of AOL.

For Tween 80, the viscosity was also high but all concepts could be properly prepared and analyzed. From Table 7, it is observed that higher Tween 80 concentrations lead to higher solubility values of AOL in SBE-β-cyclodextrin media. After the AOL has dissolved and reached its maximum solubility in the media, the pH remained in the range of ±0.3 compared to the pure media for SBE-β-cyclodextrin.

TABLE 8

Results of AOL solubility enhancement by adding PVP 12PF, Cremophor ELP and Tween 80 in SBE-β-cyclodextrin media.

| CD | | Co-solvent | | AOL solubility | |
|---|---|---|---|---|---|
| Type | % (w/w) | Type2 | % (w/w) | mg/mL | SD |
| SBE-B-CD | 20 | PVP 12PF | 0 | 0.375 | ±0.002 |
| | 20 | | 0.5 | 0.389 | ±0.001 |
| | 20 | | 2.0 | 0.371 | ±0.001 |
| | 30 | | 0 | 0.685 | ±0.001 |
| | 30 | | 0.5 | 0.668 | ±0.002 |
| | 30 | | 2.0 | 0.670 | ±0.001 |
| | 20 | Cremophor | 0 | 0.375 | ±0.002 |
| | 20 | | 10 | 0.644 | ±0.016 |
| | 20 | | 20 | * | |
| | 30 | | 0 | 0.685 | ±0.001 |
| | 30 | | 10 | 0.814 | ±0.080 |
| | 30 | | 20 | * | |
| | 20 | Tween 80 | 0 | 0.375 | ±0.002 |
| | 20 | | 2 | 0.374 | ±0.001 |
| | 20 | | 10 | 0.587 | ±0.002 |
| | 20 | | 20 | 0.829 | ±0.002 |
| | 30 | | 0 | 0.685 | ±0.001 |
| | 30 | | 2 | 0.630 | ±0.003 |
| | 30 | | 10 | 0.616 | ±0.018 |
| | 30 | | 20 | 1.285 | ±0.112 |

*: the viscosity of the sample did not allow the handling and the quantification of AOL.

Example 8: Spray-Drying

Five (5) media were prepared to evaluate the AOL solubility in solvents frequently used for spray-drying. To ensure a rapid preparation together with a complete solubilization of the SBE-β-CD, a margin was taken for the preparation of the media by reducing the concentration of the SBE-β-CD (in regards to the maximum solubility evaluated) for some concepts. The following compositions were used.

MeOH/DCM (90/10) containing 1.5% SBE-β-CD;
EtOH/water (10/90) containing 10% SBE-β-CD;
ACN/water (50/50) containing 4% SBE-β-CD;
Acetone/water (50/50) containing 10% SBE-β-CD; and
MeOH/ethyl acetate (90/10) containing 1.5% SBE-β-CD.
Two media were selected for spray-drying:
MeOH/DCM (90/10) containing 1.5% SBE-β-CD
Acetone/water (50/50) containing 10% SBE-β-CD

TABLE 9

Summary of all compositions and production characteristics of AOL solid dispersions prepared by spray-drying. Batch 050 derived from an SBE-β-CD solution at 40% in a phosphate buffer at 100 mM and pH 7.5, diluted four times, to reach an acceptable viscosity for spray-drying.

| Powder batch | RM | Rm | AOL (g) | SBE-β-CD (g) | Solvent(s) ratio | Feed medium g | Spray-drying time (min) | Process yield (%) |
|---|---|---|---|---|---|---|---|---|
| 044 | 32 | 300 | 0.0117 | 3.5000 | Me$_2$CO/H$_2$O 50/50 | 35.0117 | 6.33 | 91.1 |
| 045 | 22 | 200 | 0.0175 | 3.5000 | Me$_2$CO/H$_2$O 50/50 | 35.0165 | 6.50 | 89.7 |

TABLE 9-continued

Summary of all compositions and production characteristics of AOL solid dispersions prepared by spray-drying. Batch 050 derived from an SBE-β-CD solution at 40% in a phosphate buffer at 100 mM and pH 7.5, diluted four times, to reach an acceptable viscosity for spray-drying.

| Powder batch | RM | Rm | AOL (g) | SBE-β-CD (g) | Solvent(s) ratio | Feed medium g | Spray-drying time (min) | Process yield (%) |
|---|---|---|---|---|---|---|---|---|
| 046 | 17 | 160 | 0.0218 | 3.5000 | Me₂CO/H₂O 50/50 | 35.0218 | 5.97 | 91.9 |
| 047 | 32 | 300 | 0.0118 | 3.5250 | MeOH/DCM 90/10 | 235.0118 | 39.43 | 84.8 |
| 048 | 22 | 200 | 0.0176 | 3.5250 | MeOH/DCM 90/10 | 235.0176 | 39.48 | 91.0 |
| 049 | 11 | 100 | 0.0353 | 3.5250 | MeOH/DCM 90/10 | 235.0352 | 39.33 | 88.4 |
| 050 | 43 | 400 | 0.0100 | 4.0000 | H₂O | 40.0000 | 15.35 | 72.0 |

Assay and purity were determined using HPLC. The assay obtained for the spray-dried powders produced with organic solvents as feed media are rather high, with values close to 100% (from 98.36% to 103.02%), excepted for batch 046 which exhibits a slightly lower assay around 93%. For the spray-dried powder produced from the aqueous solution (batch 050), a satisfying assay value is obtained (around 77%).

In terms of purity, the six powders obtained from the organic solvents exhibit low value for the area % of the degradation-related fragment at m/z 257.2 (Mass spectrometry analysis).

As a conclusion, good process yields and no increase in degradation during the spray-drying process were obtained.

Example 9: Aqueous Reconstitution of the Spray-Dried Powders

Reconstitution tests for the batches obtained in Example 8 were performed in purified water, Tween 80 10% (w/w) and Tween 80 20% (w/w) aqueous media.

One gram of each spray-dried powder was filled in a 10 mL glass vial. 3.3 mL (i.e., 3.3 g) of aqueous medium was added. The vials were consequently manually shaken (vigorously) up to 30 seconds to ensure a good solubilization of the powder.

Visual evaluation was performed past the reconstitution, after 1 hour, 4 hours, 20 hours and 48 hours.

Reconstitution tests led to no sedimentation, with no evolution overtime.

Example 10: AOL/SBE-β-CD Freeze-Draying/Lyophilization

A 40% (w/w) AOL/SBE-β-CD solution obtained at 20° C. as previously described (Example 4) was subjected to freeze-drying (also called lyophilization) leading to an amorphous powder.

The amorphous powder was solubilized in water leading to a [AOL/SBE-β-CD] concentration of 715 g/L, corresponding to an AOL concentration of 1.54 g/L.

Further aqueous AOL/SBE-β-CD solutions were prepared comprising 0.081 mg/mL to 0.250 mg/mL of AOL and 5 or 10% w/w of SBE-β-CD (Table 10).

Concepts with 5% and 10% SBE-β-CD were lyophilized since in previous screenings these concepts resulted in the optimal post-lyophilization cakes. Reconstitution was fast and only a minor amount of shaking is necessary for the concepts containing 10% SBE-beta-cyclodextrin.

The lyophilized cakes were reconstituted in two different volumes of saline solution. The aim was to reach the concentration of the starting solution or of a more concentrated solution.

The composition of the reconstituted solutions as well as their stability after 1 day at 5° C. and 25° C. are tabulated in Table 11.

Clearly the SBE-β-CD/AOL ratio of concepts 208-188 BA, BB, DA and DB is too low and results in particles in the reconstituted solution. For concepts with a higher SBE/AOL ratio no particles are observed after 1 day at 25° C.

Concepts with citrate buffer show identic results as concepts with phosphate buffer.

TABLE 10

Composition of starting solutions that were lyophilized and the evaluation the lyophilized cake reconstitution time

| Batch | AOL (mg/mL) | SBE (w/v) | Weight Ratio SBE/AOL | molar Ratio SBE/AOL | Buffer | Reconstitution time |
|---|---|---|---|---|---|---|
| 237-006AA | 0.163 | 10 | 615 | 66 | 25 mM phosphate pH 7.5 | Fast reconstitution (2 s), some shaking |
| 237-006AB | 0.081 | 5 | 615 | 66 | 12.5 mM phosphate pH 7.5 | Fast reconstitution (2 s), no shaking |
| 237-006BA | 0.250 | 10 | 400 | 43 | 25 mM phosphate pH 7.5 | Fast reconstitution (2 s), some shaking |
| 237-006BB | 0.125 | 5 | 400 | 43 | 12.5 mM phosphate pH 7.5 | Fast reconstitution (2 s), no shaking |
| 237-006CA | 0.163 | 10 | 615 | 66 | 25 mM citrate pH 6.5 | Fast reconstitution (2 s), some shaking |
| 237-006CB | 0.081 | 5 | 615 | 66 | 12.5 mM citrate pH 6.5 | Fast reconstitution (2 s), no shaking |
| 237-006DA | 0.250 | 10 | 400 | 43 | 25 mM citrate pH 6.5 | Fast reconstitution (2 s), some shaking |
| 237-006DB | 0.125 | 5 | 400 | 43 | 12.5 mM citrate pH 6.5 | Fast reconstitution (2 s), no shaking |
| 210-188AC | 0.188 | 10 | 533 | 57 | 25 mM citrate pH 6.5 | Good reconstitution (5 s), shaking |
| 210-188AD | 0.094 | 5 | 533 | 57 | 12.5 mM citrate pH 6.5 | Fast reconstitution (2 s), no shaking |

TABLE 11

Composition and visuals of reconstituted solutions at different time points.

| Batch number | Reconstituted in: 0.9% NaCl (mL) | AOL. (mg/mL) | SBE % (w/v) | Weight Ratio SBE/AOL | Molar Ratio SBE/AOL | To | Visual evaluation $T_{1d}$ (5° C.) | $T_{1d}$ (25° C.) |
|---|---|---|---|---|---|---|---|---|
| 237-006AA | 5.000 | 0.163 | 10.00 | 613 | 66 | 0 | 0/+ | 0 |
|  | 1.250 | 0.650 | 40.00 | 615 | 66 | 0 | 0 | 0 |
| 237-006AB | 5.000 | 0.081 | 5.00 | 617 | 66 | 0 | 0/+ | — |
|  | 0.625 | 0.650 | 40.00 | 615 | 66 | 0 | 0 | — |
| 237-006BA | 5.000 | 0.250 | 10.00 | 400 | 43 | + | + | + |
|  | 1.250 | 1.000 | 40.00 | 400 | 43 | + | + | + |
| 237-006BB | 5.000 | 0.125 | 5.00 | 400 | 43 | + | + | + |
| 237-006CA | 5.000 | 0.163 | 10.00 | 613 | 66 | 0 | 0/+ | 0 |
|  | 1.250 | 0.650 | 40.00 | 615 | 66 | 0 | 0 | 0 |
| 237-006CB | 5.000 | 0.081 | 5.00 | 617 | 66 | 0 | 0/+ | 0 |
|  | 0.625 | 0.650 | 40.00 | 615 | 66 | 0 | 0 | — |
| 237-006DA | 5.000 | 0.250 | 10.00 | 400 | 43 | + | + | + |
|  | 1.250 | 1.000 | 40.00 | 400 | 43 | + | + | + |
| 237-006DB | 5.000 | 0.125 | 5.00 | 400 | 43 | + | + | + |
| 210-188AC | 4.000 | 0.235 | 12.5 | 533 | 57 | 0 | 0 | 0 |
|  | 5.000 | 0.188 | 10.00 | 533 | 57 | 0 | 0 | 0 |
| 210-188AD | 4.000 | 0.177 | 6.25 | 533 | 57 | 0 | 0 | 0 |
|  | 5.000 | 0.094 | 5.00 | 533 | 57 | 0 | 0 | 0 |

0: No particles;
0/+ Very small amount of particles;
+: Small amount of particles.

Example 11: Comparative Examples of SBE-β-CD—AOL Formulations

This example further highlights the advantageous solubility and chemical stability of AOL formulations presenting the SBE-β-CD/AOL molar ratio according to the invention.

The assessed formulations were prepared in volumetric flasks on 250 mL scale.

The required amount of concentrated solubilization medium (consisting of 20% w/v SBE-β-CD and 50 mM phosphate buffer) and the required amount of purified water was added so as to obtain the formulations presenting the SBE-β-CD/AOL molar ratios presented in table 12. The obtained solutions were magnetically stirred overnight. The presence of undissolved particles was visually assessed.

The visual inspection of the obtained formulations showed the effective solubilization of AOL according to the present invention, as opposed to the dispersions obtained with inferior SBE-β-CD/AOL molar ratios who presented undissolved particles.

The formulations presenting an SBE-β-CD/AOL molar ratio inferior to 50 presented an increasing amount of undissolved particles, the ones presenting an SBE-β-CD/AOL molar ratio inferior to 10 being clearly non-suitable of intravenous administration.

The formulations presenting undissolved particles were filtered through 0.2 μm RC filters.

All the obtained formulations were transferred to glass type III bottles and flushed with nitrogen during 15 minutes.

An aliquot of each solution was taken for UPLC-UV analysis and pH measurement. All formulations presented a pH of 7.3-7.5.

The HPLC-UV chromatogram was monitored at 346 nm focusing on the AOL degradation products AOL-S-oxide (RRT 0.58: RRF 0.58) and AOL-3-one (RRT 0.84: RRF 0.62).

TABLE 12 presents the comparative formulations of example 11 and the HPLC-UV chromatographic analysis results.

| Molar ratio SBE/AOL | HPLC-UV signal area % | | | Measured ATT concentration (mg/mL) |
|---|---|---|---|---|
| | AOL-S-oxide | AOL-3-one | AOL | |
| 1/1 | 0.06 | 0.01 | 1.43 | 0.1649 |
| 2/1 | 0.06 | 0.02 | 2.41 | 0.1388 |
| 10/1 | 0.13 | 0.03 | 12.89 | 0.1487 |
| 50/1 | 0.31 | 0.03 | 67.37 | 0.1554 |
| 80/1 | 0.43 | 0.03 | 99.73 | 0.1438 |
| 115.3/1 | 0.83 | 0.04 | 96.64 | 0.0966 |
| 150/1 | 0.55 | 0.05 | 102.64 | 0.0789 |
| 200/1 | 1.06 | 0.10 | 100.99 | 0.0583 |
| 410/1 | 0.77 | 0.15 | 98.59 | 0.0277 |

The HPLC-UV analysis showed a significantly enhanced chemical stability of AOL within the formulations of the invention.

The results of table 12 are presented in table 13 as the % proportion of AOL that was chemically degraded to AOL-S-oxide and AOL-3-one. Indeed, the formulations of the present invention showed a significantly reduced proportion of AOL degradation to AOL-S-oxide and AOL-3-one compared to the formulations wherein the SBE-β-CD/AOL molar ratio less than 10.

TABLE 13 showing the proportion of chemical degradation of AOL to AOL-S-oxide and AOL-3-one in the obtained formulations, right after their preparation and before freeze-drying.

| Molar ratio SBE/AOL | HPLC-UV signal area % | | | AOL-S-oxide/ AOL (%) | AOL-3-one/ AOL (%) |
|---|---|---|---|---|---|
| | AOL-S-oxide | AOL-3-one | AOL | | |
| 1/1 | 0.06 | 0.01 | 1.43 | 4.2 | 0.70 |
| 2/1 | 0.06 | 0.02 | 2.41 | 2.5 | 0.83 |
| 10/1 | 0.13 | 0.03 | 12.89 | 1.0 | 0.23 |

TABLE 13-continued showing the proportion of chemical degradation of AOL to
AOL-S-oxide and AOL-3-one in the obtained formulations,
right after their preparation and before freeze-drying.

| Molar ratio SBE/AOL | HPLC-UV signal area % | | | AOL-S-oxide/ AOL (%) | AOL-3-one/ AOL (%) |
|---|---|---|---|---|---|
| | AOL-S-oxide | AOL-3-one | AOL | | |
| 50/1 | 0.31 | 0.03 | 67.37 | 0.5 | 0.04 |
| 80/1 | 0.43 | 0.03 | 99.73 | 0.4 | 0.03 |
| 115.3/1 | 0.83 | 0.04 | 96.64 | 0.9 | 0.04 |
| 150/1 | 0.55 | 0.05 | 102.64 | 0.5 | 0.05 |
| 200/1 | 1.06 | 0.10 | 100.99 | 1.0 | 0.10 |
| 410/1 | 0.77 | 0.15 | 98.59 | 0.8 | 0.15 |

Then, 5 mL of each solution was filled in 10 mL glass type I vials, that were lyophilized according to the protocol presented in table 14.

TABLE 14 presenting the lyophilization conditions of example 11.

| Time (hh:mm) | T (° C.) | P (µbar) | Temperature ramp |
|---|---|---|---|
| | 20 | Atmospheric | |
| 2:30 | −40 | Atmospheric | ramp: 0.4° C./min |
| 6:00 | −40 | Atmospheric | stable temperature |
| 0:25 | −20 | 100 | ramp: 0.8° C./min |
| 30:00 | −20 | 100 | stable temperature |
| 0:13 | −10 | 100 | ramp: 0.8° C./min |
| 30:00 | −10 | 100 | stable temperature |
| 0:44 | 25 | <100 | ramp: 0.8° C./min |
| 30:00 | 25 | <100 | stable temperature |

Each freeze-dried formulation was reconstituted in 4.7 mL of purified water.

An aliquot of each one of the obtained solutions was taken for U(H)PLC-UV analysis for the chemical stability assessment after reconstitution. The results are presented in table 15.

Figure 6:
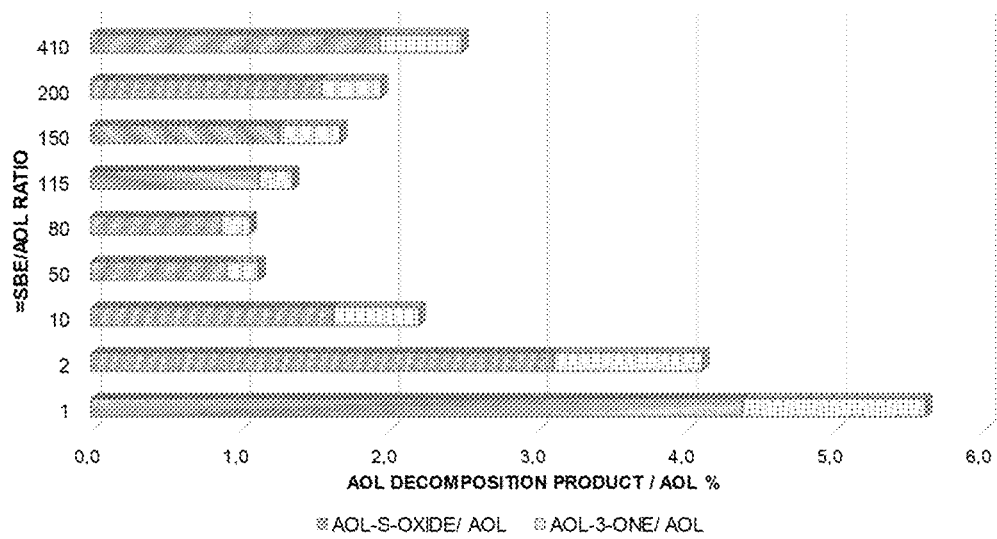
FIG. 6 is a graph showing the proportion of AOL decomposition products, AOL-S-oxide and AOL-3-one, relative to AOL, in AOL/SBE-β-CD formulations presenting SBE-β-CD on AOL molar ratio of 1/1, 2/1, 10/1, 50/1, 80/1, 115.3/1; 150/1, 200/1, 410/1. The proportion of AOL decomposition products is calculated from the chromatographic HPLC-UV analysis of reconstituted solutions from freeze-dried powders presenting the corresponding molar ratios that were stored at room temperature, protected from light for 72 hours.

The remaining quantity of reconstituted solutions were stored at room temperature, protected from light for 72 hours and analyzed via HPLC-UV for the chemical stability assessment after 72 hours post reconstitution. The results are presented in table 16. The results are visually represented in the graph of FIG. 6.

TABLE 15 showing the proportion of chemical degradation of AOL to
AOL-S-oxide and AOL-3-one in the obtained solutions right
after their reconstitution from the free-dried formulation.

| Molar ratio SBE/AOL | HPLC-UV signal area % | | | AOL-S-oxide/ AOL (%) | AOL-3-one/ AOL (%) |
|---|---|---|---|---|---|
| | AOL-S-oxide | AOL-3-one | AOL | | |
| 1/1 | 0.061 | 0.014 | 1.4565 | 4.2 | 0.96 |
| 2/1 | 0.0815 | 0.0215 | 2.8645 | 2.8 | 0.75 |
| 10/1 | 0.1705 | 0.044 | 13.522 | 1.3 | 0.33 |
| 50/1 | 0.47 | 0.07 | 67.21 | 0.7 | 0.10 |
| 80/1 | 0.64 | 0.08 | 100.11 | 0.6 | 0.08 |
| 115.3/1 | 1 | 0.12 | 95.96 | 1.0 | 0.13 |
| 150/1 | 1.03 | 0.22 | 102.41 | 1.0 | 0.21 |
| 200/1 | 1.41 | 0.24 | 99.99 | 1.4 | 0.24 |
| 410/1 | 1.8 | 0.23 | 97.78 | 1.8 | 0.24 |

TABLE 16 showing the proportion of chemical degradation of AOL to
AOL-S-oxide and AOL-3-one in the obtained solutions 72 hours
after their reconstitution from the free-dried formulation.

| Molar ratio SBE/AOL | HPLC-UV signal area % | | | AOL-S-oxide/ AOL (%) | AOL-3-one/ AOL (%) |
|---|---|---|---|---|---|
| | AOL-S-oxide | AOL-3-one | AOL | | |
| 1/1 | 0.0625 | 0.0175 | 1.427 | 4.4 | 1.23 |
| 2/1 | 0.087 | 0.028 | 2.799 | 3.1 | 1.00 |
| 10/1 | 0.216 | 0.0765 | 13.2775 | 1.6 | 0.58 |
| 50/1 | 0.6 | 0.14 | 65.68 | 0.9 | 0.21 |
| 80/1 | 0.86 | 0.19 | 98.31 | 0.9 | 0.19 |
| 115.3/1 | 1.07 | 0.21 | 94.58 | 1.1 | 0.22 |
| 150/1 | 1.28 | 0.41 | 100.87 | 1.3 | 0.41 |
| 200/1 | 1.53 | 0.39 | 98.53 | 1.6 | 0.40 |
| 410/1 | 1.87 | 0.53 | 96.35 | 1.9 | 0.55 |

GENERAL CONCLUSION

Among the panel of cyclodextrins tested, SBE-β-CD was found to be the most potent solubilizing agent for AOL (examples 3-5). Furthermore, SBE-β-CD preserved the chemical stability of AOL, which was not the case the HP-β-CD (Example 6).

Satisfactory solubilization of AOL by means of SBE-β-CD was achieved. Nevertheless, according to the EMA guidelines, limited quantity of SBE-β-CD that can be injected per diem can be tolerated.

AOL/SBE-β-CD formulations were particularly advantageous when freeze-dried. The AOL in the aqueously reconstituted freeze-dried powder showed advantageous solubility and physicochemical stability (batches 210-188AC and 210-188AD, Example 10).

Furthermore, the use of a complementary excipient was contemplated (Example 7). The screening of several SBE-β-CD compatible co-solvents revealed Tween 80 as a promising co-solvent candidate.

However, Tween 80 at high concentrations compromised the chemical stability of AOL. Furthermore, the obtained AOL-Tween 80 solutions were highly viscous hindering the syringeability of such AOL formulations and thus their application in injectable forms.

Using an optimized AOL/SBE-β-CD molar ratio enabled the Applicant to overcome all the aforementioned shortcomings. Indeed, the obtained formulation can be injected without exceeding the daily cyclodextrin administration threshold, solubilizes AOL without presenting a prohibiting viscosity. The chemical stability of AOL was maintained by such a formulation. Optimal solubilization was observed at an SBE-β-CD/AOL molar ratio superior to 29. Without willing to be bound by a theory the complex association (interaction outside the cavity of the cyclodextrin) enhances its solubility without hindering its bioavailability when the formulation is administered to a subject in need thereof.

In addition, spray-dried AOL/SBE-β-CD powders were prepared that, when reconstituted in aqueous media (preferably aqueous media containing Tween 80), yield injectable compositions with the above advantageous syringeability, viscosity, chemical stability and bioavailability aspects.

As previously discussed, the compound of formula (I)/SBE-β-CD formulations of the present invention ensure the complete solubilization of the compound of formula (I). Such effective solubilization is particularly advantageous in terms of safety and quality of intravenous administration forms. Indeed, the presence of insoluble particles in the injected formulation may present a risk to the subject. Furthermore, substantial filtering of the formulation shall be needed prior to its injection. Such filtering shall affect the quality of the product since the quantity of the active ingredient in different batches shall present fluctuations among different batches of product. Lastly, such dosage fluctuation shall present a further risk for the subject since the exact amount of the administered compound of formula (I).

Furthermore, the association of compound of formula (I)/SBE-β-CD in the molar ratio according to the invention yields an unexpected chemical stabilization of the compound of formula (I), right after it's solubilization, after it's free-drying and reconstitution in aqueous media or even 72 hours past the reconstitution of the freeze-dried powder in such media. Thus, by impeding the formation of degradation products, the therapeutic effect of compound of formula (I) is guaranteed without the risk of side-effects provoked by the degradation products.

In conclusion, the formulation of a compound of formula (I) according to the present invention are indeed suitable for intravenous administration not only because of the effective solubilization but also thanks to the chemical stabilization the compound of formula (I).

The invention claimed is:

1. A composition comprising sulfobutyl ether-beta-cyclodextrin and a compound of formula (I);

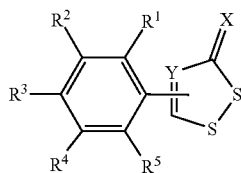

or a pharmaceutically acceptable tautomer, salt or solvate thereof wherein:
X is S, O or NHOH;
Y is CH, C or N;
$R^1$, $R^2$, $R^4$ and $R^5$ each independently is hydrogen, hydroxy, halo, amino, alkylsulfonyl, aminosulfonyl, cyano, nitro, carboxy, aryl, alkoxy, haloalkyl, alkylamino, aminoalkyl, nitrooxyalkyl or carboxyalkyl;
$R^3$ is hydroxy or methoxy; or $R^3$ and $R^2$ together with the carbon atoms to which they are attached form a 5-membered heteroaryl moiety wherein —$R^3$—$R^2$— is -A—$CR^6$=B— or —B=$CR^6$-A-; wherein:
A is O, S or $NR^7$; wherein $R^7$ is hydrogen, $C_1$-$C_8$ alkyl or alkyloxycarbonyl;
B is CH or N; and
$R^6$ is hydrogen, hydroxy, halo, amino, alkylsulfonyl, aminosulfonyl, cyano, nitro, carboxy, aryl, alkoxy, haloalkyl, alkylamino, aminoalkyl, nitrooxyalkyl or carboxyalkyl;
wherein the molar ratio of the sulfobutyl ether-beta-cyclodextrin to the compound of formula (I) ranges from 10 to 400.

2. The composition according to claim 1, wherein: X is S or O; Y is CH or N.

3. The composition according to claim 1, wherein:
X is S; Y is CH; and wherein the molar ratio of the sulfobutyl ether-beta-cyclodextrin to the compound of formula (I) ranges from 57 to 200.

4. The composition according to claim 1, wherein the compound of formula (I) is selected from:
5-(4-methoxyphenyl)-3H-1,2-dithiole-3-thione;
5-(4-hydroxyphenyl)-3H-1,2-dithiole-3-thione;
5-(4-hydroxyphenyl)-3H-1,2-dithiol-3-one;
5-(4-hydroxyphenyl)-3H-1,2-dithiol-3-one oxime;
5-(4-hydroxyphenyl)-3H-1,2,4-dithiazole-3-thione;
4-(4-hydroxyphenyl)-3H-1,2-dithiole-3-thione;
5-(2-hydroxybenzo[d]oxazol-5-yl)-3H-1,2-dithiole-3-thione;
5-(2-hydroxybenzo[d]thiazol-6-yl)-3H-1,2-dithiole-3-thione;
5-(benzofuran-5-yl)-3H-1,2-dithiole-3-thione; and
methyl 5-(3-thioxo-3H-1,2-dithiol-5-yl)-1H-indole-1-carboxylate.

5. The composition according to claim 1, wherein the concentration in compound of formula (I) ranges from 0.04 to 1.2 mg/mL.

6. The composition according to claim 1, wherein the concentration in compound of formula (I) ranges from 0.1 to 1.0 mg/mL.

7. The composition according to claim 1, wherein the amount of the sulfobutyl ether-beta-cyclodextrin ranges from 1 to 40% (w/w).

8. The composition according to claim 1, wherein the amount of the sulfobutyl ether-beta-cyclodextrin ranges from 2.5 to 30% (w/w) in weight relative to the total weight of the composition.

9. The composition according to claim 1, further comprising at least one buffer selected from the group consisting of citrate buffer, acetate buffer, tris (hydroxymethyl) aminomethane and phosphate buffer.

10. The composition according to claim 1, said composition having a pH ranging from 6 to 7.8.

11. The composition according to claim 1, being a solid composition.

12. The composition according to claim 1, said composition being a pharmaceutical composition further comprising at least one pharmaceutically acceptable liquid carrier.

13. The composition according to claim 12, wherein at least one pharmaceutically acceptable liquid carrier is water.

14. A kit-of-parts or a medical device comprising said kit-of-parts, wherein said kit-of-parts comprises a composition comprising sulfobutyl ether-beta-cyclodextrin and a compound of formula (I);

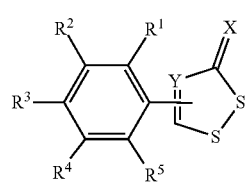

or a pharmaceutically acceptable tautomer, salt or solvate thereof wherein:
X is S, O or NHOH;
Y is CH, C or N;
$R^1$, $R^2$, $R^4$ and $R^5$ each independently represent hydrogen, hydroxy, halo, amino, alkylsulfonyl, aminosulfonyl, cyano, nitro, carboxy, aryl, alkoxy, haloalkyl, alkylamino, aminoalkyl, nitrooxyalkyl or carboxyalkyl;
$R^3$ hydroxy or methoxy; or $R^3$ and $R^2$ together with the carbon atoms to which they are attached form 5-membered a heteroaryl moiety wherein —$R^3$—$R^2$— is -A-$CR^6$=B— or —B=$CR^6$-A-; wherein:

A is O, S or $NR^7$; wherein $R^7$ is hydrogen, $C_1$-$C_8$ alkyl or alkyloxycarbonyl;

B is CH or N; and $R^6$ is hydrogen, hydroxy, halo, amino, alkylsulfonyl, aminosulfonyl, cyano, nitro, carboxy, aryl, alkoxy, haloalkyl, alkylamino, aminoalkyl, nitrooxyalkyl or carboxyalkyl; wherein the molar ratio of the sulfobutyl ether-beta-cyclodextrin to the compound of formula (I) ranges from 10 to 400.

* * * * *